United States Patent
Orian-Rousseau et al.

(10) Patent No.: US 9,586,993 B2
(45) Date of Patent: *Mar. 7, 2017

(54) CD44V6-DERIVED PEPTIDES FOR TREATING PANCREATIC CANCER

(71) Applicant: AMCURE GMBH, Eggenstein-Leopoldshafen (DE)

(72) Inventors: Veronique Orian-Rousseau, Rittershoffen (FR); Alexandra Matzke, Dettenheim (DE); Helmut Ponta, Graben-Neudorf (DE)

(73) Assignee: AMCURE GMBH, Eggenstein-Leopoldshafen (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/407,244

(22) PCT Filed: Nov. 21, 2013

(86) PCT No.: PCT/EP2013/074401
§ 371 (c)(1),
(2) Date: Dec. 11, 2014

(87) PCT Pub. No.: WO2014/079940
PCT Pub. Date: May 30, 2014

(65) Prior Publication Data
US 2015/0166607 A1 Jun. 18, 2015

(30) Foreign Application Priority Data
Nov. 21, 2012 (GB) .................................. 1220901.1

(51) Int. Cl.
A61K 38/00 (2006.01)
C07K 7/06 (2006.01)
C07K 7/08 (2006.01)
A61K 38/17 (2006.01)

(52) U.S. Cl.
CPC .............. *C07K 7/08* (2013.01); *A61K 38/177* (2013.01); *C07K 7/06* (2013.01)

(58) Field of Classification Search
CPC ........... A61K 38/177; C07K 7/06; C07K 7/08
USPC ....................................................... 514/19.3
See application file for complete search history.

(56) References Cited

U.S. PATENT DOCUMENTS

2012/0115794 A1* 5/2012 Matzke .................. A61K 38/08
514/20.8
2012/0258998 A1 10/2012 Tan et al.

FOREIGN PATENT DOCUMENTS

| EP | 1258255 | 11/2002 |
|---|---|---|
| EP | 1391213 | 2/2004 |
| EP | 1417974 | 5/2004 |
| EP | 1647556 | 4/2006 |
| EP | 2218457 | 8/2010 |
| EP | 2266593 | 12/2010 |
| WO | WO97/16557 | 5/1997 |
| WO | WO00/44771 | 8/2000 |
| WO | WO2005/065709 | 7/2005 |
| WO | WO2007/121147 | 10/2007 |
| WO | WO2009/029847 | 3/2009 |
| WO | WO2011/022335 | 2/2011 |

OTHER PUBLICATIONS

Pancreatic Cancer from Merck Manual, pp. 1-5. Accessed Jan. 4, 2016.*
Kawano et al, "Evaluation of soluble adhesion molecules CD44 (CD44st, CD44v5, CD44v6), ICAM-1, and VCAM-1 as tumor markers in head and neck cancer," American Journal of Otolaryngology, 2005, 308-313.*
Alexandra Matzke et al., A Five-Amino-Acid Peptide Blocks Met- and Ron-Dependent Cell Migration, Cancer Research, Jul. 15, 2005, pp. 6105-6110.
M. Tremmel et al., A CD44v6 peptide reveals a rold of CD44 in VEGFR-2 signaling and angiogenesis, Blood, vol. 114, No. 25, Sep. 22, 2009, pp. 5236-5244.
Orian-Rousseau et al., CD44, a therapeutic target for metastasizing tumours, European Journal of Cancer, Pergamon Press, Oxford, GB, vol. 46, No. 7, May 1, 2010, pp. 1271-1277.
Hoffman M., et al., CD44 Splice Variants Confer Metastatic Behaviour in Rats: Homologous Sequences are Expressed in Human Tumor Cell Lines1, Cancer Research, American Association for Cancer Research, vol. 51, No. 19, Oct. 1, 1991, pp. 5292-5297.

* cited by examiner

*Primary Examiner* — Julie Ha
(74) *Attorney, Agent, or Firm* — Leason Ellis LLP

(57) ABSTRACT

Compounds, pharmaceutical compositions and methods for treating different forms of pancreatic cancer.

15 Claims, 22 Drawing Sheets
(12 of 22 Drawing Sheet(s) Filed in Color)

Figure 8

| Table 1 | | | | |
|---|---|---|---|---|
| cell line | primary tumor | metastasis lung | metastasis ln | micrometastasis |
| AS | 5/5 | 0/5 | 0/5 | 0/5 |
| ASs6 | 15/15 | 15/15 | 15/15 | |
| ASv1-v10Δv6 | 10/10 | 0/10 | 0/10 | 0/10 |
| ASv1-v10 | 10/10 | 10/10 | 10/10 | |
| ASs6 ctrl shRNA | 10/10 | 10/10 | 10/10 | |
| ASs6 Met shRNA | 10/10 | 0/10 | 0/10 | 0/10 |

| Table 2 | | | | |
|---|---|---|---|---|
| ASs6 +treatment | primary tumor | metastasis lung | metastasis ln | micrometastasis |
| CD44v6 Ab | 14/14 | 1/14 | 1/14 | 1/14 |
| CD44v6 pep i.t | 14/14 | 0/14 | 0/14 | 0/14 |
| CD44v6 pep i.v | 15/15 | 0/15 | 0/15 | 0/15 |
| ctrl pep | 15/15 | 15/15 | 15/15 | |
| PBS | 10/10 | 10/10 | 10/10 | |

| | Table 3 | | | |
|---|---|---|---|---|
| | BSp73ASs6 | | L3.6pl | |
| | primary tumor | lung metastasis | primary tumor | liver metastasis |
| control (3 weeks after tumor cell injection) | 10/10 | 10/10 | 10/10 | 10/10 |
| ctrl peptide treatment (3 more weeks) | 15/15 | 15/15 | 15/15 | 15/15 |
| v6 peptide treatment (3 more weeks) | 15/15 | 1/15 | 15/15 | 1/15 |

Figure 9
A
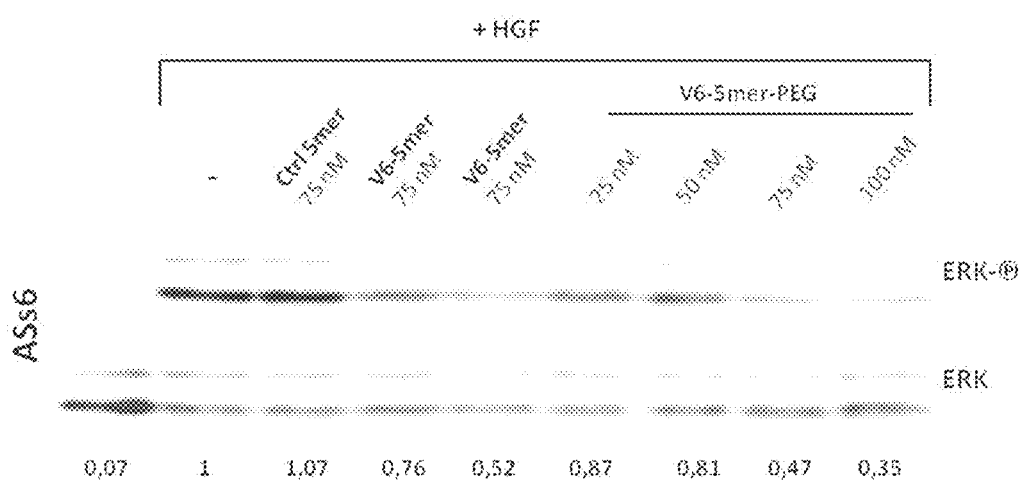
B
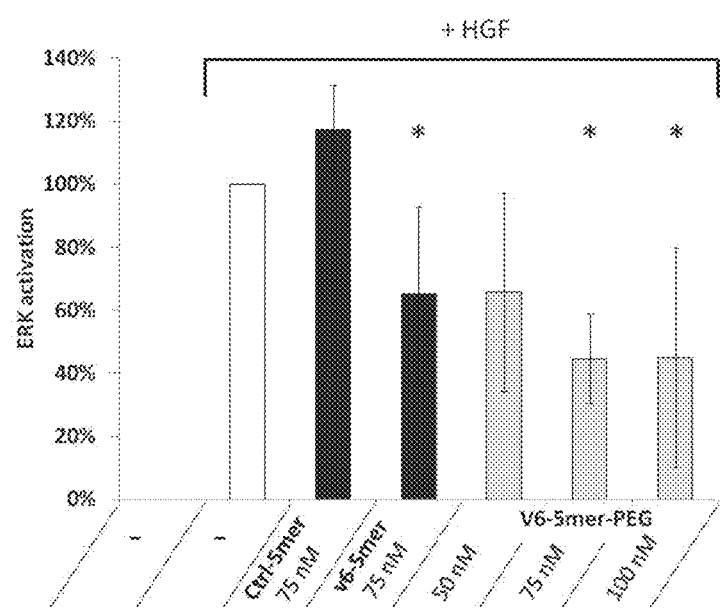

Figure 12
A
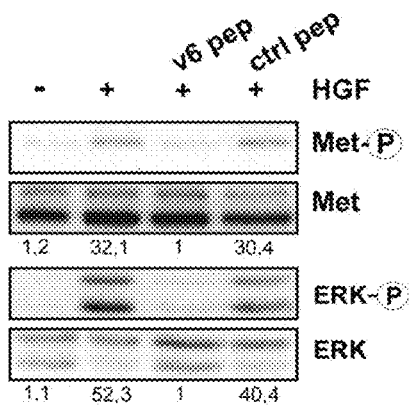
B
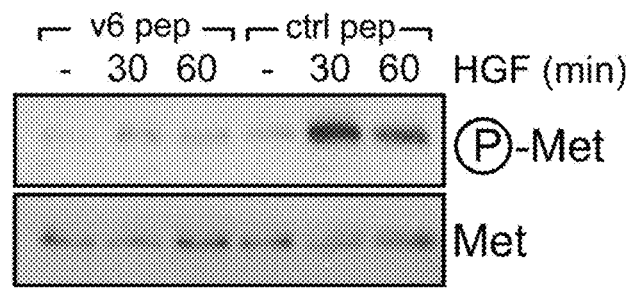
C
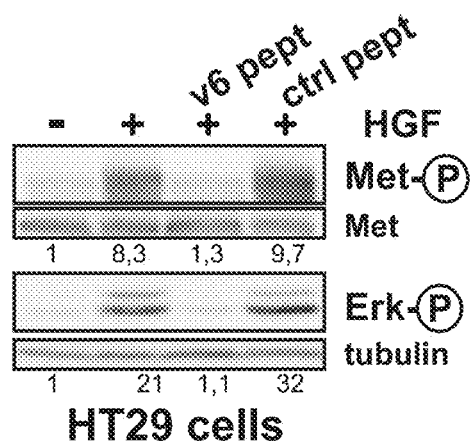

CD44V6-DERIVED PEPTIDES FOR TREATING PANCREATIC CANCER

CROSS-REFERENCE TO RELATED PATENT APPLICATIONS

This application is a U.S. National Phase Application under 35 U.S.C. §371 of International Patent Application No. PCT/EP2013/074401, filed Nov. 21, 2013, and claims priority to GB 1220901.1 filed Nov. 21, 2012, which is incorporated by reference in its entirety. The International Application was published on May 30, 2014, as International Publication No. WO 2014/079940.

TECHNICAL FIELD OF THE INVENTION

The present invention relates to compounds, pharmaceutical compositions and methods for treating different forms of pancreatic cancer.

BACKGROUND OF THE INVENTION

In the United States, pancreatic cancer is the second most common malignant tumor of the gastrointestinal tract and the fourth leading cause of cancer-related death in adults (Cancer Stating Manual, 7th Edition, 2010, American Joint Committee on Cancer, Springer). It is a malignant neoplasm originating from transformed cells arising in tissues forming the pancreas. The most common type of pancreatic cancer is adenocarcinoma or exocrine pancreatic cancer, which are tumors exhibiting glandular architecture on light microscopy arising with the exocrine component of the pancreas. A minor type arises from pancreatic duct cells and is classified as neuroendocrine tumors.

Treatment of pancreatic cancer typically depends on the stage of the cancer. Although only localized cancer is considered suitable for surgery with curative intent at present, only about 20% of cases are diagnosed with localized disease at diagnosis. Surgery can also be performed for palliation, if the malignancy is invading or compressing the duodenum or colon. Further treatment options include radiation and palliative chemotherapy. At present chemotherapy includes treatment with gemcitabin or combination therapies with gemcitabin such as gemcitabin/oxaliplatin or gemcitabin/cisplatin.

Despite intensive research efforts, no treatment is currently available which would be considered to provide a long-term progression-free survival. Pancreatic cancer is therefore to date one of the malignancies with the worst prognosis of all neoplasias. Particularly if metastases have spread across the body such as to the liver, the peritoneal cavity and the lungs, no efficient treatment is available, which would allow to effectively regression of existing metastases.

Thus, there is a need for new compounds and methods, which can be used to treat the different types of pancreatic cancer, in particular when metastatic spreading has occurred.

OBJECTIVE AND SUMMARY OF THE INVENTION

It is one objective of the present invention to provide compounds, and pharmaceutical compositions comprising such compounds, which can be used for the treatment of pancreatic cancer in a human being.

Another objective is to provide new methods for treating pancreatic cancer in a human being.

Another objective is to provide new compounds, pharmaceutical compositions and methods that allow treatment of pancreatic cancers, where metastases have already spread to different parts of the human body, such as the liver, the peritoneal cavity and the lungs, preferably by removing these already-formed metastasis.

These and other objectives as they will become apparent from the ensuing description are attained by the subject-matter of the independent claims. Some of the preferred embodiments of the present invention are mentioned in the dependent claims.

The present invention, to some extent, is based on the experimental data described hereinafter that in part aim to elucidate the molecular function of the co-receptor molecule CD44v6. The CD44 transmembrane glycoproteins form part of a large family of cell adhesion molecules (CAMs). It has been recognized that CD44 comprises alternatively spliced variants, some of which are involved in the process of metastasis through its activation of the receptor tyrosine kinase Met and VEGFR (see Matzke et al., *Cancer Res* (2005), 65(14) 6105-6109).

The experiment described hereinafter shows that an alternatively spliced version of CD44 comprising exon v6 (CD44v6) is responsible for inducing metastasis, e.g. in animal models of human pancreatic cancer.

The experiments described hereinafter further show that a peptide having as a minimal requirement the tri-peptide sequence R-W-H being embedded in a 5-amino acid peptide backbone such as N-R-W-H-E (SEQ ID NO: 2) is capable of blocking the formation of metastases in an animal model of human pancreatic cancer. Furthermore, the data described herein show that in an orthotopic model of a human pancreatic cancer in mice, these peptides also allow efficient regression of metastases that have already spread and formed across the body.

As already mentioned above it has been found that the peptides described herein are efficient not only for inhibiting metastasis but also for actually removing already formed metastases if the tri-peptide sequence R-W-H is embedded in a 5-amino acid peptide backbone. This was found by changing the amino acids N and E of the pentapeptide N-R-W-H-E (SEQ ID NO: 2) to A respectively (SEQ ID NO: 3). Even though these were non-conservative amino acid substitution, the peptide is still active in inhibiting CD44v6 mediated activation of Met. Thus, it seems justified to conclude that the N in the first position of the pentapeptide N-R-W-H-E (SEQ ID NO: 1) can not only be conservatively substituted by amino acids, such as K, R, or Q but also by any other amino acids or amino acids with non-polar side chains that are comparable to A such as V, L or I. The same considerations of course apply to the fifth position in the pentapeptide such that the amino acid E may not only be replaced by a conservative substitution, such as by K, but also by any other amino acid or particularly amino acids resembling the properties of alanine such as V, L or I.

Further, the pentapeptide N-R-W-H-E (SEQ ID NO: 2) has also been shown to be effective for inhibiting CD44v6-mediated activation of Met signaling when being embedded in a larger peptide, the upper limit of which is reasonably to assume being a 14 mer. Given the findings of the possibility to substitute the first and last position in the pentapeptide not only by conservative amino acid substitutions, but also by non-conservative amino acid substitutions, it seems reasonable to conclude that any amino acid outside the essential motive of R-W-H could be replaced according to the same reasoning.

Thus, the present invention in one embodiment thus relates to a compound for use in treating pancreatic cancer in a human being, wherein said compound comprises:

a peptide comprising at least the amino acid sequence $X_1$-R-W-H-$X_5$ (SEQ ID NO: 1) with $X_1$ being selected from the group comprising A, C, D, E, F, G, H, I, K, L, M, N, P, Q, R, S, T, V, W, or Y and $X_5$ being selected from the group comprising A, C, D, E, F, G, H, I, K, L, M, N, P, Q, R, S, T, V, W, or Y, or a peptidomimetic thereof, or a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 7), wherein $X_1$, $X_2$, $X_3$, $X_4$, $X_5$, $X_6$, $X_7$, $X_{11}$, $X_{12}$, $X_{13}$, or $X_{14}$ is selected from the group comprising A, C, D, E, F, G, H, I, K, L, M, N, P, Q, R, S, T, V, W, or Y, and wherein the peptide comprises at least $X_7$-R-W-H-$X_{11}$ of SEQ ID NO: 7, wherein $X_7$, and $X_{11}$ is selected from the group comprising A, C, D, E, F, G, H, I, K, L, M, N, P, Q, R, S, T, V, W, or Y, or a peptidomimetic thereof.

Given the observations described above, namely that the amino acid N and amino acid E in the pentapeptide N-R-W-H-E (SEQ ID NO: 2) can be replaced by alanine (SEQ ID NO: 3), it seems reasonable to assume that peptides that comprise in these positions either conservative amino acid substitutions or amino acid substitutions, which in terms of their physical chemical properties are comparable to alanine, such as V, L, or I will also provide the same activity as N-R-W-H-E (SEQ ID NO: 2). The same considerations apply to peptides derived from the 14 mer for positions that flank the essential tripeptide motive R-W-H.

Thus, in a preferred embodiment the present invention relates to a compound for use in treating pancreatic cancer in a human being, wherein the compound comprises:

a peptide comprising at least the amino acid sequence $X_1$-R-W-H-$X_5$ (SEQ ID NO: 4), wherein $X_1$ is selected from the group comprising amino acids with an $NH_2$ group such as K, R, N, or Q, or amino acids with non-polar side chains such as A, V, L or I and wherein $X_5$ is selected from the group comprising amino acids with negatively charged side chains such as E or D, or amino acids with non-polar side chains such as A, V, L or I or a peptidomimetic thereof, or a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 8), wherein $X_1$ is selected from the group comprising amino acids with an $NH_2$ group such as K, R, N, or Q, or amino acids with non-polar side chains such as A, V, L or I, wherein $X_2$ is selected from the group comprising amino acids with negatively charged side chains such as E or D, or amino acids with non-polar side chains such as A, V, L or I, wherein $X_3$ is selected from the group comprising amino acids with an $NH_2$ group such as K, R, N, or Q, or amino acids with non-polar side chains such as A, V, L or I, wherein $X_4$ is selected from the group comprising amino acids with non-polar or non-charged side chains and aromatic ring structures such as F, W, or Y, or amino acids with non-polar side chains such as A, V, L or I, wherein $X_5$ is selected from the group comprising amino acids with non-polar or non-charged side chains and aromatic rings structures such as F, W, or Y, or amino acids with non-polar side chains such as A, V, L or I, wherein $X_6$ is selected from the group comprising G or amino acids with non-polar side chains such as A, V, L or I, wherein $X_7$ is selected from the group comprising amino acids with an $NH_2$ group such as K, R, N, or Q, or amino acids with non-polar side chains such as A, V, L or I, wherein $X_{11}$ is selected from the group comprising amino acids with negatively charged side chains such as E or D, or amino acids with non-polar side chains such as A, V, L or I, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, or amino acids with non-polar side chains such as A, V, L or I, and wherein $X_{14}$ is selected from the group comprising amino acids with an $NH_2$ group such as K, R, N, or Q, or amino acids with non-polar side chains such as A, V, L or I, and wherein the peptide comprises at least $X_7$-R-W-H-$X_{11}$ of SEQ ID NO: 8, wherein $X_7$ is selected from the group comprising amino acids with an $NH_2$ group such as K, R, N, or Q, or amino acids with non-polar side chains such as A, V, L or I and wherein $X_{11}$ is selected from the group comprising amino acids with negatively charged side chains such as E or D, or amino acids with non-polar side chains such as A, V, L or I, or a peptidomimetic thereof.

Even though the pentapeptides or any longer peptide derived from the 14 mer as described hereinafter should be effective not only in preventing metastasis but actually removing already formed metastases in pancreatic cancer, a preferred embodiment of the present invention refers to the pentapeptide sequences described hereinafter, with a particular preferred embodiment focusing on the amino acid sequence N-R-W-H-E (SEQ ID NO:2).

A person skilled in the art will understand that any compound that provides for the same amino acids or at least the same overall configuration of the peptide as peptides described herein such as the pentapeptide of SEQ ID NO: 1 or SEQ ID NO: 2 will also be efficient in not only preventing formation of metastasis, but also removing already formed metastases in pancreatic cancer.

The invention therefore in some embodiments contemplates the use of peptidomimetics of any of the peptides described hereinafter particularly peptidomimetics of SEQ ID NO: 1, SEQ ID NO: 2, SEQ ID NO: 3 or SEQ ID NO: 4 or 5. These peptidomimetics will preferably have the same amino acids but an altered backbone which provides for the same overall configuration of the peptidomimetic as does the peptide itself, but which is e.g. more resistant to protease cleavage. Preferred peptidomimetics are e.g. isosteric peptoids, which comprise poly-N-substituted glycines in the peptide bonds of the backbone.

The present invention also considers further modified forms of the peptides and peptidomimetics described herein. Such modified peptides or peptidomimetics may comprise e.g. chemically or enzymatically attached modifications that render the peptides more stable, e.g. against protease degradation, that allow to provide the peptides or peptidomimetics as pharmaceutically acceptable salts, or which e.g. improve the biological properties of the peptides or peptidomimetics such as half-life. Such preferred modified forms of such peptides or peptidomimetics refer to pegylated, hesylated, pasylated, myristoylated, glycosylated, and/or cyclic forms of these peptides and peptidomimetics, and in particular peptides of SEQ ID NO:1, SEQ ID NO:2, SEQ ID NO:3, SEQ ID NO:4 and SEQ ID NO:5 or peptidomimetics of these sequences.

Such modified peptides or peptidomimetics are generally referred to, in the context of the present invention, as compounds or peptide compounds. These compounds or peptide compounds may be formulated for oral administration, e.g. by inhalation, for nasal administration, or administration by injection such as subcutaneous administration.

In one embodiment the present invention also relates to pharmaceutical compositions for use in treating pancreatic cancer in a human being wherein these pharmaceutical compositions comprise the compounds/peptide compounds as described above. These pharmaceutical compositions may comprise pharmaceutically acceptable excipients and may be formulated for oral administration such as by inhalation, nasal administration or administration by injection.

The present invention also refers to the use of such peptides, peptidomimetics thereof, or modified peptides and peptidomimetics in the manufacture of a medicament for use in treating pancreatic cancer in a human being.

Further, the invention relates to methods of treating pancreatic cancer in a human being by administering the peptides, peptidomimetics thereof or modified forms thereof, i.e. the compounds in accordance with the present invention, or pharmaceutical compositions comprising compounds in accordance with the present invention to a human being in need thereof.

The compounds in accordance with the present invention, i.e. the peptides, peptidomimetics thereof or modified forms thereof, the pharmaceutical compositions of the present invention, and the methods in accordance with the present invention are considered for treating pancreatic cancers, which have not yet formed metastases. In a preferred embodiment, however, the compounds, i.e. the peptides, peptidomimetics thereof and modified forms thereof, the pharmaceutical compositions in accordance with the invention, and the methods in accordance with the invention are considered to be used for treating pancreatic cancers where metastases have already formed and spread across the body. Thus, in a particularly preferred embodiment the present invention considers the compounds of the present invention, i.e. the peptides, peptidomimetics thereof or modified forms thereof, the pharmaceutical compositions described hereinafter and methods described hereinafter for treating pancreatic cancer in a human subject, for which the pancreatic cancer is classifiable as Stage IV according to the TNM Anatomic Stage/Prognostic Group System of the Cancer Staging Manual of the American Joint Committee on Cancer ($7^{th}$ edition, 2010, Springer).

It is to be understood that for all aspects and embodiments of the present invention, i.e. the compounds, pharmaceutical compositions and methods as described hereinafter, it is always preferred to use the pentapeptides as described herein, such as those of SEQ ID NO:1, SEQ ID NO:2; SEQ ID NO:3, SEQ ID NO:4 and SEQ ID NO:5 and in particular of SEQ ID NO:2 for treating pancreatic cancer in a human being, preferably in a situation where the pancreatic cancer has already formed metastases, and in particular for treating pancreatic cancers which are classifiable as Stage IV according to the TNM Anatomic Stage/Prognostic Group System of the Cancer Staging Manual of the American Joint Committee on Cancer ($7^{th}$ edition, 2010, Springer).

FIGURE LEGENDS

The patent or application file contains at least one drawing executed in color. Copies of this patent or patent application publication with color drawing(s) will be provided by the Office upon request and payment of the necessary fee.

FIG. 1: The co-receptor function of CD44v6 for Met is required for tumor metastasis. A: BSp73AS and its transfectants were induced with HGF where indicated and the activation of Met and ERK was determined as described in Materials and Methods. The numbers indicate the fold induction as calculated by the computer program ImageJ. All experiments were performed at least 3 times and gave similar results. B: The cells used in A were subcutaneously injected into the right posterior flank of syngeneic rats (Materials and Methods). Four weeks later the lymph nodes and lungs were prepared for immunohistochemical analysis. The represented lymph nodes are the auxiliary lymph nodes. Two pictures of the lungs are shown, the arrows indicate metastases C: Immunohistochemical analysis of paraffin sections of ASs6 tumors infected with lentivirus expressing ctrl-shRNA or Met-shRNA. Slices were stained with anti-GFP antibody to monitor shRNA-transduced areas or with a phospho-Met antibody. Magnification 20×.

FIG. 2: A CD44v6 specific peptide blocks metastatic spreading of tumor cells. A: BSp73ASs6 cells were induced with HGF in the presence of the CD44v6-specific rat peptide, a CD44v6 specific antibody or a control peptide (mouse) as indicated. The activation of Met and Erk was determined using phospho-specific antibodies. The numbers refer to the fold induction. B: BSp73ASs6 cells were injected subcutaneously into the right posterior flank of BD10 rats. After one week of tumor growth the animals were treated with the CD44v6 peptide (i.t. or i.v.), the control peptide, the CD44v6 antibody or PBS (Materials and Methods). Axillary lymph nodes (left side) and lungs (right side) were analyzed for metastases as described in FIG. 1. C: Sections of lungs of animals treated either with the CD44v6 peptide or with the control peptide were stained with H&E and PAS. H&E—hematoxylin and eosin; PAS—Periodic acid-Schiff reaction. Magnification 1.5×. D: Growth curve of BSp73ASs6 tumors in animals upon treatment for 28 days as indicated. The mean tumor volume of rats treated with either PBS, CD44v6 antibody, CD44v6 peptide or control peptide (mouse) was measured weekly after the start of the treatment and continued for 28 days using a caliper.

FIG. 3: Specific binding of the CD44v6 peptide to primary tumors and metastases in vivo. A: Left side: BSp73ASs6 cells were fixed and stained either with the DY681 labeled CD44v6 rat or the mouse peptide (control) for one hour. Images were taken using a laser scanning confocal microscope (Leica TCS2 SP2) with a 20× objective. Right side: BSp73ASs6 cells were induced with HGF in the presence of the DY681 rat v6 peptide respectively mouse peptide and the activation of Erk was determined. The numbers indicate fold induction. B: Rats bearing a subcutaneous tumor of BSp73ASs6 cells (grown for three weeks) were injected i.v with 200 μg of DY681 rat v6 peptide or DY681 mouse v6 peptide (control) and analyzed by NIRF imaging using Optix MX2 (ART, Montreal, Canada). Fluorescence intensities are displayed in NC (Normalized Correlation). Series of fluorescent data sets obtained at various time points after injection of the indicated peptide show fluorescent signals after 24 and 48 hours indicating binding of the rat v6 peptide but not the mouse v6 peptide in the range of two days to the tumor. C: Ex vivo scans of tumors and lungs from rats injected with DY681 rat v6 peptide showed specific fluorescent signals not only over the tumor area but also in specific areas of the lung indicating binding of the rat peptide to metastases.

FIG. 4: A CD44v6 peptide prevents metastasis of human tumor cells in an orthotopic model of pancreatic cancer. A: L3.6p1 cells were treated with the human v6 peptide or the rat v6 peptide as control prior to induction with 10 ng/ml HGF. Activation of ERK was determined in western blot. The numbers refer to the fold induction. B: L3.6p1 cells were injected orthotopically into the head of the pancreas of male nude mice (Materials and Methods). 7 days later the animals were injected with the human CD44v6 peptide or control (rat) peptide (20 μg each). The peptide injection was repeated 3 times per week. Animals were killed 23 days after the first peptide treatment. Tumors were isolated and stained for CD44v6 expression (BIWA) or secondary antibody as control. Nuclei were stained with hematoxylin. C: Immunofluorescence staining of L3.6p1 tumors from the v6 peptide or control peptide treated animals using the phospho-Met and Met antibodies. Nuclei are stained with DAPI. D top: Tumor volume of animals treated with either v6 or control peptide was determined at the end of the experiment using the formula volume=(width)2×length/2. Bars represent average tumor volume at the end of the experiment. D bottom: Each group of animals treated with one of the peptides consisted of 15 animals. Bars show the percentage of animals bearing metastases. E: Staining of L3.6p1 tumors treated with control or v6 peptide with a CD31-specific antibody. The magnification is 50×. The graphs show the average vessel numbers respectively average vessel size calculated from five independent tumors. F: Human VEGF levels produced by L3.6p1 cells in presence and absence of the v6 peptide (200 ng/ml in the culture medium). Bars reflect average VEGF levels from triplicates obtained in 3 independent experiments. G: Left side: Livers of v6 peptide or control peptide treated animals were examined for macroscopic metastases. Right side: Bars show the average number of metastases. Each group of animals treated with one of the peptides consisted of 15 animals. In all graphs the significance was calculated using Student's t test: ***p<0.001.

FIG. 5: Specific accumulation of the CD44v6 peptide in primary tumors and metastases of the human pancreatic cancer model. A: Left side: L3.6p1 cells were stained with either the DY681 labeled CD44v6 human or rat peptide. Images were taken with the laser scanning confocal microscope (Leica TCS2 SP2). Right side: L3.6p1 cells were induced with HGF in the presence of the DY681 human v6 peptide respectively rat v6 peptide and the activation of ERK was determined. The numbers refer to the fold induction. B: L3.6p1 tumors were orthotopically induced for 3 weeks as described in FIG. 4 followed by one intravenous injection of DY681 human v6 peptide or DY681 rat v6 peptide, (each 20 μg). Binding of the peptide was analyzed 24 h after injection in anesthetized mice using the Pearl® Impulse Small Animal Imaging System (Li-Cor). Tumor free and tumor bearing animals that received no peptide treatment were used as control. C: Primary tumors, livers and spleens were excised from the animals shown in B and fluorescence of the labeled peptides was monitored ex-vivo. The scales at the side indicate the synchronized signal intensity.

FIG. 6: Reversion of pre-existing metastases by the CD44v6 peptides. A: Schematic representation of the experimental procedure. BSp73ASs6 cells or L3.6p1 cells were injected in rats respectively nude mice. During the following 3 weeks, the tumors developed and metastases were detected after 3 weeks of time. In the groups treated with the v6 peptide or the control peptide (200 μg in rats, 20 μg in nude mice), the treatment started after three weeks. After 21 additional days the animals were sacrificed and analyzed for lung respectively liver metastases. B: Lungs of rats bearing a BSp73ASs6 subcutaneous tumor and treated with the v6 peptide (rat) or the control peptide (mouse) are shown. Bottom left: The quantification represents the average number of metastases. The number of animals used in each group is given in Table 3. Bottom right: A graphic evaluation of the number of animals bearing metastases is presented. C: Livers from mice with L3.6p1 pancreatic tumors and treated with the v6 peptide (human) or the control peptide (rat) are shown. Bottom left: A graph evaluating the number of liver metastases in control peptide treated animals and CD44v6 peptide treated animals is shown. Bottom right: A graphic evaluation of the number of animals bearing metastases is presented.

FIG. 7: The CD44v6 peptide induces apoptosis in already established metastases. Animals bearing lung metastases three weeks after tumor cell injection received an injection of CD44v6 peptide or control peptide every second day. At the indicated days one animal of each group was sacrificed. Apoptosis in lung metastasis was monitored on paraffin sections using an antibody against cleaved Caspase-3 and cleaved Caspase-8 (Materials and Methods). The area of the metastasis is marked (M). The magnification is 4.5×. The experiment was performed 2 times with similar outcome.

FIG. 8: depicts Tables 1 to 3.

FIG. 9: Parts A and B depict effects of pegylated rat CD44v6 peptides on activation of ERK in rat pancreatic cells.

FIG. 10: depicts effects of pegylated rat CD44v6 peptides on activation of ERK and Met in rat pancreatic cells.

FIG. 11: depicts effects of pegylated rat CD44v6 peptides on HGF induced clustering in colon cancer cells.

FIG. 12: A: Activation of Met and signal transduction induced by HGF depends on CD44v6 in L3.6p1 cells. L3.6p1 cells were treated with the human v6 peptide (human v6 14mer) or the rat v6 peptide as control prior to induction with 10 ng/ml HGF. Activation of Met and ERK was determined in western blot. The numbers refer to the fold induction. The experiment was repeated at least 5 times. B: Activation of c-Met and signal transduction induced by HGF depends on CD44v6 HeLa cells. Starved HeLa cells respectively HT29 cells were incubated with the v6 peptide (human v6 14mer) or a control peptide for 10 minutes at 37° C. and then induced with 25 ng/ml of HGF for the indicated time points. Cells were then either lysed and the lysates were subjected to Western Blot analysis for phospho-Met and Met. C: Activation of c-Met and signal transduction induced by HGF depends on CD44v6 in HT29 cells. HGF-induced c-Met and Erk phosphorylation in HT29 was determined as described above using phospho-specific antibodies. Where indicated the cells were pretreated with the CD44v6 peptide (human v6 14mer) or the control peptide (see Materials and Methods in Example 3). The loading controls were developed with c-Met respectively tubulin antibodies.

FIG. 13: In contrast to EGF and ER, induction of the ErbB-receptors via TGF-α, BC, Her, HB-EGF or AR is completely independent of CD44v6. Serum-starved HT29 cells were pre-incubated for 5 min with 100 ng/ml of a CD44v6-specific peptide (human v6 14mer) or a control peptide. Afterwards the cells were induced with 20 ng/ml of various ErbB ligands as indicated. The cell lysates were resolved by SDS-PAGE. Western-blotting was used to detect ErbB ligands-induced Erk-kinase phosphorylation.

FIG. 14: EGF-dependent induction of the ErbB receptors can be blocked by a CD44v6 specific peptide in HT29 cells. Serum-starved HT29 cells were pre-incubated for 5 min with 100 ng/ml of CD44v6-specific peptide (pep1=14mer, pep2=5mer) or a control peptide. Afterwards the cells were induced with 20 ng/ml of EGF or TGFα and lysed. The cell lysates were resolved by SDS-PAGE. Western-blotting was used to detect EGF and TGFα induced Erk-kinase phosphorylation.

FIG. 15: Inhibition of metastasis and primary tumor growth using the human v6 peptide and PEGylated derivatives thereof (PEG840 and PEG2000) at different concentrations (2 μg, 20 μg and 200 μg per injection). A: L3.6p1 tumors were orthotopically implanted in nude mice for one week, followed by i.p. injection of the indicated peptides three times per week for three weeks. At the end of the experiment animals were sacrificed and examined Red arrows indicate metastases. Significance was calculated using Student's t test: ***$p<0.001$. Each group consisted of 3 animals. B: Quantification of the primary tumor volume. C: Overview of the average number of macrometastases per animal.

FIG. 16: Inhibition of metastasis and primary tumor growth using the CD44v6 peptide (linear 14mer) and a human cyclic 8mer at different concentrations (0, 2 μg, 2 μg, 10 μg and 20 μg per injection). A: L3.6p1 tumors were orthotopically implanted in nude mice for one week, followed by i.p. injection of the indicated peptides three times per week for three weeks. At the end of the experiment, animals were sacrificed and examined Red arrows indicate metastases. Significance was calculated using Student's t test: * $p<0.01$, ***$p<0.001$. Each group consisted of 5 animals. B: Overview of average number of macroscopic metastases in each animal. C showed a decrease in metastatic spreading starting from a dosage of 2 μg and full inhibition at 20 μg. C: The v6 14mer and the cyclic 8mer reduces growth of the primary tumor.

FIG. 17: Side-by-side comparison of the v6 14mer with derivatives thereof (14merPEG840, 14mer PEG2000, myristoylated 14mer, D-amino acid derivatives DOTA CD44v6-14[daa7] and DOTA CD44v6-14[r14], cyclic 8mer, cyclic 5mer and myristoylated cyclic 8mer) for primary tumor growth. L3.6p1 tumors were orthotopically implanted in nude mice for one week, followed by i.p. injection of the indicated peptides three times per week for three weeks. At the end of the experiment animals were sacrificed and examined A: Average tumor size of animals treated with the indicated compounds (n=5) is shown. Significance was calculated using Student's t test: ***$p<0.001$. Each group consisted of 5 animals. B: Individual tumor size of animals in each group.

FIG. 18: Side-by-side comparison of the v6 14mer with derivatives thereof (14merPEG840, 14mer PEG2000, myristoylated 14mer, D-amino acid derivatives DOTA CD44v6-14[daa7] and DOTA CD44v6-14[r14], cyclic 8mer, cyclic 5mer and myristoylated cyclic 8mer) for inhibition of metastasis. A: Representative examples of primary tumor and liver metastasis for the indicated compounds. Red arrows point towards a metastase. Red circle: Note the very strong vascularization of the primary tumor in the control group. B: Summary of the number of animals with metastasis and the average number of metastases per animal.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

For the purposes of the present invention, the term "obtained" is considered to be a preferred embodiment of the term "obtainable". If hereinafter e.g. an antibody is defined to be obtainable from a specific source, this is also to be understood to disclose an antibody, which is obtained from this source.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±20%, preferably ±15%, more preferably ±10%, and even more preferably ±5%.

Furthermore, the terms "first", "second", "third" or "(a)", "(b)", "(c)", "(d)" or "(i)", "(ii)", "(iii)", "(iv)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" or "(i)", "(ii)", "(iii)", "(iv)" etc. relate to steps of a method or use or assay there is no time or time interval coherence between the steps unless indicated otherwise, i.e. the steps may be carried out simultaneously or there may be time intervals of seconds, minutes, hours, days, weeks, months or even years between such steps, unless otherwise indicated in the application as set forth herein above or below.

Technical terms are used by their common sense. If a specific meaning is conveyed to certain terms, definitions of terms will be given in the following in the context of which the terms are used.

As mentioned above, the present invention is concerned with peptides or peptide compounds for use in treating pancreatic cancer in a human being.

The present invention is based to some extent on the experimental findings described hereinafter that a peptide of amino acid sequence N-R-W-H-E (SEQ ID NO: 2) is not only capable of inhibiting metastasis in human pancreatic cancer cells but can also eliminate already established metastases in an orthotropic animal model of human pancreatic cancer. It was moreover shown that upon mutating N to A and E to A, a peptide of amino acid sequence A-R-W-H-A (SEQ ID NO: 3) is capable of abrogating Met activation (see Matzke et al., *Cancer Res.* (2005), 65 (14), 6105-6110).

Given that the effects on Met activation by N-R-W-H-E (SEQ ID NO: 2) are maintained despite the non-conservative amino acids substitutions of K to A and F to A (Matzke et al., vide supra), it seems reasonable to assume that a peptide of amino acid sequence $X_1$-R-W-H-$X_5$ (SEQ ID NO: 1), wherein $X_1$ is selected from the group comprising A, C, D, E, F, G, H, I, K, L, M, N, P, Q, R, S, T, V, W, or Y and wherein $X_5$ is selected from the group comprising A, C, D, E, F, G, H, I, K, L, M, N, P, Q, R, S, T, V, W, or Y can also be used for treatment of pancreatic cancer in a human being.

The present invention thus in one embodiment relates to a compound for use in treating pancreatic cancer in a human being, wherein said compound comprises a peptide comprising at least the amino acid sequence $X_1$-R-W-H-$X_5$ (SEQ ID NO: 1) wherein $X_1$ is selected from the group comprising A, C, D, E, F, G, H, I, K, L, M, N, P, Q, R, S, T, V, W, or Y and wherein $X_5$ is selected from the group comprising A, C, D, E, F, G, H, I, K, L, M, N, P, Q, R, S, T, V, W, or Y or a peptidomimetic thereof.

Preferably, the present invention in one embodiment relates to a compound for use in treating pancreatic cancer in a human being, wherein said compound comprises a peptide comprising at least the amino acid sequence $X_1$-R-W-H-$X_5$ (SEQ ID NO: 4) wherein $X_1$ is selected from the group comprising amino acids with an $NH_2$ group such as K, R, N, or Q, or amino acids with non-polar side chains such as A, V, L or I and wherein $X_5$ is selected from the group comprising amino acids with negatively charged side chains such as E or D, or amino acids with non-polar side chains such as A, V, L or I or a peptidomimetic thereof. An example is a peptide of amino acid sequence A-R-W-H-A (SEQ ID NO: 3) or a peptidomimetic thereof.

Even more preferably, the present invention in one embodiment relates to a compound for use in treating pancreatic cancer in a human being, wherein said compound comprises a peptide comprising at least the amino acid sequence $X_1$-R-W-H-$X_5$ (SEQ ID NO: 5), wherein $X_1$ is selected from the group comprising K, R, N, or Q and wherein $X_5$ is selected from the group comprising E or D. As an example of one of the most preferred embodiments the peptide may comprise and preferably consist of amino acid sequence N-R-W-H-E (SEQ ID NO: 2).

The term "peptide" as used herein refers to any compound comprising at least the above mentioned amino acids five and a maximum of fourteen amino acids.

If peptides in accordance with the invention have more than the above-mentioned five amino acids, these amino acids may e.g. be those found in a peptide of amino acid sequence K-E-Q-W-F-G-N-R-W-H-E-G-Y-R (SEQ ID NO: 6) or variations thereof. It is noted that amino acids 7 to 11 of SEQ ID NO: 6 correspond to SEQ ID NO: 2. As for a peptide of SEQ ID NO: 2, it has been found in a linker screen analysis with alanine substitutions that amino acids 1, 2, 3, 4, 5, 6, 12, 13, or 14 can be substituted by alanine without having detrimental effects on Met activation. Such peptides may thus be any peptide comprising amino acids 6 to 12, 5 to 13, 4 to 14, etc. of $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 7), wherein $X_1$ is selected from the group comprising A, C, D, E, F, G, H, I, K, L, M, N, P, Q, R, S, T, V, W, or Y, wherein $X_2$ is selected from the group comprising A, C, D, E, F, G, H, I, K, L, M, N, P, Q, R, S, T, V, W, or Y, $X_3$ is selected from the group comprising A, C, D, E, F, G, H, I, K, L, M, N, P, Q, R, S, T, V, W, or Y, $X_4$ is selected from the group comprising A, C, D, E, F, G, H, I, K, L, M, N, P, Q, R, S, T, V, W, or Y, $X_5$ is selected from the group comprising A, C, D, E, F, G, H, I, K, L, M, N, P, Q, R, S, T, V, W, or Y, $X_6$ is selected from the group comprising A, C, D, E, F, G, H, I, K, L, M, N, P, Q, R, S, T, V, W, or Y, $X_7$ is selected from the group comprising A, C, D, E, F, G, H, I, K, L, M, N, P, Q, R, S, T, V, W, or Y, $X_{11}$ is selected from the group comprising A, C, D, E, F, G, H, I, K, L, M, N, P, Q, R, S, T, V, W, or Y, $X_{12}$ is selected from the group comprising A, C, D, E, F, G, H, I, K, L, M, N, P, Q, R, S, T, V, W, or Y, $X_{13}$ is selected from the group comprising A, C, D, E, F, G, H, I, K, L, M, N, P, Q, R, S, T, V, W, or Y and wherein $X_{14}$ is selected from the group comprising A, C, D, E, F, G, H, I, K, L, M, N, P, Q, R, S, T, V, W, or Y. Preferably the selection is made according to the principles laid out above. Thus, $X_1$ may either be an amino acid similar to K or it may be an amino acid with a non-polar side chain such as A, V, L, or I. Similar considerations apply to $X_2$, $X_3$, $X_4$, $X_5$, $X_6$, $X_7$, $X_{11}$, $X_{12}$, $X_{13}$ or $X_{14}$. In one preferred embodiment such longer peptide comprise amino acids 6 to 12, 5 to 13, 4 to 14, etc. of $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 8), wherein $X_1$ is selected from the group comprising amino acids with an $NH_2$ group such as K, R, N, or Q, or amino acids with non-polar side chains such as A, V, L or I, wherein $X_2$ is selected from the group comprising amino acids with negatively charged side chains such as E or D, or amino acids with non-polar side chains such as A, V, L or I, wherein $X_3$ is selected from the group comprising amino acids with an $NH_2$ group such as K, R, N, or Q, or amino acids with non-polar side chains such as A, V, L or I, wherein $X_4$ is selected from the group comprising amino acids with non-polar or non-charged side chains and aromatic rings structures such as F, W, or Y, or amino acids with non-polar side chains such as A, V, L or I, wherein $X_5$ is selected from the group comprising amino acids with non-polar or non-charged side chains and aromatic rings structures such as F, W, or Y, or amino acids with non-polar side chains such as A, V, L or I, wherein $X_6$ is selected from the group comprising G or amino acids with non-polar side chains such as A, V, L or I, wherein $X_7$ is selected from the group comprising amino acids with an $NH_2$ group such as K, R, N, or Q, or amino acids with non-polar side chains such as A, V, L or I, wherein $X_{11}$ is selected from the group comprising amino acids with negatively charged side chains such as E or D, or amino acids with non-polar side chains such as A, V, L or I, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, or amino acids with non-polar side chains such as A, V, L or I, and wherein $X_{14}$ is selected from the group comprising amino acids with an $NH_2$ group such as K, R, N, or Q, or amino acids with non-polar side chains such as A, V, L or I. In an even more preferred embodiment such longer peptide comprise amino acids 6 to 12, 5 to 13, 4 to 14, etc. of $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 9), wherein $X_1$ is selected from the group comprising amino acids with an $NH_2$ group such as K, R, N, or Q, wherein $X_2$ is selected from the group comprising amino acids with negatively charged side chains such as E or D, wherein $X_3$ is selected from the group comprising amino acids with an $NH_2$ group such as K, R, N, or Q, wherein $X_4$ is selected from the group comprising amino acids with non-polar or non-charged side chains and aromatic rings structures such as F, W, or Y, wherein $X_5$ is selected from the group comprising amino acids with non-polar or non-charged side chains and aromatic rings structures such as F, W, or Y, wherein $X_6$ is selected from the group comprising G or amino acids with non-polar side chains such as A, V, L or I, wherein $X_7$ is selected from the group comprising amino acids with an NH$_2$ group such as K, R, N, or Q, X$_{11}$ is selected from the group comprising amino acids with negatively charged side chains such as E or D, wherein X$_{12}$ is selected from the group comprising G or amino acids with non-polar side chains such as A, V, L or I, wherein X$_{13}$ is selected from the group comprising amino acids with non-polar or non-charged side chains and aromatic rings structures such as F, W, or Y, and wherein X$_{14}$ is selected from the group comprising amino acids with an NH$_2$ group such as K, R, N, or Q.

Peptides may be linear, branched and they may be cyclic, with or without branching. Cyclic, branched and branched cyclic peptides may result from post-translation natural processes or may be made by synthetic methods.

In some of the most preferred embodiments, peptides in accordance with the invention comprise and more preferably consist of five or 14 amino acids as mentioned above and include peptides of SEQ ID NO: 1, 2, 3, 4, 5 or 6 to 10. The most preferred embodiment of the present invention relates to a peptide of SEQ ID NO: 2 or SEQ ID NO: 6.

The term "compound comprising a peptide" refers to compounds which comprise a peptide e.g. in the form of a pharmaceutically acceptable salt. The term equally refer to peptides which have been e.g. chemically or enzymatically modified such that e.g. a peptide of SEQ ID NO: 1, 2, 3, 4 or 5 comprises additional modifications as they are described hereinafter. Modified forms of a peptide of SEQ ID NO: 2 are particularly preferred.

The term "compound comprising a peptide" and its grammatical variation such as "peptide compound" thus includes salts, preferably pharmaceutically acceptable salts of the peptides described herein. Salts encompassed within the term "pharmaceutically acceptable salts" refer to non-toxic salts of the peptide compounds of this invention. Representative salts and esters include the following: acetate, ascorbate, benzenesulfonate, benzoate, bicarbonate, bisulfate, bitartrate, borate, camsylate, carbonate, citrate, dihydrochloride, methanesulfonate, ethanesulfonate, p-toluenesulfonate, cyclohexylsulfamate, quinate, edetate, edisylate, estolate, esylate, fumarate, gluconate, glutamate, glycerophosphates, hydrobromide, hydrochloride, hydroxynaphthoate, lactate, lactobionate, laurate, malate, maleate, mandelate, mesylate, mucate, napsylate, nitrate, n-methylglucamine, oleate, oxalate, palmoates, pamoate (embonate), palmitate, pantothenate, perchlorates, phosphate/diphosphate, polygalacturonate, salicylates, stearate, succinates, sulfate, sulfamate, subacetate, succinate, tannate, tartrate, tosylate, trifluoroacetate, and valerate. Other salts include Ca, Li, Mg, Na, and K salts; salts of amino acids such as lysine or arginine; guanidine, diethanolamine or choline; ammonium, substituted ammonium salts or aluminum salts. The salts are prepared by conventional methods.

The peptide component of "compound comprising a peptide" may, however, in addition to the peptide sequence of any of SEQ ID NOs: 1 to 9 comprise amino acid sequences derived from other proteins. Therefore, the peptide compound of the invention includes heterologous fusion peptides consisting essentially of SEQ ID NOs: 1 to 9 fused to a heterologous amino acid sequence. The heterologous amino acid sequence may comprise or consist of 1, 2, 3, 4 or more amino acids. The heterologous amino acid sequence may for example comprise or consist of at least 5 or at least 10 or at least 20 heterologous amino acids. The heterologous amino acids may be fused to the N- and/or C-terminus of the CD44-derived sequences SEQ ID NOs: 1 to 9 to provide other functionalities such as improved translocation across cellular membranes.

It is preferred that the peptide component of the invention is an isolated peptide. The term "isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

It is also preferred that the peptide of the invention is in a pure state. Preferably, the peptide is ≥80% pure, preferably ≥90% pure, more preferably ≥95% pure, even more preferably ≥99% pure and particularly preferred is a pharmaceutically pure state that is greater than 99.9% pure with respect to contaminating macromolecules, particularly other peptides. It is preferred that the peptide is free of infectious and pyrogenic agents.

Preferably, a purified peptide is substantially free of other peptides. When used in this context, the term "pure" does not exclude the presence of the same peptide in alternative physical forms, such as dimers.

The peptides of the invention may be prepared by chemical synthesis or by recombinant expression in host cells. The preparation by chemical synthesis is preferred. As protein products, compounds of e.g. SEQ ID NO: 2 or any of the other peptides of the present invention are amenable to production by the technique of solution- or solid-phase peptide synthesis. The synthetic peptide synthesis approach generally entails the use of automated synthesizers and appropriate resin as solid phase, to which is attached the C-terminal amino acid of the desired peptide. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, "Solid Phase Peptide Synthesis," 2nd Edition, Pierce Chemical Company, Rockford, Ill. (1984).

The term "peptidomimetic" refers to a small protein-like chain designed to mimic a corresponding peptide. Peptidomimetics can typically arise either from modification of an existing peptide, or by designing similar systems that mimic peptides, such as peptoids and β-peptides. Irrespective of the approach, the altered chemical structure is designed to advantageously adjust the molecular properties such as metabolic stability and bioavailability without negatively affecting biological activity.

Typically a peptidomimetic will have an altered backbone such as a methylated amide group instead of the amide group of a peptide bond to increase the stability of the peptidomimetic against degradation by proteases. Alternatively or in addition, the peptidomimetic may comprise non-natural amino acids or D-enantiomers. A common theme of peptidomimetics is that the molecular chains in the backbone structure and/or in the amino acids should not have a substantial effect on the overall conformation of the peptidomimetic in comparison to the corresponding peptide in order to not negatively affect the biological activity of the peptidomimetic. Thus a peptidomimetic is an isostere of the corresponding peptide. Preferred peptidomimetics are e.g. isosteric peptoids, which comprise poly-N-substituted glycines in the peptide bonds of the backbone. In accordance with the invention, peptidomimetic shall therefore have the same activity in the experiments described hereinafter as the peptides as described hereinafter, such as e.g. a peptide of SEQ ID NO: 1, 2, 3, 4, or 5. The most preferred peptidomimetics are those having five amino acids such as a peptidomimetic of a peptide of SEQ ID NO: 2, 8 amino acids (such as a peptidomimetic of SEQ ID NO: 16, 17 or 18) or 14 amino acids (cf. SEQ ID NO: 6, 7, 8, 9, or 10). Such peptidomimetics are preferably isosteric peptoids, which comprise poly-N-substituted glycines in the peptide bonds of the backbone.

The present invention also contemplates the use of modified forms of peptides or peptidomimetics, e. g. as pharmaceutical compositions for treating pancreatic cancer in a human being. Such modified forms relate e.g. to peptides or peptidomimetics which have been chemically modified at their respective N- and/or C-terminus by blocking groups such as FMOC or BOC or alkylation such as methylation to reduce degradation of the peptides or peptidomimetics e.g. by proteases and to increase stability thereof. Other modifications include acetylating, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, i.e. a cyclic peptide, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, including a myristoylated cyclic peptide, such as a myristoylated cyclic 5mer (based on SEQ ID NO: 2), 6mer, 8mer or 14mer, oxidation, proteolytic processing, phosphorylation, prenylation, racemization, selenoylation, sulfation, transfer-RNA mediated addition of amino acids to proteins such as arginylation, ubiquitination and sumoylation. Examples of such peptidomimetics are given in Table 4. In a preferred embodiment the peptide of the invention is a 14mer pegylated with PEG having a molecular weight of 2000 Da or a PEG having a molecular weight in the range of 200 to 20000 Da, a 14mer, a cyclic 8mer or a cyclic 5mer. A typical peptidomimetic can have one or more modification, i.e. can be cyclic and additionally be myristoylated, pegylated, and/or modified in any other way described herein, such as by use of D-amino acids. Typical examples of peptidomimetics include those which have SEQ ID NOs: 1 to 18 with L- and/or D-amino acids.

Cyclization of peptides is performed by methods generally known by a person skilled in the art, such as described in Zitzmann et al. (2005, *Journal of Nuclear Medicine*, 46(5):782).

The compounds of the invention can also be administered in combination with cytotoxic compounds and/or chemotherapeutic agents. It is possible to administer the compounds of the invention along with one or more cytotoxic compounds and/or chemotherapeutic agents or it is possible to covalently conjugate the cytotoxic compound to the peptide or compound of the invention. The preferred cytotoxic compounds are maytansinoids and preferred chemotherapeutic compounds are taxanes.

In addition or alternatively preferred modified forms of peptides or peptidomimetics in accordance with the invention include e.g. chemically or enzymatically modified forms thereof which have improved biological properties such as improved solubility, absorption, biological half-life, etc. The modifications may alternatively decrease the toxicity of the molecule, eliminate or attenuate any undesirable side effect of the molecule, etc. Modifications which increase e.g. the biological half-life include pegylation, hesylation, pasylation, glycosylation with glycosyl structure having sialic acid residues at their end, etc.

The terms "pegylated" and its grammatical variations such as "pegylation" all describe that the peptide or peptidomimetics thereof in their different forms (e.g. in isolated form, as pharmaceutically acceptable salts etc) comprise a PEG moiety, i.e. a polyethyleneglycol chain, which is covalently attached to the peptides or peptidomimetics as described herein.

As is described hereinafter, a rat CD44v6 pentapeptide of sequence NEWQG (SEQ ID NO: 11), which is the counterpart to the human CD44v6 pentapeptide of SEQ ID NO: 2 and which has been modified with PEG750 or PEG3000 is capable of inhibiting HGF stimulated and CD44 mediated activation of Met and Erk even though at least the PEG3000 moiety has a molecular weight, i.e. 3000 Da, which is significantly higher than the calculated molecular weight of the sequence of SEQ ID NO: 11, being approximately 620 Da. Moreover, PEGs of such a molecular weight are known to have an extended zigzag structure. It therefore is surprising that modification of comparatively small peptide such as the pentapeptide of SEQ ID NO: 11 does not lead to loss of activity. It seems justified to conclude that the same should apply to the human counterparts such as a pentapeptide of SEQ ID NO: 2, peptidomimetics thereof or even longer peptides such as those of SEQ ID NO: 6. It is furthermore surprising that inhibition of ERK signaling is even more efficient with pegylated peptides than non-pegylated peptides.

The term "PEG moiety" or "Polyethylenglycol moiety" as used hereinafter refers to PEGs of an average molecular weight of about 200 Da to about 35,000,000 Da. It is preferred to use PEGs which have an average molecular weight of about 400 Da to about 20,000 Da, preferably of about 600 to about 10,000 Da, even more preferably of about 700 Da to about 10,000 Da. The most preferred PEGs have an average molecular weight of about 800 Da to about 8,000 Da, of about 900 Da to about 7,000 Da, of about 1,000 Da to about 6,000 Da such as of about 2,000 Da, of about 3,000 Da, of about 4,000 Da or of about 5,000 Da. In a preferred embodiment, the PEG has an average molecular weight in the range of 200 to 20000 Da.

PEGs are typically named by their average molecular weight. Thus, a PEG with nine repeating units has an average molecular weight of 400 Da and would be labeled as PEG 400. The PEGs contemplated for the present invention may thus be PEGs such as PEG 400, PEG 600, PEG 50, PEG 840, PEG 1000, PEG 1500, PEG 2000, PEG 3000, PEG 3350, PEG 4000, PEG 4600, PEG 8000, PEG 10000, PEG 12000 as they are commercially available e.g. from Sigma-Aldrich.

PEGs may come as straight, branched, star or comb PEGs. Branched PEGs have three to ten PEG chains emanating from a central core group. Star PEGs have 10 to 100 PEG chains emanating from a central core group. Comb PEGs have multiple PEG chains normally grafted onto a polymer backbone.

For the purposes of the invention it is generally preferred to use straight PEGs and particularly preferred to use straight PEGs with an average molecular weight in the range of about 1,000 to 6,000 Da, such as a PEG 2000, PEG 3000, PEG 4000 or PEG 5000 or a PEG of higher molecular weight.

The PEG moieties may be further modified. For example, the PEG moieties may be covalently modified with fatty alcohol and fatty acids. Such additional modifications may allow the modified pegylated peptides and peptidomimetics to build or be at least incorporated in micelle- or liposome-like structures.

The present invention also relates to such micelle- or liposome-like structures. The pegylated peptides or pegylated peptidomimetics thereof and pharmaceutical compositions comprising such pegylated peptides or pegylated peptidomimetics thereof may provide e.g. for improved drug solubility, reduced dosage frequency, extended circulating half-life, increased drug stability, enhanced protection from proteolytic degradation, etc. The micelle- or liposome-like structures may additionally allow delivering the pegylated peptides or pegylated peptidomimetics more efficiently as the additional modification such as fatty alcohol- or fatty acid-chains may allow improved interaction with cellular membranes. Moreover, the micelle- or liposome-like structures may comprise additional pharmaceutically active agents such as chemotherapeutic agents. In case of pancreatic cancer, these agents may include e.g. gencitabin.

The present invention also relates to such micelle- or liposome-like structures comprising additional pharmaceutically active agents. Such micelle- or liposome-like structures will allow targeting of such chemotherapeutic agents through the pegylated peptides or pegylated peptidomimetics thereof to e.g. the tumors expressing CD44v6 and thus allowing targeted and improved therapy.

The person skilled in the art knows how to modify peptides or peptidomimetics with PEG moieties. The covalent attachment of a PEG moiety may be done chemically or enzymatically.

The first step in chemical modification is typically functionalizing either one or both ends of the PEG polymer. Depending on the fictionalization, one can differentiate between monofunctional, bihomofunctional or biheterofunctional PEGs.

The chemical Pegylation process can be generally categorized into two types, namely a solution phase batch process or an on-column fed-batch process. The commonly adopted batch process involves the mixing of reagents in a suitable buffer solution, preferably at a temperature of 4 to 6° C., followed by separation and purification of the desired product using techniques such as size exclusion chromatography, ion exchange chromatography or hydrophobic interaction chromatography.

The choice of the suitable functional group for the PEG derivative is based on the type of available reactive group on the molecule that will be coupled to the PEG. For proteins and peptides, typical reactive amino acids include lysine, cysteine, histidine, arginine, aspartic acid, glutamic acid, serine, threonine, tyrosine. The N-terminal amino group and the C-terminal carboxylic acid can also be used as a site specific site by conjugation with aldehydes functional polymers. If it is preferred to not react an amino acid with a PEG, but only e.g. the N-terminus of a peptide, one can block the functional groups in amino acids, e.g. with FMOC, pegylate the peptide and then de-block the amino acids.

The techniques used to form PEG derivatives such pegylated peptides are generally reacting the PEG polymer with a group that is reactive with hydroxyl groups, typically anhydrides, acid chlorides, chloroformates and carbonates. In the second generation Pegylation chemistry more efficient functional groups such as aldehyde, esters, amides etc. made available for conjugation.

Heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters.

The pegylated peptides and pegylated peptidomimetics thereof in accordance with the invention may be provided in the form of pharmaceutical compositions comprising optionally pharmaceutically acceptable excipients.

In the following it is set out how the compounds in accordance with the present invention, i.e. the peptides, peptidomimetics thereof and modified forms thereof, the pharmaceutical compositions comprising these compounds and methods making use of these compounds may be used for the treatment of pancreatic cancer in a human being. It is to be understood that, whenever reference is made in the following to the treatment of pancreatic cancer, this reference, as a preferred embodiment, always contemplates to use the pentapeptides as described hereinafter, namely those of SEQ ID NO: 1, SEQ ID NO:2, SEQ ID NO:3, SEQ ID NO:4 and SEQ ID NO:5, and in particular those of SEQ ID NO: 2, peptidomimetics thereof, or modified forms thereof.

Pancreatic cancers are commonly classified as exocrine pancreatic cancers, namely adenocarcinomas, and neuroendocrine pancreatic tumors. Of these, neuroendocrine carcinomas apply to about 3 to 5% of pancreatic malignancies (see Cancer Staging Manual, 7$^{th}$ edition, 2010, American Joint Committee on Cancer, Springer, 243-251). It is considered that the compounds, pharmaceutical compositions and methods as described hereinafter can be used for the treatment of both types of pancreatic cancer.

As can be taken from the experiments described hereinafter, the peptides used in the experiments were capable of inhibiting metastasis formation in pancreatic cancer models. Thus, the invention in one aspect relates to the use of compounds, pharmaceutical compositions and the application of methods as described herein for the treatment of pancreatic cancers, in which no metastases have yet formed.

Such cancers may be classified as Stage 0, Stage IA, Stage IB, Stage 2A, Stage 2B, or Stage 3 according to the Anatomical Stage/Prognostic Group System as described in the Cancer Staging Manual of the American Joint Committee on Cancer (Cancer Staging Manual of the American Joint Committee on Cancer, 2001, Springer, 243-251). If reference is made herein to Stages and the TNM classification system, this always refers to the staging system and the Anatomic stage/Prognostic groups system as described in the Cancer Staging Manual of the American Joint Committee on Cancer, 7th Edition, 2010, Springer, page 243 to 251) for pancreatic cancers.

To the extent that the present invention considers treatment of cancer in which no metastases have yet formed, the present invention in a preferred aspect considers treatment of Stage IIB, and even more preferably of Stage III, the reason being that particularly for Stage III it cannot be excluded that metastases have already started to form, even though they may not be detectable yet. For the treatment of pancreatic cancers according to Stage III, administration of compounds, pharmaceutical compositions or application of methods as described herein would thus allow not only prevention of the formation of metastases, but also to remove metastases that have already begun to form even though they may not be detectable yet.

The most preferred embodiment of the present invention refers to the use of compounds, i.e. peptides, peptidomimetics thereof and modified forms thereof as described hereinafter, pharmaceutical compositions comprising these compounds and the application of methods as described herein in treating pancreatic cancer in a human being, where metastases have already formed and spread across the human body. Such cancers may preferably be classifiable as Stage IV according to the Cancer Staging Manual of the American Joint Committee on Cancer.

Thus, if reference is made to the treatment of human pancreatic cancer of Stage IV, this implies that a cancer is treated for which metastases are detected across the human body. Currently no treatment, except for palliative chemotherapy, are available that would allow selective addressing of this type of cancer.

A particularly preferred embodiment thus refers to the use of the pentapeptides described hereinafter, e.g. of SEQ ID NO:1, 2, 3, 4, or 5 and most preferably of SEQ ID NO:2, peptidomimetics thereof or modified forms thereof, and pharmaceutical compositions comprising these compounds for the treatment of pancreatic cancer which is classifiable as Stage IV according to the Cancer Staging Manual of the American Joint Committee on Cancer.

Classification according to the TMN Anatomic Stage/Prognostic Group system for pancreatic cancer may be undertaken as described for pancreatic cancer in the Cancer Staging Manual. To this end a person skilled in the art may e.g. use the pancreatic staging form shown pages 249-251 of the Cancer Staging Manual, $7^{th}$ edition, 2010, American Joint Committee on Cancer, Springer.

The compounds and salts thereof can be formulated as mentioned above as pharmaceutical compositions (e.g. liquids, suspensions, emulsions, lozenges, sachets, ampoules, aerosols, powders, granules, tablets, pills, capsules, injections, solutions etc.) comprising at least one such compound alone or optionally in a mixture with pharmaceutically acceptable carriers, excipients and/or diluents.

The compounds/salts thereof and pharmaceutical compositions may be formulated for oral administration, e.g. by inhalation, for nasal administration or for administration by injection such as subcutaneous injection.

The invention is now described with respect to experiments which, however, are not to be construed in a limiting sense.

EXAMPLES

Example 1

1. Material and Methods
Cell Lines

The rat pancreatic carcinoma cell line BSp73AS (also designated AS) and its transfectants have been described (Orian-Rousseau et al., *Genes & Development* (2002), 16:3074-3086) and were grown in RPMI (Invitrogen, Karlsruhe, Germany) plus 10% FCS (PAA, Cölbe, Germany). The human pancreatic cancer cells L3.6p1 (Bruns et al., *Neoplasia* (1999), 1, 50-62) were maintained in DMEM (low glucose; Invitrogen, Karlsruhe, Germany) supplemented with 10% FCS (PAA, Cölbe, Germany), sodium pyruvate, nonessential amino acids, L-glutamine, and MEM vitamin solution (Pan Biotech, Aidenbach Germany).

Antibodies and Other Reagents

The human monoclonal antibody against CD44v6 (VFF18) was a gift from Bender (eBioscience, Campus Vienna Biocenter 2, A-1030, Vienna, Austria), the anti-ERK 1 (K-23), c-Met (C-28) and GFP antibody (sc-101525) were from Santa Cruz Biotechnology (Heidelberg, Germany), the cleaved Caspase-8 antibody (IMG-5703) from Imgenex (San Diego, Calif., USA), the CD31 antibody (MEC13.3) from BD Biosciences, Heidelberg, Germany, and the cleaved Caspase-3 (Asp175), Phospho-Met (Tyr1234/1235) (D26), Met (25H2) and the phospho-ERK phospho-p44/42 antibodies from Cell Signaling Technology (Beverly, England). The rat exon v6-specific antibody 1.1ASML has been described (Gunthert et al., *Cell* (1991), 65, 13-24). Secondary antibodies labeled with horseradish peroxidase were from Dako (Glostrup, Germany). The Alexa Fluor R 546 goat anti-rabbit secondary antibody was purchased from Life Technologies (Darmstadt, Germany). HGF was purchased from Peprotech (Hamburg, Germany). The CD44v6 rat and human peptides (14mer and 5mer) have been described (Matzke et al. *Cancer Res.* (2005), 65(14), 6105-6110). The sequence of the rat 14mer is KEKWFENEWQGKNP (SEQ ID NO: 10), the rat 5mer corresponds to NEWQG (SEQ ID NO: 11). The human 14mer corresponds to KEQWFGNRWHEGYR (SEQ ID NO: 6) and the human 5mer has the following sequence: NRWHE (SEQ ID NO: 2). For in vivo imaging experiments the rat 11mer WFENEWQGKNP (SEQ ID NO:12), the mouse 11mer WFQNGWQGKNP (SEQ ID NO: 13) and the human 11mer WFGNRWHEGYR (SEQ ID NO: 14) were labeled with the fluorescent dye DY681. As a control peptide in the case of rat cells or rat syngeneic models, the human v6 peptide of an identical length as the specific rat v6 peptide was used. In the case of human tumor cells or human orthotopic tumor model, the rat v6 peptide was used as a control. All peptides were produced by Bachem (Bubendorf, Switzerland) or Intavis (Köln, Germany). Lyophilized peptides were resuspended in PBS containing 1% BSA to a stock concentration of 1 mg/ml. Final dilutions were obtained by dilution in PBS.

Lentiviral Transfection of shRNA

The lentivirus system used for silencing Met has already been described (Corso et al., *Oncogene* (2008), 27(5):684-93). Lentiviruses were produced as described elsewhere (Vigna et al., *J. Gene Med.* (2000), 2(5):308-16). Briefly $4 \times 10^6$ 293 T cells (p12-15) were seeded in a 10 cm plate. 24 hours later the packaging vectors VSV-G, PMDL and Rev, the TetR and the lentivirus construct (either Met-shRNA or control-shRNA construct) were mixed and brought to a final volume of 450 µl by addition of TE. 450 µl of a 2.5 M CaCl$_2$ solution was added to this mixture. After vortexing and 5 minutes incubation 500 µl of 2×HBS solution was added drop wise to the DNA-TE-CaCl$_2$ mixture while vortexing at full speed. The precipitate was added to the 293T cells. After 16 h the medium was replaced and fresh medium containing 5 mM sodium butyrate was added. Medium was collected after 24 and 48 hours. Virus containing medium was then added to the target cells BSp73ASs6 (70% confluency) in presence of 8 µg/mL polybrene. 24 hours after infection the medium was replaced and production of shRNA was induced by addition of Doxycylcline to a final concentration of 1 µg/ml. BSp73ASs6 cells transduced with TetR and control-shRNA or Met-shRNA were treated with doxycycline for 72 hours before starting an assay or injection in the animal.

Western Blot Analysis

Serum-starved cells (24 hours) were induced with the growth factor HGF (10 ng/mL) at 37° C. for 5 minutes. Where indicated, the cells were treated with peptides (100 ng/ml) prior to induction at 37° C. for 10 minutes (100 ng/mL CD44v6 peptide or control peptide). Following the induction with HGF, cells were washed with ice-cold phosphate-buffered saline (PBS). To detect activated Met and Erk, cells were lysed in sodium dodecyl sulfate (SDS)-sample buffer containing 100 mM dithiothreitol (DTT), boiled and subjected to western blot analysis using antibodies against phospho-Met and ERK. The loading controls were performed on the same blot after stripping (62.5 mM Tris, pH 6.8, 2% SDS, 0.8% DTT) by probing with the Met respectively ERK antibody. Blots were stained using the enhanced chemiluminescence system (Thermo Fisher Scientific, Schwerte, Germany). Bands in western blot analysis were quantified with the program Image J (National Institutes of Health).

Quantitative Determination of HGF and VEGF in Cell Culture Supernatant

Determination of human HGF and VEGF levels in cell culture medium of L3.6pl cells were performed using the Quantikine Human HGF Immunoassay and Quantikine Human VEGF Immunoassay from Roche (Mannheim, GER). For this purpose $3 \times 10^6$ cells were cultured for 5 days in a 15 cm plate in the presence of the respective peptides as indicated. The supernatant (20 ml) was centrifuged (1200 rpm) and the assay was performed according to manufacturer's instructions.

Animal Experiments

Male athymic nude mice (NCI-nu) were purchased from Harlan (Roβdorf, Germany). BD10 and BDX rats were bred in house. The animals were housed and maintained under specific pathogen-free conditions in facilities approved by the Regierungspräsidium Karlsruhe. All animals were handled according to German regulations for animal experimentation. The animal experiments were approved by the Regierungspräsidium Karlsruhe (35-9185.817G-192/10). Imaging experiments (FIG. 3) were performed in Göttingen were authorized by the Regierungspräsidium (35-9185.817G-106/09).

In the case of the rat syngeneic model, $1 \times 10^6$ pancreatic cells (BSp73AS and its transfectants) were subcutaneously injected into the right posterior flank of the animals. Tumors developed for four weeks. During this time period animals injected with BSp73ASs6 cells expressing Met-shRNA or control-shRNA received doxycycline in the drinking water. At the end of the experiment, primary tumors were isolated. Lungs and axillary lymph nodes were analyzed. The tissues were incubated for 24 h in a zinc-fixative (0.5 g calcium acetate, 5.0 g zinc acetate, 5.0 g zinc chloride, in 1 L 0.1 M Tris pH 7.4) and embedded in paraffin for further analysis. In case of peptide or antibody treatment tumors developed for one week before the first treatment. Where indicated, animals received 200 µg of peptide or antibody per injection three times per week for four weeks. Tumor growth was monitored weekly using a caliper Animals were killed at day 28 or 30 after start of the treatment.

In the case of the human orthotopic model, L3.6pl pancreatic carcinoma cells (passage 24-26) were suspended in Hank's balanced salt solution (Invitrogen, Karlsruhe, Germany) after trypsinization. The cells were injected orthotopically in the pancreas of male nude mice as described (Bruns C J et al. (1999) Neoplasia 1(1):50-62). Two groups of 15 mice each were injected i.p. 7 days later with either the human v6 peptide respectively rat control peptide (20 µg). For all experiments described and depicted herein either the rat 14mer control peptide or the human 14mer peptide were used. All experiments were then repeated with the rat 5mer control peptide or the human 5mer peptide (N-R-W-H-E, SEQ ID NO: 2). The same results as for the 14mer peptides were observed. The injection was repeated three times per week for 21 days. Two days after the last treatment the animals were killed.

In order to examine the regression of metastases (either BSp73ASs6 or L3.6p1) were implanted as described above. Tumor growth was allowed for three weeks. At that time all animals had developed metastases in the control group. Animals were injected i.p. with 20 µg (L3.6p1 orthotopic mouse model: human v6 peptide or rat control peptide) or i.v. with 200 µg (rat syngeneic model: rat v6 peptide or mouse control peptide) of peptides three times per week. Animals were killed 23 days after the start of the peptide treatment.

In Vivo Imaging Using Optix MX2

In vivo imaging of the subcutaneously grown BSp73ASs6 tumors in BD10 or BDX rats was performed using the near infrared fluorescence (NIRF)-imaging system Optix MX2 (ART, Montreal, Canada) as described earlier (Napp et al., *Int J Cancer* (2010), 127:1958-1974). To avoid autofluorescence of fur, rats were shaved around the tumor prior to imaging. Subsequently, animals were anesthetized using 2% isoflurane and gently fixed on the devices' heated plate for the entire time of data acquisition. To reduce fluorescence background, rats were fed with chlorophyll-reduced food (Provimi Kliba AG, Kaiseraugst, Switzerland) for one week prior NIRF imaging. All in vivo analyses were preceded by native scans of animals without any injection of the fluorescent probe. For in vivo analysis, rats were injected with 200 DY681-labeled rat v6 11mer peptide or the human v6 11mer peptide via the tail vein. Controls were injected with the equal amount of DY681-labeled mouse v6 11mer peptide. The rat 11mer had the sequence WFENEWQGKNP (SEQ ID NO: 12), the mouse 11mer had the sequence WFQNGWQGKNP (SEQ ID NO: 13) and the human 11mer had the sequence WFGNRWHEGYR (SEQ ID NO: 14). All peptides were labeled with the fluorescent dye DY681. Data were acquired at the indicated time after injection of the peptides. For ex vivo monitoring animals were sacrificed after 24 hrs after peptide injection and tumor and organs of interest were scanned ex vivo using Optix MX2.

DY681 fluorescence was measured using excitation at 670 nm in combination with a 700 nm long-pass emission filter. Scans were performed with 1.5 mm raster, photon collection time of 0.5-1 s per scan point and varying laser power. Data sets were analyzed with OptiView (ART). Fluorescence intensity data are displayed in normalized counts (NC) where the measured fluorescence intensity (counts) was normalized for varying laser power and integration times, allowing comparison of measurements with different settings.

In Vivo Imaging Using Pearl Imager

In vivo imaging of the mice with the L3.6p1 tumors was performed using the Pearl™ Imager (LI-COR Biosciences, Bad Homburg, Germany) The system uses two lasers (685 and 785 nm) for excitation and a charge-coupled device detector for signal detection. The laser excitation enables a deep tissue penetration. With the near-infrared detection a high sensitivity due to the reduced tissue auto-fluorescence is achieved. In order to standardize the images we made use of the Pearl Cam Software. The animals were fed with chlorophyll-reduced food to reduce the fluorescence background one week before imaging (Regime 210, safe-diets, Augy, France). Prior to imaging the mice were anesthetized with 2.0% isoflurane. Animals were placed on the heated plate of the imager and continuous delivery of isoflurane was achieved through a nose cone in the imaging drawer. Images were captured at white light, 700 and 800 nm Animals were imaged prior to i.v. peptide injection and 24 h after injection with either DY681-labeled human v6 peptide or DY681-labeled rat v6 peptide as control Immediately after each imaging session animals were killed, tumor, liver and spleen isolated and scanned ex vivo at white light, 700 and 800 nm.

Immunofluorescence

ASs6 or L3.6p1 cells were seeded at 5,000 cells/well of a Lab-Tek® Chamber Slide™ (Nunc, Napierville, Ill., USA). On the following day the cells were washed with cold PBS and fixed with 4% Formalin for 30 min at RT. Unspecific binding was blocked with 1% BSA in PBS for 1 hour at RT. The cells were incubated for 1 hour with the DY681-labeled peptides. After three washing steps with PBS the cover slips were mounted with Fluorescence Mounting Medium (Dako, Glostrup, Denmark) and the immunofluorescence was measured by a laser scanning confocal microscope Leica TCS2 SP2 (Exton, Pa., USA) and processed using Leica confocal software. A 20× objective was used for imaging.

Histology

For histomorphological analysis paraffin-embedded sections of lungs were stained with hematoxylin and eosin and periodic acid-Schiff (H&E or PAS). Serial sections of the whole tissue blocks were examined by analyzing slices every 20 μm; in each slice, the presence and the extension of the metastatic deposit was assessed, according to the procedure routinely used by pathologists to evaluate the presence of micrometastases.

Immunohistological and Immunofluorescence Analysis

7 μm thick paraffin sections were deparaffinized and rehydrated. For P-Met staining antigen unmasking was achieved by boiling the slides in 1 mM EDTA pH 8.0 followed by incubation for 15 minutes at a sub-boiling temperature, for CD31 staining the sections were treated with Proteinase K (8 μg/ml) for 10 min at 37° C. For immunofluorescence staining of P-Met, unspecific binding was blocked with 5% goat serum (DAKO, Glostrup, Denmark) (diluted in 1×PBS/0.3% Triton X-100) for 60 minutes. In the case of immunohistochemistry, endogenous peroxidases were at first blocked with 3% $H_2O_2$ in PBS followed by incubation with biotin blocking system (Dako, Glostrup, Denmark) and then unspecific binding was inhibited by incubation with 5% FCS in PBS. The sections were incubated with the P-Met antibody (D26, dilution 1:50 in 1×PBS/1% BSA/0.3% Triton X-100), Met antibody (C-28, dilution 1:50), GFP antibody (sc-101525, dilution 1:50) or antibody (5 μg/ml) over night or VFF18 (5 μg/ml) o/n at 4° C. After washing in PBS the sections were incubated with Alexa Fluor R 546 goat anti-rabbit (in case of immunofluorescence P-Met and Met staining, dilution 1:500) or a biotinylated secondary antibody (for immunohistochemical stainings rabbit anti-rat antibody for VFF18 and CD31, goat anti-rabbit for P-Met, cleaved Caspase-3 and cleaved Caspase-8 and rabbit anti-mouse for GFP, dilution 1:500) for 45 minutes. For DAB (3,3'-diaminobenzidine) staining the sections were treated with a streptavidin-peroxidase conjugate (Dako, Glostrup, Denmark) and developed with DAB substrate system (3,3'-diaminobenzidine; Biozol, Eching, Germany) For immunofluorescence DAPI was used for nuclear staining.

2. Results

The Co-Receptor Function of CD44v6 for Met is the Decisive Step for Metastatic Spreading of Rat Pancreatic Tumor Cells To investigate whether the co-receptor function of CD44v6 for the Met receptor is the decisive step for the metastatic spreading of tumor cells it was first examined whether a CD44 isoform containing exclusively the exon v6 or all the variant exons v1-10 included in the CD44v1-10 isoform would confer metastatic potential to the rat BSp73AS cells. In these cells, Met cannot be induced by HGF unless a CD44v6 containing isoform is transfected (FIG. 1A). Removal of exon v6 e.g. in CD44v1-10Δv6 impaired the activation of Met by HGF (FIG. 1A).

The parental BSp73AS cells and cells stably transfected with the constructs mentioned above (CD44v6, CD44v1-10 and CD44v1-10Δv6) were subcutaneously injected into isogenic rats. In all animals primary tumors were palpable already after one week. In the case of cells transfected with CD44v6 or CD44v1-10 the axillary lymph nodes of the corresponding animals were enlarged already two weeks after injection and the animals were killed after six weeks. Histomorphological examination of the lungs and lymph nodes revealed that all rats bearing CD44v6 or CD44v1-10 expressing tumors developed nodal and intrapulmonary metastases. In contrast, the parental cells or the cells transfected with CD44v1-10Δv6 gave rise to primary tumors but not to metastasis, neither in lymph nodes nor in the lungs (FIG. 1B and Table 1). No micrometastasis was detected in the lungs of these animals (Table 1). Thus, CD44 isoforms such as CD44v6, that allow Met activation, also confer metastatic propensity to BSp73AS cells.

Next, BSp73ASs6 cells (BSp73AS cells expressing the CD44v6 isoform in addition to CD44s) were stably transfected with lentivirus expressing Met shRNA sequences. It was confirmed that the cells do not express Met (FIG. 1A, last two lanes). Then, these cells (or cells infected with lentivirus expressing control sh-RNA sequences) were injected into syngeneic animals. The animals were examined six weeks after injection. All animals developed primary tumors (Table 1). However, Met activation was only observed in the primary tumors of cells infected with control sh-RNA expressing lentivirus, but not in primary tumors expressing Met sh-RNA (FIG. 1C). Furthermore, when Met expression was abolished no metastasis nor micro-metastasis was detected neither in lung nor in the axillary lymph nodes (FIG. 1B, Table 1) demonstrating the importance of Met for the metastatic process. From these data, it can be concluded that both CD44v6 and Met are required for metastatic spreading of BSp73AS cells.

Next it was examined whether the rat counterparts to a peptide of SEQ ID NO: 2 (human CD44v6 5mer peptide) or SEQ ID NO: 6 (human CD44v6 14mer peptide) that interferes with the co-receptor function, also inhibit metastasis formation. Rat peptides had the sequences KEKWFENEWQGKNP (SEQ ID NO: 10) and NEWQG (SEQ ID NO: 11). BSp73ASs6 cells were subcutaneously injected into syngeneic rats and rat CD44v6 peptides of SEQ ID NO: 10 or SEQ ID NO: 11 (or mouse control peptides) or the CD44v6 antibody (or IgGs as a control) were injected intra-tumoral or intravenously three times a week. Both, treatment with the v6 specific antibody or with the v6 specific peptide completely inhibited metastasis (FIG. 2B, Table 2). In lung sections from animals treated with the CD44v6 peptide, neither metastasis nor micro-metastasis could be detected upon histological analysis using PAS and H&E staining (FIG. 2C and Table 2). This is in clear contrast with the results obtained from animals treated with the control peptide (or control IgG) where numerous metastases were detected in the lungs (FIG. 2B, C). Interestingly, the outgrowth of primary tumors was not influenced by either treatment (FIG. 2D). This is compatible with the fact that also BSp73AS cells or BSp73ASv1-10Δv6 cells can induce the formation of primary tumors similarly to the v6 transfectants.

Taken together the experiments suggest that the co-receptor function of CD44v6 for Met is the decisive step for metastatic spreading in the rat pancreatic tumor cell system and that it does not account for the outgrowth of the primary tumor.

Specific Binding of a CD44v6 Peptide to Tumor Cells In Vivo

In order to test the specificity of the binding of CD44v6 peptides to the tumor site and to the metastases and to estimate the binding kinetics in vivo, near infrared fluorescence (NIRF) imaging with the Optix MX2 was. For this purpose two CD44v6 peptides were labeled with the fluorophore DY681: a rat specific one, rv6 pep Dy681 and a mouse specific one, mv6 pep Dy681, as a control. In vitro testing showed that indeed, only the labeled rat peptide but not the mouse peptide inhibited Met activation as was demonstrated in FIG. 3A right side. Furthermore, the DY681-labeled rat v6 peptide, but not the DY681-labeled mouse v6 peptide bound to BSp73ASs6 cells in tissue culture (FIG. 3A left side).

For in vivo experiments, BSp73ASs6 cells were injected subcutaneously into syngeneic rats. Three weeks later, they received either of the labeled v6 peptides by injection into the tail vain. The accumulation of the fluorescence was measured in the tumor region by Optix MX2 at the indicated time points. Prior to intravenous (i.v.) injection of Dy681-labeled peptides mice were natively scanned in order to measure levels of autofluorescence background. Then, in vivo binding kinetics of the Dy681-labeled v6 peptides to the subcutaneous tumors were determined. As shown in a series of representative NIRF images taken 1, 2, 3 and 7 days after peptide injection, high fluorescence intensity was detected over the tumor area for at least 2 days in vivo, with a maximum at 1 day. Injection of the control peptide m6 pep Dy681 did not result in any fluorescent signals over the tumor area (FIG. 3D).

To specifically examine the distribution of the v6 peptides in the tumor and also in the lungs, both tissues were excised 24 h after peptide injection and examined ex vivo by Optix MX2 (FIG. 3C). Fluorescence intensities could only be detected in tumors and in specific areas of the lungs scanned ex vivo and excised from mice that received rv6 pep Dy681, but not in tumors and lungs from all control rats previously injected with mv6 pep Dy681 (FIG. 3C). These results confirmed the in vivo observation that the rat peptide binds specifically to the subcutaneous rat pancreatic tumor and furthermore even suggest in vivo binding to metastases. Indeed, histological analysis revealed the presence of metastases in the lungs of all animals.

Metastasis Formation of Human Pancreatic Tumor Cells is Inhibited by a Human CD44v6 Peptide of SEQ ID NO: 2 or SEQ ID NO:6

To expand the studies to human pancreatic tumors, the highly metastatic human pancreatic carcinoma cells L3.6p1 (Bruns, et al. *Neoplasia* (1999), 1(1):50-62) were investigated. These cells originate from the COLO 375 cells that have been passaged several times in the liver and the pancreas, a step that rendered them more and more metastatic. It was confirmed that Met is dependent on CD44v6 for its activation and signaling in these cells (FIG. 4A). The L3.6p1 cells were treated with HGF in the presence or absence of a human v6 peptide of SEQ ID NO: 2 or SEQ ID NO:6 and Met activation and downstream signaling to ERK was measured. Phosphorylation of both Met and ERK was inhibited by the human v6 peptide. Treatment with a corresponding rat v6 peptide (ctrl peptide, SEQ ID NO: 10 or 11) had no influence on receptor activation and signal transduction (FIG. 4A).

To test the effect of the peptide on tumor growth and metastasis formation the L3.6p1 cells were orthotopically injected into the pancreas of immunosuppressed mice (NCI-nu). These mice developed primary tumors and showed numerous metastases in the liver after four weeks. The primary tumor expresses a high amount of CD44v6 (FIG. 4B). Intraperitoneal injection (i.p.) of the human-specific peptide three times per week for three weeks completely repressed Met activation as shown by the immunofluorescence staining for phospho-Met and Met in the tumor (FIG. 4C). These data demonstrate that the peptide interferes with the co-receptor function of CD44v6 for Met and abrogates Met phosphorylation in vivo. Since the activation of Met is species-specific and the human Met receptor can only be activated by human HGF this result suggests that the L3.6p1 cells produce their own HGF. Interestingly, in contrast to the rat system the outgrowth of the primary tumor in the pancreas was strongly repressed by the human v6 peptide (FIG. 4D top). The outgrowth of the primary tumor in the pancreas was also strongly repressed (FIG. 4D bottom). The rat-specific peptide (ctrl peptide) had neither any influence on metastasis formation nor on growth of the primary tumor (FIG. 4D). This result suggests that the L3.6p1 cells produce their own HGF. Indeed, human HGF in a concentration of 3375 pg/ml was detected in the supernatant (see Material and Methods) after 5 days of culture (data not shown).

It was observed that the outgrowth of the primary tumor was retarded upon inhibition of tumor angiogenesis with a murine-specific v6 peptide. Here it is shown that the treatment with the human peptide also decreased angiogenesis as exemplified by a reduced vessel number and vessel size in the v6 peptide-treated tumors. The decreased angiogenesis explains the reduced tumor volume (FIG. 4D, E). Since the v6 peptides act in a species-specific manner, the inhibition of angiogenesis cannot be due to an effect on the murine endothelial cells but rather to an inhibition of VEGF production by human pancreatic carcinoma cells. Indeed, the human L3.6p1 cells produce hVEGF, a secretion that can be blocked by treatment with the human v6 peptide (FIG. 4F). The most striking observation was that the human-specific peptide completely inhibited metastasis formation within the liver (FIG. 4G). The rat-specific peptide (ctrl peptide) had no influence on metastasis formation or on growth of the primary tumor (FIG. 4C-G).

Then, the specificity of binding of the human CD44v6 peptide to the tumor in vivo was examined using the small animal imaging system Pearl Impulse. The human labeled peptide but not the rat peptide inhibited Met activation in L3.6p1 cells (FIG. 5A right side) and bound to these cells in cell culture (FIG. 5A left side). In vivo the fluorescently labeled (DY 681) human peptide accumulated specifically in the tumor induced by orthotopically injected L3.6p1 cells (FIG. 5B). No fluorescence was detected in animals that were treated with a control peptide. Furthermore, no signal was observed in animals that received no peptide whether or not they had developed a tumor (FIG. 5B). Ex vivo analysis of organs isolated from animals treated with the labeled human v6 peptide allowed detection of binding not only to primary tumors but also to areas of the liver most probably corresponding to metastases (FIG. 5C). Thus these experiments reveal that the CD44v6 peptides not only target the primary tumors but also distant metastases.

Already Established Metastases are Eliminated by CD44v6 Peptides

The specific binding of the CD44v6 peptides to specific areas of the lungs in the rat system and of the liver in the human model raises the question whether these peptides might have an effect on already established metastases. In the experiments described in FIGS. 2 and 4 the peptides were applied early after injection of the tumor cells and repressed completely the establishment of metastases. In order to measure the effect of the CD44v6 peptide on already established metastases, other experimental settings were used. BSp73ASs6 cells were injected subcutaneously into syngeneic rats and L3.6p1 cells orthotopically into male nude mice and allowed to grow for 3 weeks. At that time all animals from the control group had developed metastases (Table 3) suggesting that this was also the case in the groups used for peptide treatment. The animals were then treated either with the species-specific CD44v6 peptide or with the control peptide (mouse for the rat system and rat for the human system) twice per week for another three weeks (Scheme in FIG. 6A) and then tested for the presence of metastases. At the end of the experiments metastases could be detected in all animals treated with the control peptide (Table 3, FIG. 6B for the BSp73ASs6 cells, Table 3, FIG. 6C for L3.6p1 cells) whereas animals treated with the species-specific CD44v6 peptides were free of metastasis. Thus, already established metastases are eliminated by treatment with the CD44v6 peptides.

One hypothesis for the disappearance of metastases is that the peptides induce apoptosis of CD44v6-expressing metastatic cells in the secondary organs. In order to test this hypothesis, the experiment described above using the BSp73ASs6 cells was repeated. The cells were injected subcutaneously in syngeneic rats and the tumor was allowed to develop for three weeks. After that time the animals were separated in two groups of 10 animals that were injected either with the specific rat CD44v6 peptide or with the control peptide (mouse) every second day. One day following each injection of the peptide, the lungs of one animal were removed and apoptosis was measured using an antibody that detects the cleaved form of Caspase 3. Apoptotic cells were detected as early as three days after the first injection of the peptides in the tumor areas of animals treated with the CD44v6 peptide. No apoptosis at all was detected in the animals injected with the control peptide (FIG. 7). A maximum of apoptosis was measured eight days after the first injection of the CD44v6 peptides. Twelve days after injection of the CD44v6 peptide, less apoptosis was observed. At day twenty-two, no metastasis could be detected anymore in animals treated with the CD44v6 peptide whereas metastatic spreading was evident in the lungs of control animals (FIG. 7). From these experiments, it is concluded that the CD44v6 peptide induces apoptosis of metastatic cells.

To discriminate whether the intrinsic pathway characterized by the release of mitochondrial proteins or the extrinsic pathway activated by ligand-bound death receptors for apoptosis was induced by the v6 peptide the expression of cleaved caspase-8 in the metastases treated with the v6 peptide was investigated. A kinetic of activation of caspase-8 similar to the one obtained for caspase-3 in the lungs of the v6 peptide treated animals was observed. From these experiments we conclude that the CD44v6 peptide induces apoptosis of metastatic cells via the extrinsic apoptotic pathway.

Example 2

Pegylated CD44v6 Peptides Inhibit HGF Dependent CD44v6 Mediated Signaling

1. Material and Methods
Synthesis of Pegylated Peptides

Peptide synthesis was performed on an Applied Biosystems automated peptide synthesizer (model 433A) and the peptides were purified by preparative HPLC. Peptides of sequences NEWQG (SEQ ID NO: 11) and a control peptide NAAAG (SEQ ID NO: 15) were synthesized. Crude and purified products were characterized by LC coupled to a mass spectrometer (μTOF LCMS from Bruker Daltonics-Bremen, Germany).

Peptide synthesis was performed using standard Fmoc solid phase peptide synthesis protocols (see e.g. Fields et al., *Int J Pept Protein Res.* (1990), 35, 161-214, Maisch et al., *J Am Chem Sco.* (2009), 131, 15596-15597, Strandberg et al., *Biophys J.* (2006), 90, 1676-1686, and Wadhwani et al., *J Org Chem.* (2006), 71, 55-61). Fmoc deprotection was done with 20-22% piperidine in NMP. Coupling was performed using a mixture of Fmoc-amino acid:HOBt: HBTU: DIEA (4:4:3.9:8) in DMF. Peptides were cleaved from the solid support using a mixture of TFA:$H_2O$:TIS (93.5:2.5:4). The cleavage reagents were removed under $N_2$-flow, and the labeled peptides were precipitated using diethyl ether.

Preparative HPLC was performed on a reversed phase C18 column (4.6 mm×240 mm) at 35° C. using a Jasco-HPLC system (Tokyo, Japan) fitted with a diode array detector. Epimeric peptides were separated using acetonitrile/water gradients 0.1% TFA.

All amino acids were purchased from Novabiochem (Schwalbach, Germany). The MeO-PEG-COOH (molecular weight 750 Da and 2000 Da) and the coupling reagents (HBTU, HCTU) and DIEA were from his Biotech (Marktredwitz, Germany), and solvents and other reagents were from VWR-Merck (Bruchsal, Germany).

The following compounds were synthesized:
PEG-control peptide: PEG-NAAAG (PEG-SEQ ID NO: 15),
PEG-rat CD44v6 peptide: PEG-NEWQG (PEG-SEQ ID NO: 11)
Palmitic-NH-PEG-CONH-control peptide
Palmitic-NH-PEG-CONH-rat CD44V6 peptide
Palmitic-NH-PEG-CONH-control peptide and Palmitic-NH-PEG-CONH-rat-CD44V6 peptide were synthesized by first coupling Fmoc-NH-PEG-COOH molecular weight 3000 Da to either SEQ ID NO: 11 or SEQ ID NO: 15. Then the pegylated peptides were reacted with palmitic acid.
Activation Assays The PEG-control peptide and PEG-rat CD44v6 peptide were compared for their ability to block HGF induced activation of the receptor tyrosine kinase Met and ERK.

Rat pancreatic cancer cells BSp73ASs6 (also designated Ass6) were incubated for 10 min at 37° C. with either ctrl-peptides (SEQ ID NO: 15), non-pegylated v6-peptides (SEQ ID NO: 11) and increasing concentrations of the pegylated peptides, namely PEG-rat control peptide and PEG-rat CD44v6 peptide, before induction with HGF (10 ng/ml; 5 min at 37° C.).

Activation of ERK and Met was determined by standard SDS and Western Blotting techniques using a phospho-Met and phospho-Erk specific antibody (phospho-Met clone D16 cell signaling, phospho-Erk p42/44 cell signaling)

Cellular Assays

A scatter assay was performed additionally. HT29 colon cancer cells were grown in medium containing 10% FCS. One day after seeding, the cells were starved. On the third day, the cells were induced with HGF (10 ng/ml) and pre-incubated with either no peptide, ctrl-peptides (SEQ ID NO: 15), non-pegylated v6-peptides (SEQ ID NO: 11) or the pegylated peptides, namely PEG-rat control peptide and PEG-rat CD44v6 peptide.

2. Results

FIGS. 9 and 10 show that pegylated peptides are efficient in inhibiting HGF dependent activation of Met and ERK Inhibition of ERK is even more efficient with pegylated vs. non-pegylated peptides.

Example 3

In Vitro Results

Linear CD44v6 Peptides Described Herein
 rat: 14mer KEKWFENEWQGKNP (SEQ ID NO: 10), 5mer NEWQG (SEQ ID NO: 11), DY681 labeled 11mer WFENEWQGKNP (DY681-SEQ ID NO: 12)
 human: 14mer KEQWFGNRWHEGYR (SEQ ID NO: 6), 5mer NRWHE (SEQ ID NO: 2), DY681 labeled 11mer WFGNRWHEGYR (DY681-SEQ ID NO: 14)
 mouse: DY681 labeled 11mer WFQNGWQGKNP (DY681-SEQ ID NO: 13)

1. In Vitro Inhibition of RTKs Using the Human v6 Peptides
 Linear peptide (human, 14mer KEQWFGNRWHEGYR (SEQ ID NO: 6), 5mer NRWHE (SEQ ID NO: 2))
Cell Lines Used
 HT29 (colorectal cancer)
 HeLa (cervical cancer)
 L3.6p1 (human pancreatic carcinoma cell)
 MCF7 (human breast cancer)
1.1 Epithelial Cells The contribution of CD44v6 to Met signaling in the human epithelial pancreatic cancer cells L3.6p1 (derived from Colo 357), the cervix carcinoma cells HeLa and the colon cancer cells HT29 were analysed using the CD44v6 peptide (v6 14mer; v6 5mer tested as well, data not shown). It was able to prevent activation of Met and of its downstream target Erk when added to the cells before induction with HGF (FIGS. 12A, B and C). As incubation with a control peptide did not interfere with Met activation and signaling, these results show that CD44v6 is required for Met activation in all this cell lines.

Besides VEGFR and Met the dependency of ErbB1 on CD44v6 was investigated. EGF as well as five other ligands, namely AR, BC, ER, HB-EGF, and TGF-α, can activate the ErbB1 receptor. EGF, AR and TGF-α bind to either an ErbB1-homo- or an ErbB1/2-heterodimer. In addition to these dimers, BC, ER and HB-EGF can also bind to an Erb4/4 homo- or an ErbB2/4 heterodimer. Here it was investigated whether the activation of the ErbB receptors by the indicated ligands is also dependent on CD44v6.

Figure 1:
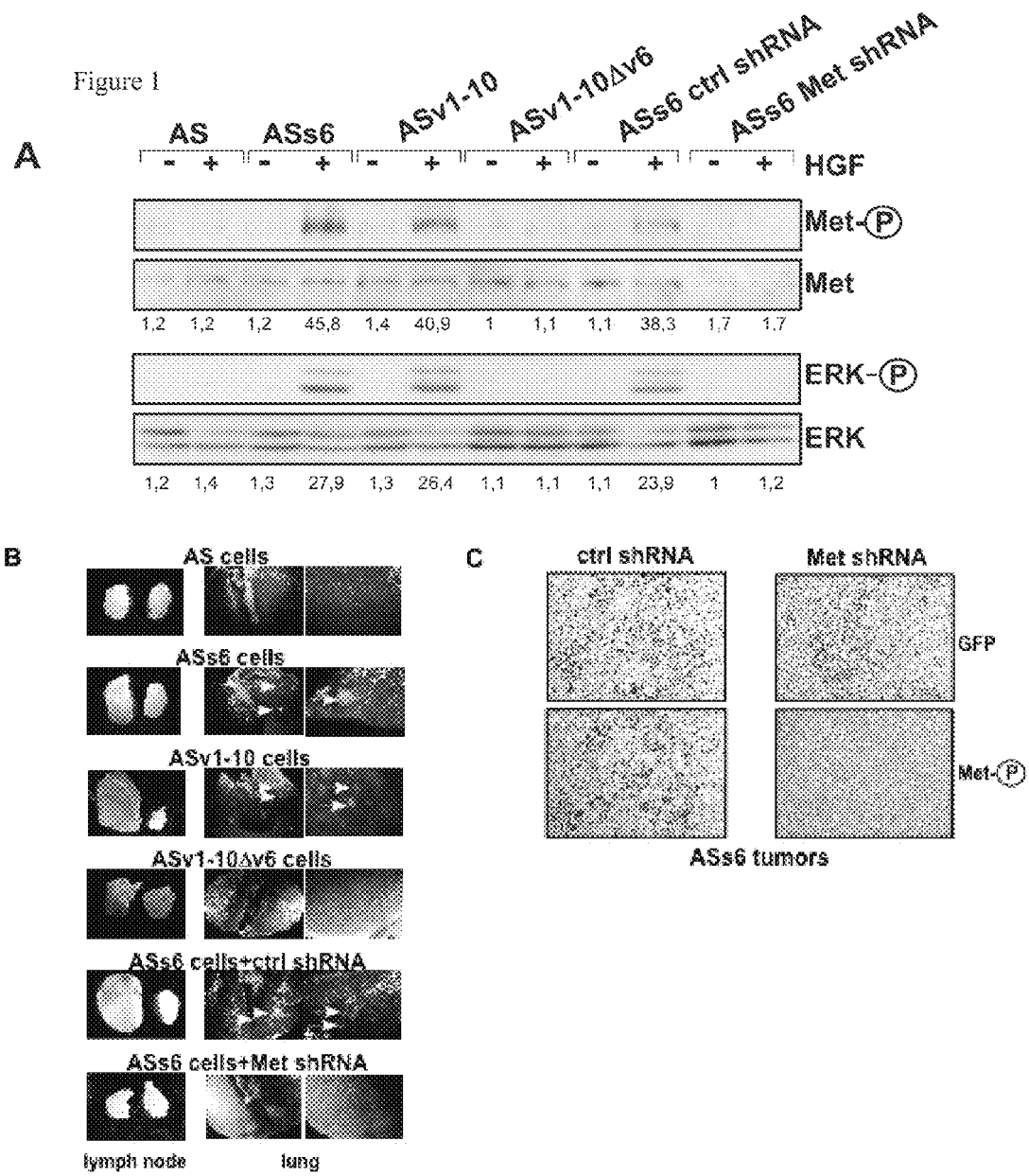
Figure 2:
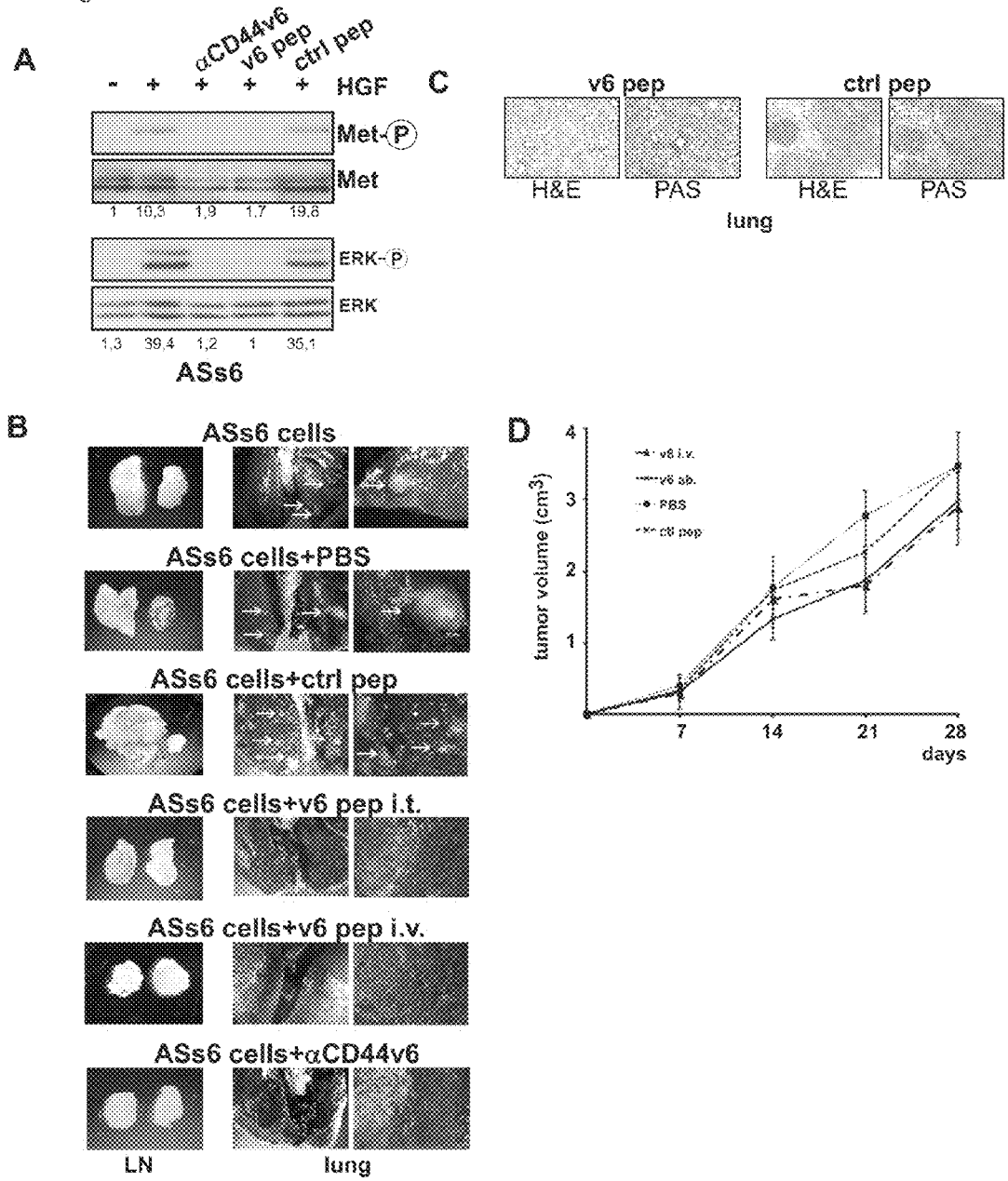
Figure 3:
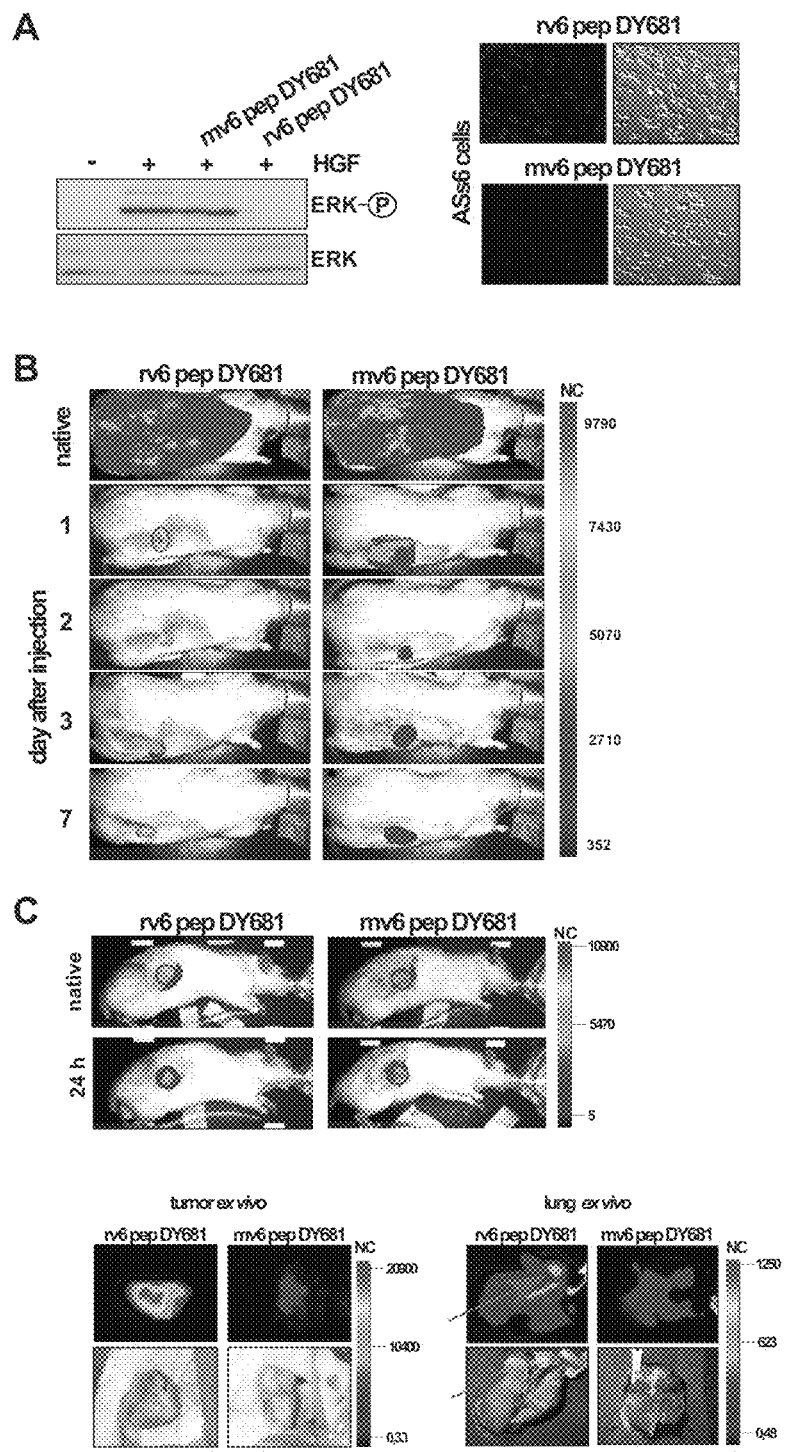
Figure 4:
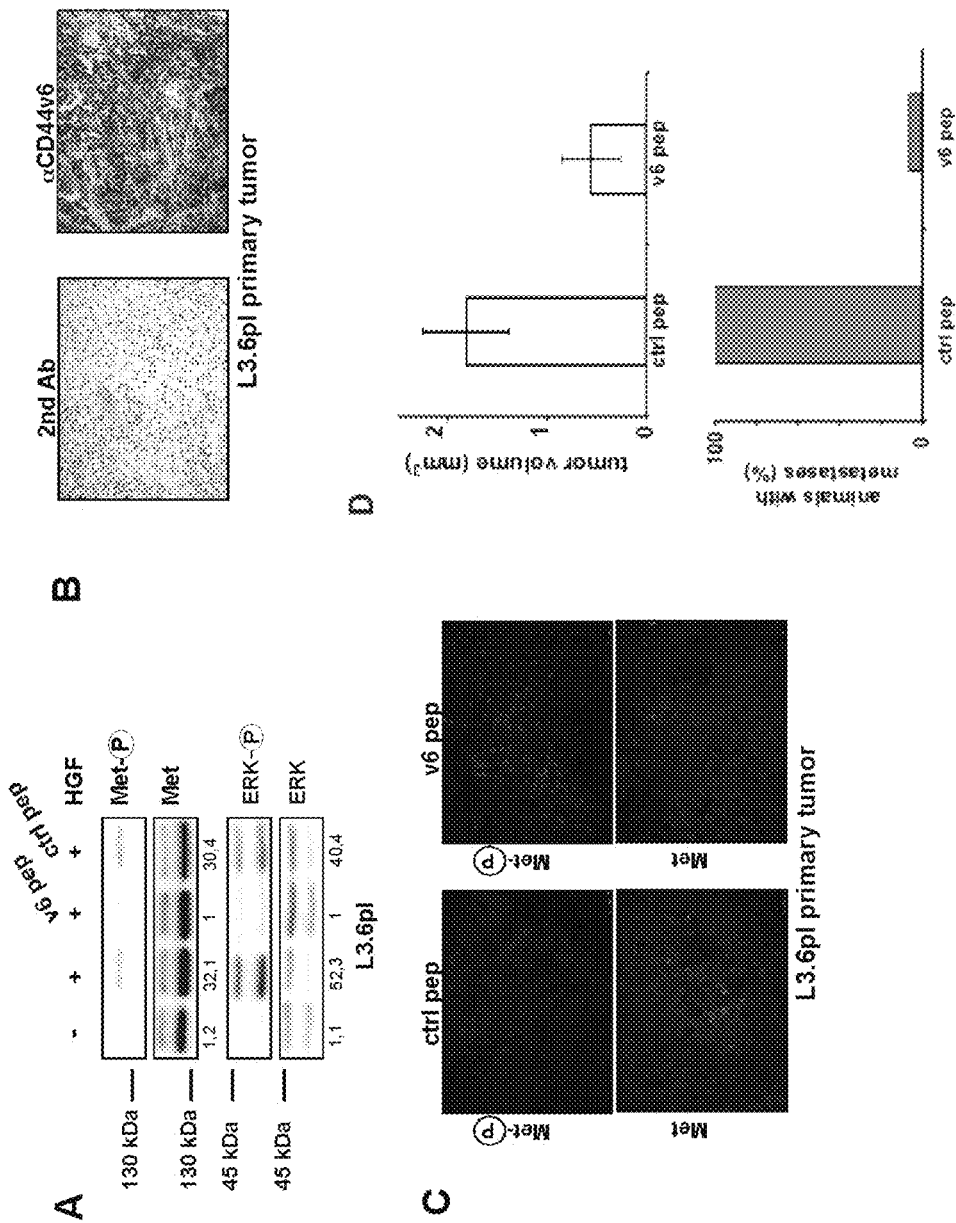
Figure 4:
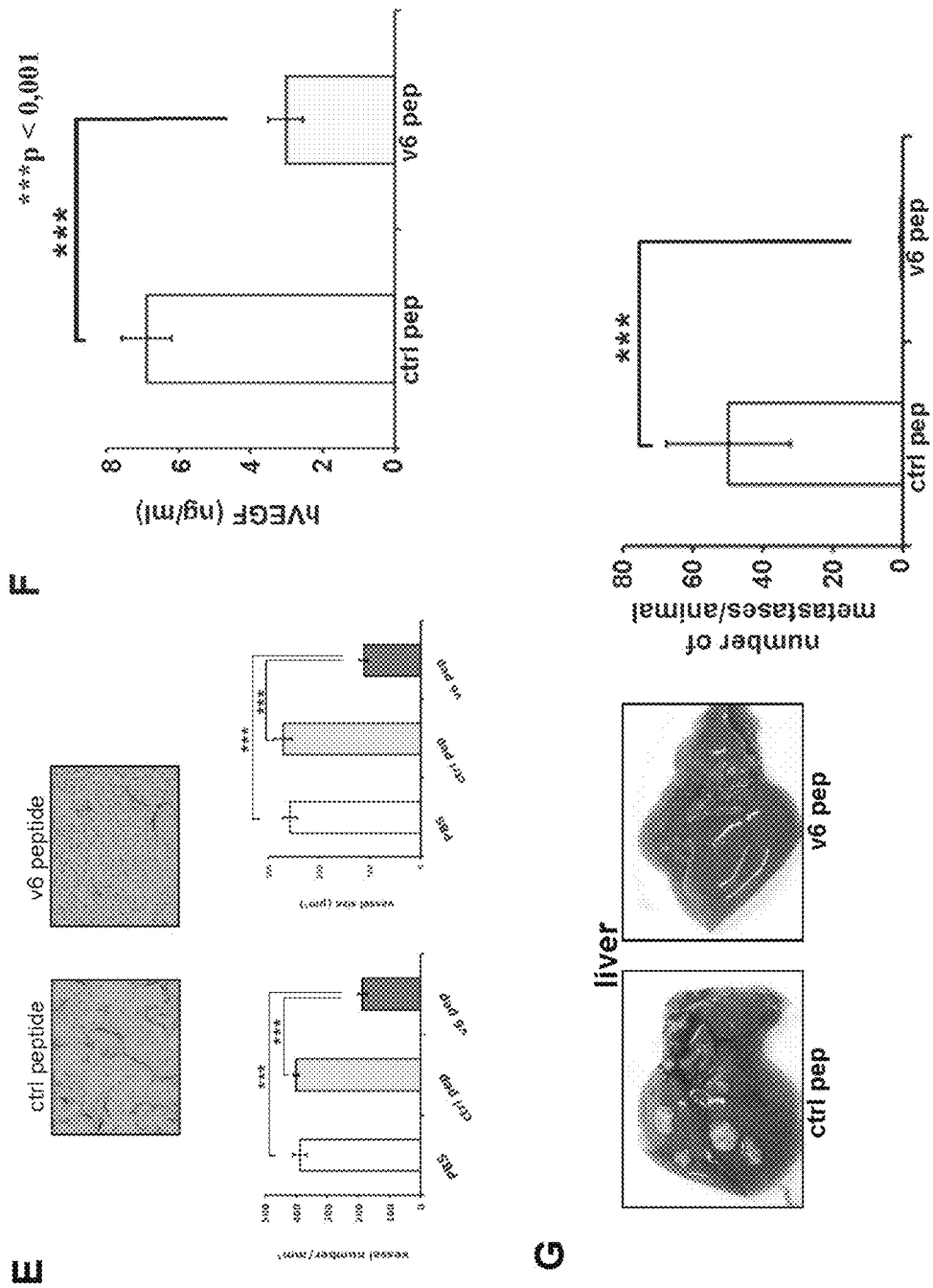
Figure 5:
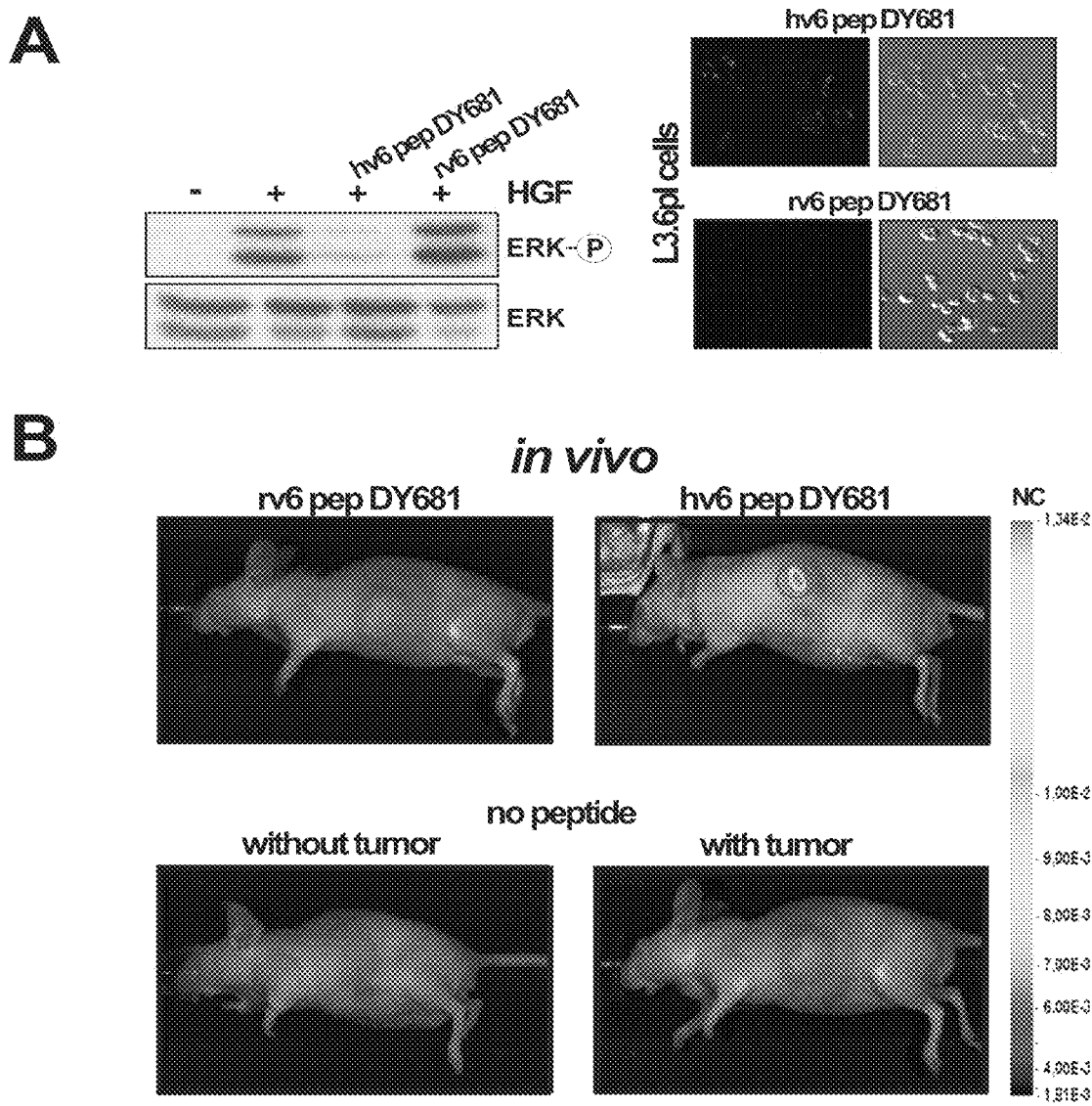
Figure 5:
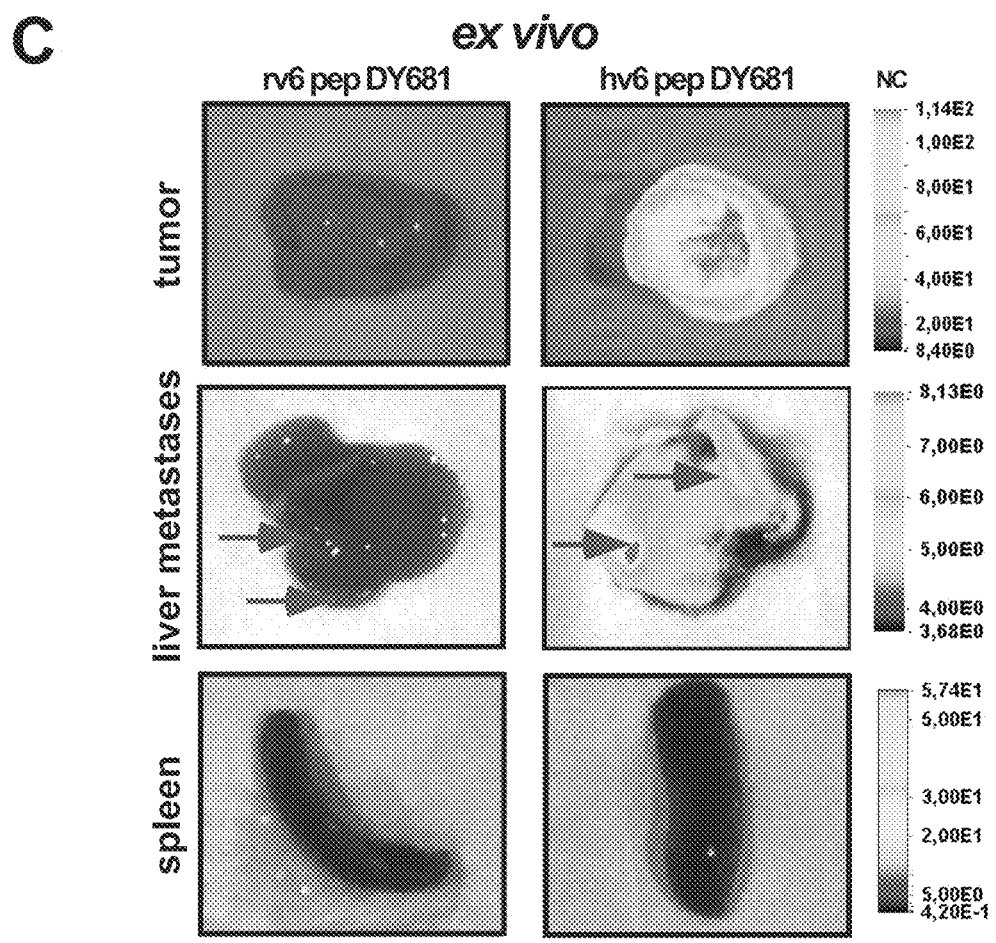
Figure 6:
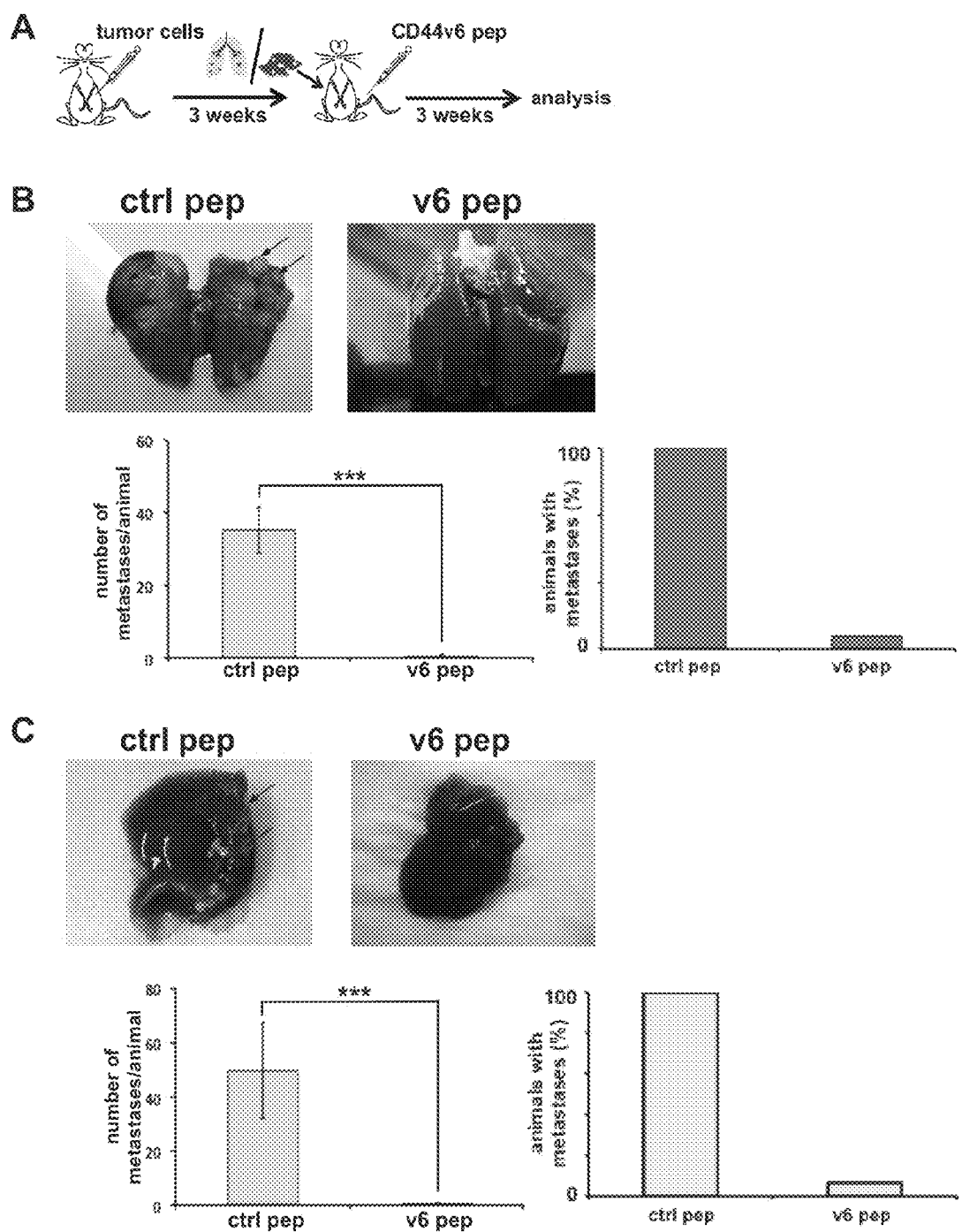
Figure 7:
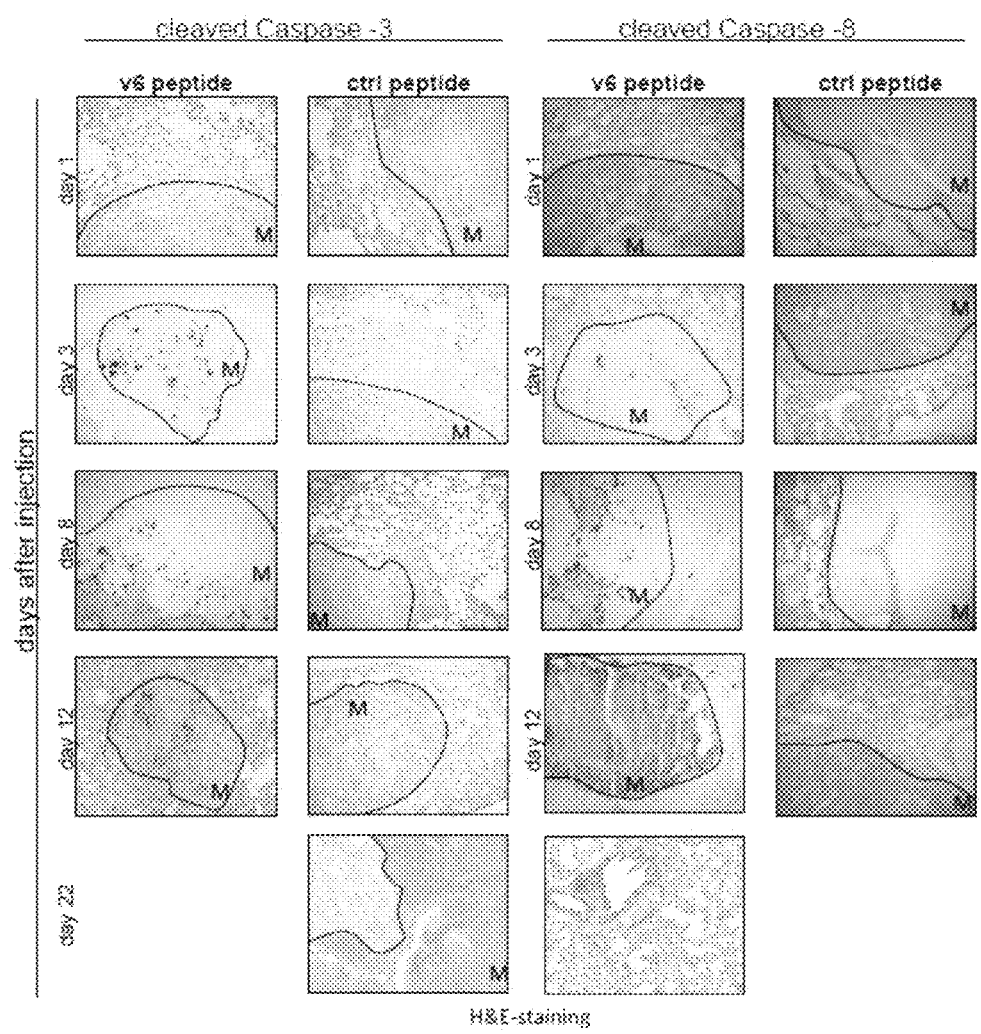
Figure 10:
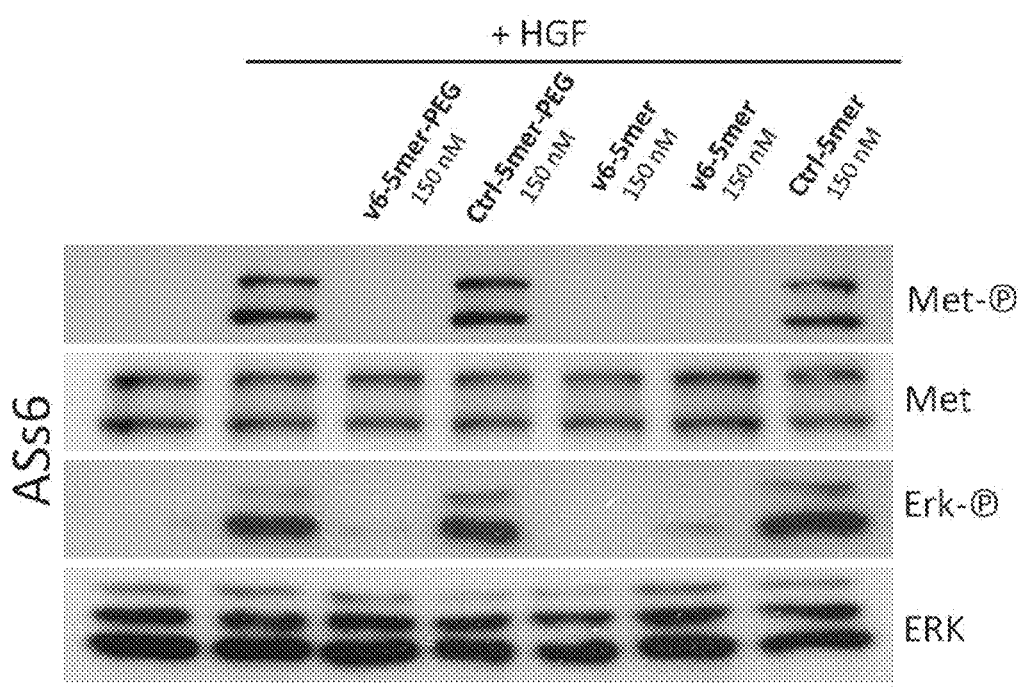
Figure 11:
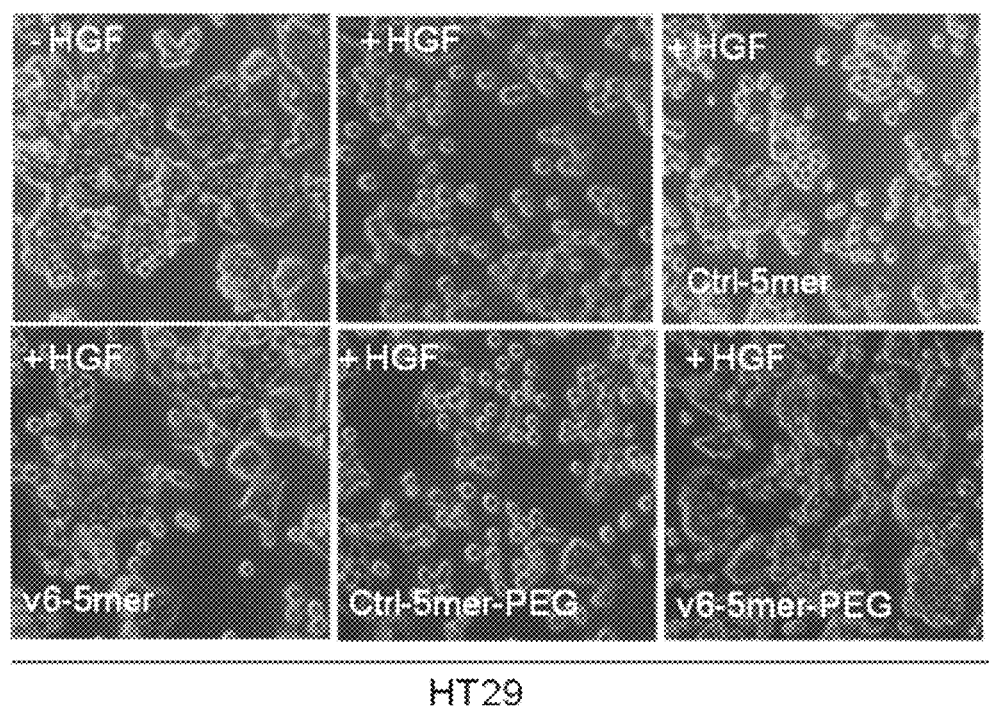
FIG. 11 shows that pegylated as well non-pegylated peptides, but not control peptides lead to dissociation and migration of cells away from these cell cluster.
Figure 13:
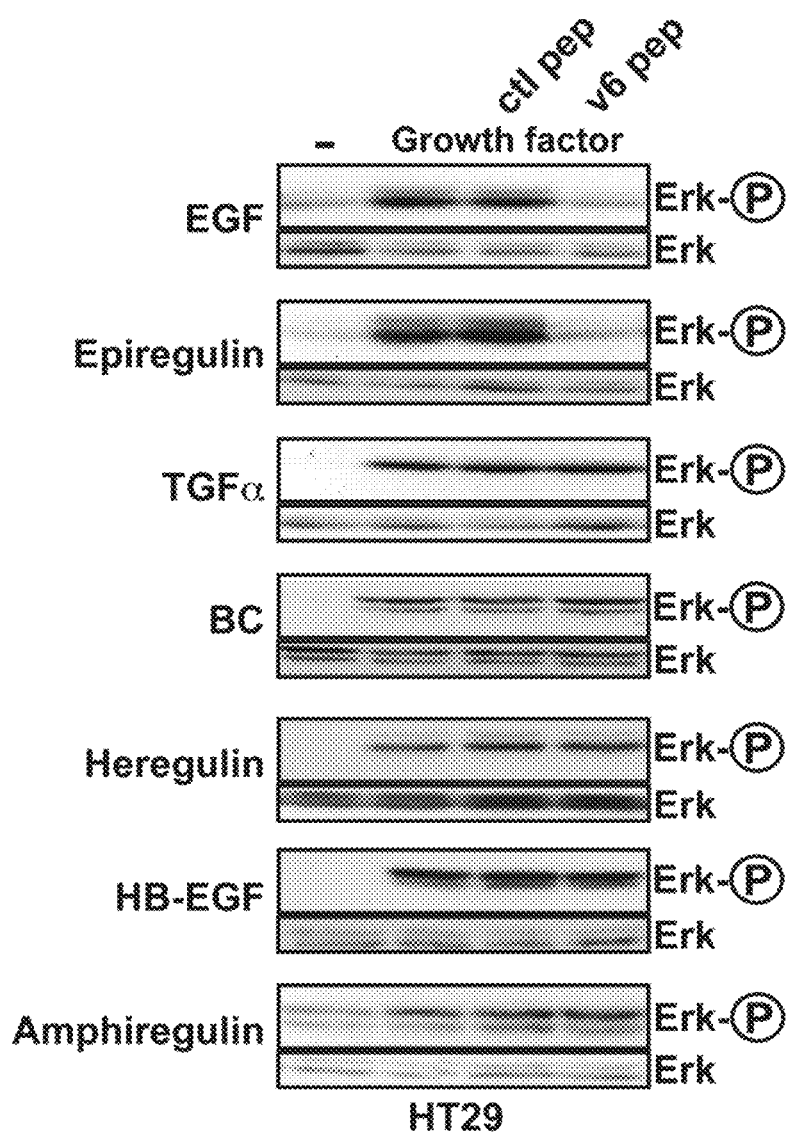

For this purpose HT29 cells were serum-starved for 24 hours and pre-treated with the v6-specific or a control peptide. They were then induced with the indicated ErbB ligands. Erk-kinase phosphorylation was used as a read-out for receptor activation. All ligands could activate the Erk-kinase. EGF- as well as ER-dependent Erk phosphorylation was inhibited by pre-incubation of HT29 cells with the CD44v6 peptide (human v6 14mer) whereas a control peptide showed no effect (FIG. 13).

This shows that, besides EGF, ER is another ErbB1 ligand that is dependent on CD44v6 as a co-receptor. In contrast, AR, BC, HB-EGF and TGF-α-induced activation of the ErbB receptors could not be inhibited by blocking CD44v6 (FIG. 13). These ligands are independent of CD44v6 for their induction of the ErbB receptors. This is especially striking, since EGF and TGF-α address the same receptor pairs (ErbB1/1 or ErbB1/2). These data suggest that the specific CD44 isoform used as a co-receptor for ErbB-activation is determined by the ligand that activates the ErbB receptors and not by the receptor proteins themselves.

Figure 14:
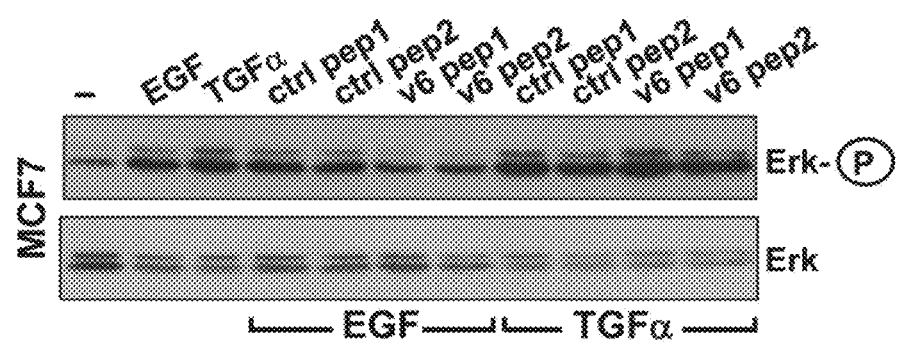

In MCF7 the CD44v6 specific peptides led to the blocking of Erk phosphorylation upon EGF treatment but not upon TGFα induction. Both peptides, the 5mer and 14mer, showed similar effects. The control peptides had no effect on Erk phosphorylation (FIG. 14).

Example 4

1. Dose Reduction and Increase by Linear Peptides and PEGylated v6 5mers

PEGylation, the process of covalent attachment of Poly-EthyleneGlycol polymer chains, is known to reduce immunogenicity and antigenicity. PEGylation increases the hydrodynamic size of the compound and prolongs the circulation time in animals by reducing renal clearance.

Figure 15:
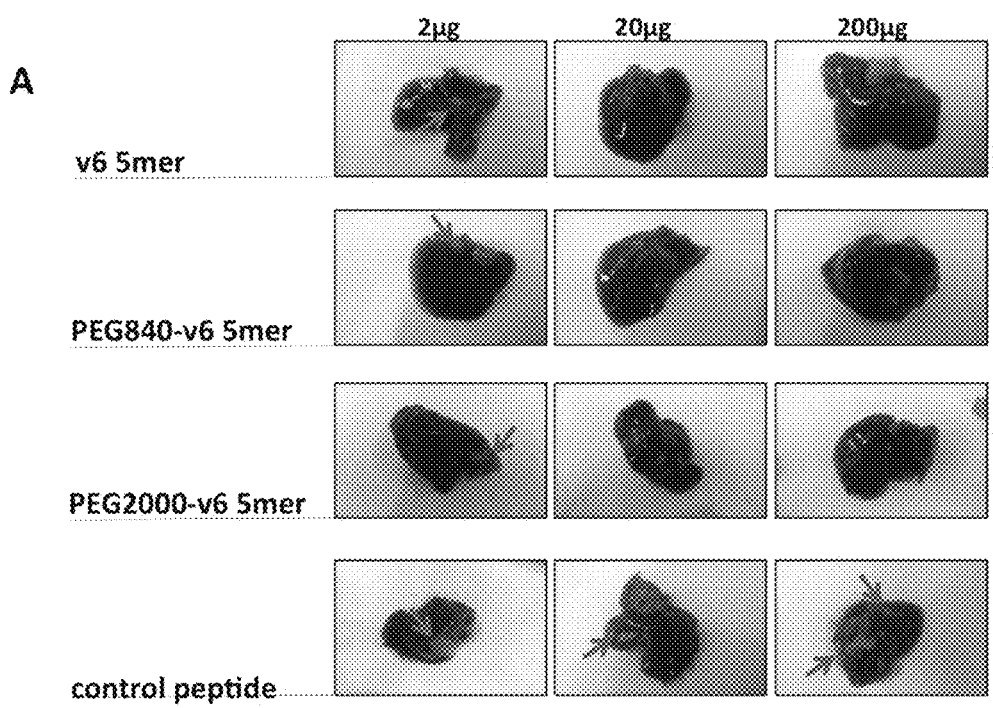
Figure 15:
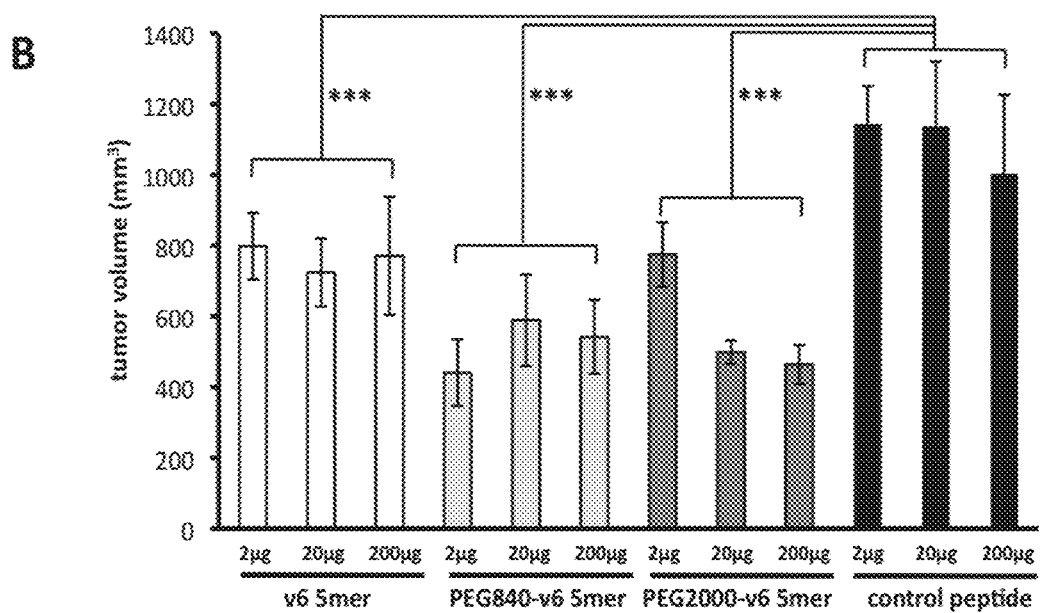

The three CD44v6 specific compounds (v6 5mer, PEG840-v6 5mer and PEG2000-v6 5mer of human origin) and a control peptide were applied in three concentrations (2 µg, 20 µg, 200 µg per injection) three times per week i.p. for 4 weeks. One week before start of the treatment the L3.6p1 tumor cells were orthotopically implanted into nude mice. The results showed that PEGylation has no impact on the effect of the peptides. All v6 specific compounds prevented metastatic spreading of tumor cells and lead to a reduction of primary tumor growth. A complete block of metastasis was observed for 20 µg per injection, however inhibitory effects were already observed using a tenfold lower concentration (FIG. 15). Furthermore an increase of the treatment dose to 200 µg per injection did not lead to side effects in the animals.

2. Results for Reducing the Dose of the Linear v6 14mer and a Cyclic v6 8mer

In this experiment a reduction of the dose of peptides was investigated. The treatment cycle of three injections per week was maintained. Furthermore a cyclic v6 8mer based on the linear sequence containing the three important amino acids that are required for the co-receptor function was tested in vivo for its inhibitory effect. In vitro data showed already blocking of Met and Erk activation in phosphorylation- and cellular assays by all peptides.

Modification of linear peptides by cyclization is achieved by linking the amino and carboxyl termini with a peptide bond that forms a ring. Cyclization is an efficient way to increase the stability of peptides and to improve permeability.

Animals were implanted orthotopically with L3.6p1 cells. Tumor growth was allowed for one week before the treatment with the linear v6 14mer, the cyclic v6 8mer as well as the control peptide (rat v6 14mer) was started. All peptides were injected three times per week at a concentration of 0.2, 2 and 10 µg per injection for 3 weeks. At the end of the treatment animals were sacrificed.

Figure 16:
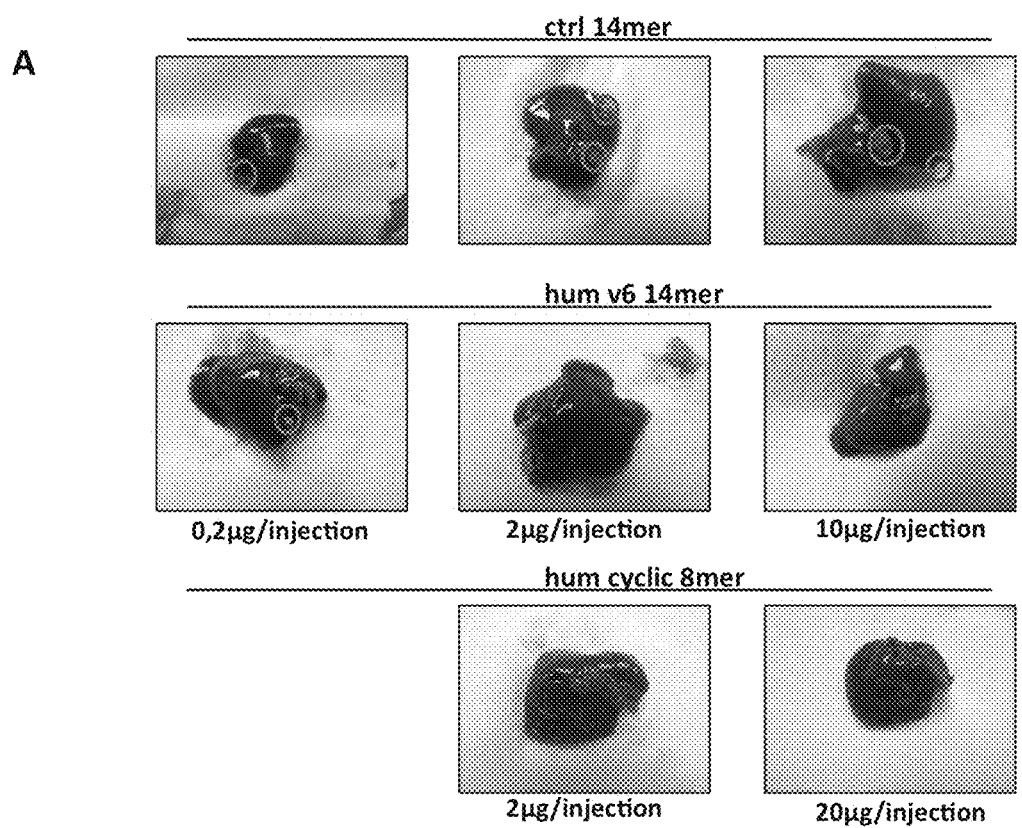
Figure 16:
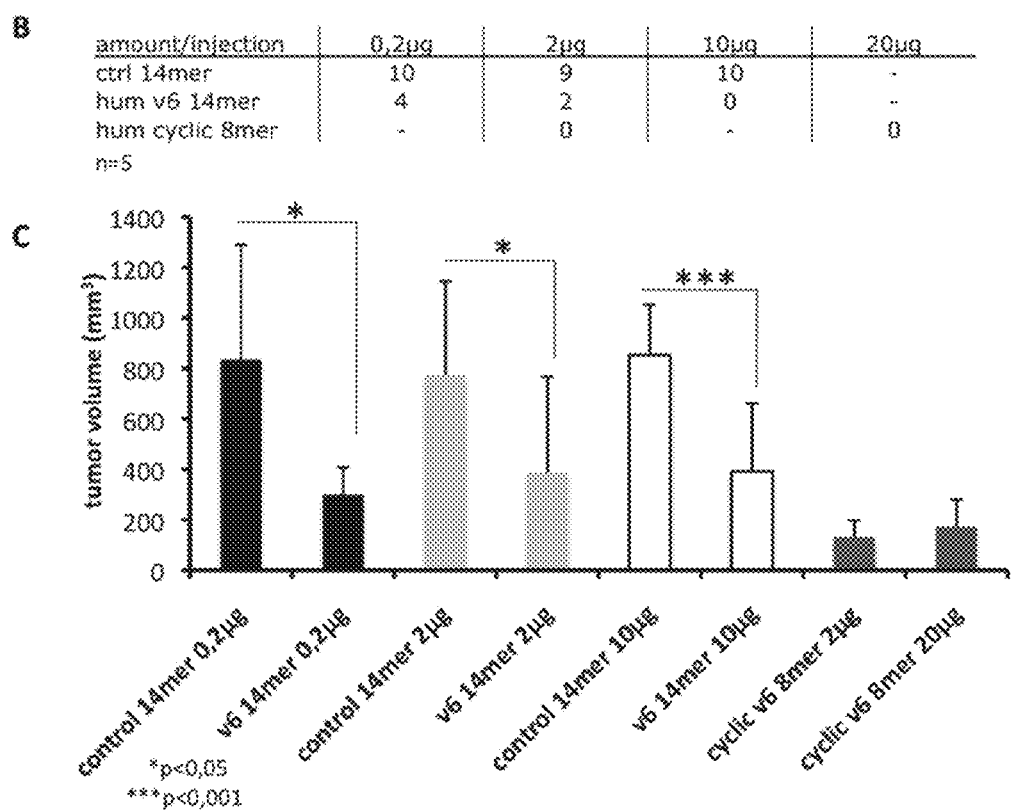

All animals of the control group showed macroscopic metastases. Animals that were injected with 0.2 and 2 µg of v6 14mer showed liver metastases but the average number of metastases per animal was reduced. A dose of 10 μg per injection led to a complete inhibition of metastatic spreading (FIG. 16A, B). Furthermore the treatment with the v6 14mer led to a significant decrease of the size of the primary tumor as compared to the control groups (FIG. 16C).

The cyclic v6 8mer blocked metastatic spreading at 2 and 20 μg per injection very efficiently, indicating that the structural change by cyclization did not lead to loss of function of the peptide (FIG. 16A, B). The cyclic v6 8mer showed also a drastic effect on growth of the primary tumor (FIG. 16C).

3. Side-by-Side Comparison of Different CD44v6 Peptide Derivatives in the L3.6p1 Orthotopic Xenograft Model A comparison of different CD44v6 peptide derivatives was performed in animals bearing a orthotopic L3.6p1 tumor. 10 groups of 5 animals each received a dose of 20 μg peptide per injection three times per week for 3 weeks with the compounds listed in Table 4. Three weeks after starting the treatment the animals were sacrificed and analyzed for macroscopic metastases and tumor volume.

Histological analysis for micrometastasis (H&E staining) and immunohistochemical analysis for tumor vascularization (anti-CD31 staining) and activation of different RTKs in the tumor is still ongoing.

TABLE 4 overview of tested peptide derivatives

| peptide | sequence |
|---|---|
| control (14 mer rat) | H-KEKWFENEWQGANP-OH (SEQ ID NO: 10) |
| PEG840 14-mer | PEG840-KEQWFGNRWHEGYR-OH (SEQ ID NO: 6) |
| PEG2000 14-mer | PEG2000-KEQWFGNRWHEGYR-OH (SEQ ID NO: 6) |
| Myristoyl-14-mer | Myr-KEQWFGNRWHEGYR (SEQ ID NO: 6) |
| 14-mer (human) | H-KEQWFGNRWHEGYR-OH (SEQ ID NO: 6) |
| DOTA CD44v6-14 [daa$_7$] | DOTA-keqwfGNRWHEGyr (SEQ ID NO: 6) |
| DOTA CD44v6-14 [r$^{14}$] | DOTA-KEQWFGNRWHEGYR (SEQ ID NO: 6) |
| cycl. 8 mer | cy[KGNRWHEG](SEQ ID NO: 18) |
| cycl 5 mer | DOTA-cy[KRWHE](SEQ ID NO: 5) |
| Myr-Y-cycl 8 mer | Myr-Y-cy[KGNRWHEG] (SEQ ID NO: 18) |

Figure 17:
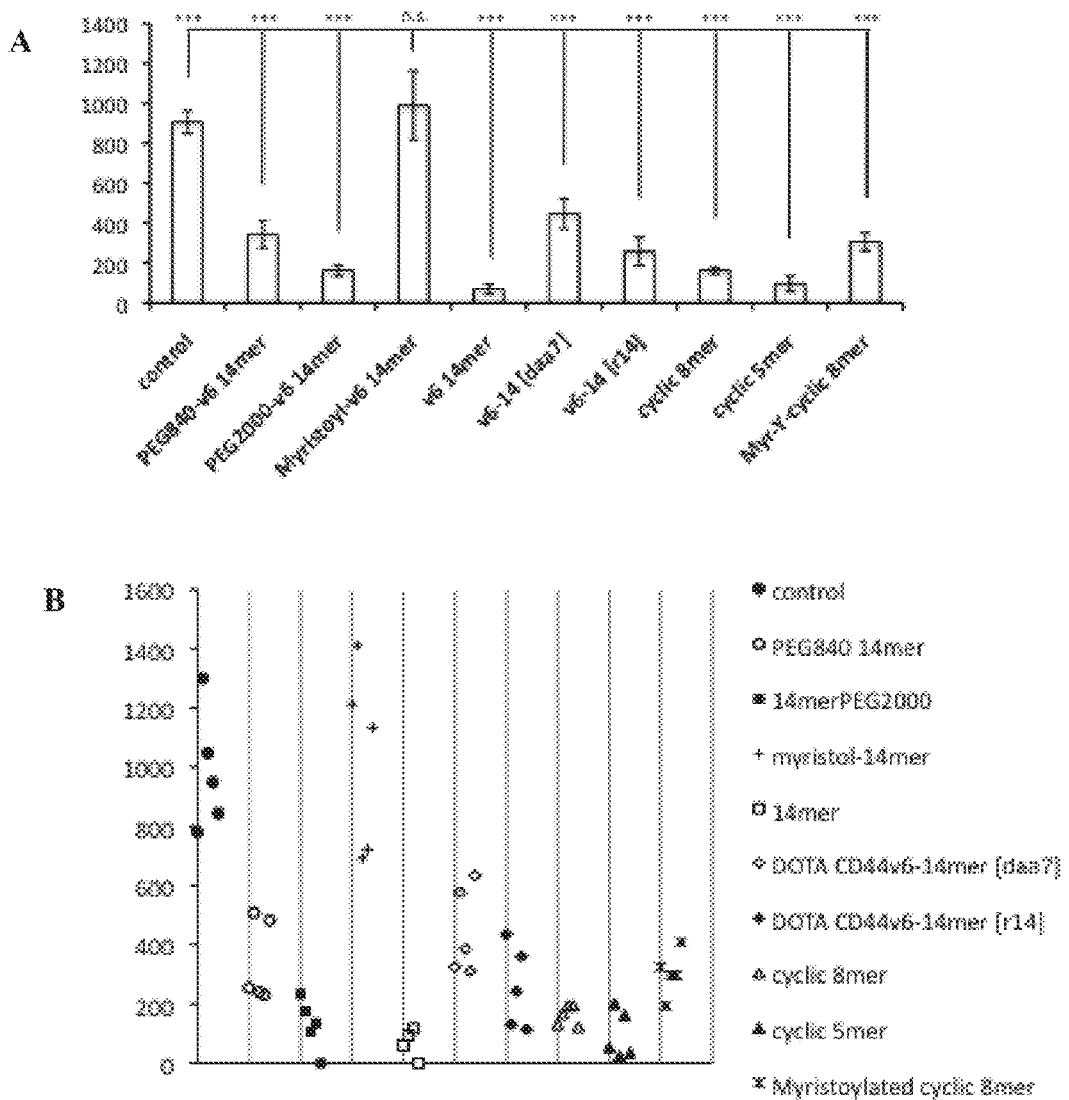

Animals treated with the CD44v6 14mer, the PEGylated 14mer (PEG 840 and PEG 2000), 14mers containing D-amino acid modifications as well as cyclic peptides (including a myristoylated cyclic peptide) showed a significant reduction in tumor growth compared to the control peptide. The myristoylated linear 14mer showed no inhibitory effect on tumor growth. The strongest reduction of tumor size was achieved with the PEG2000 14mer, the v6 14mer, the cyclic 8mer and the cyclic 5mer (FIG. 17A) compared to the control animals (note here the strong visible vascularization of the primary tumor (FIG. 18A)). These four compounds also showed a low variability in the individual tumor size within the group (FIG. 17B).

Figure 18:
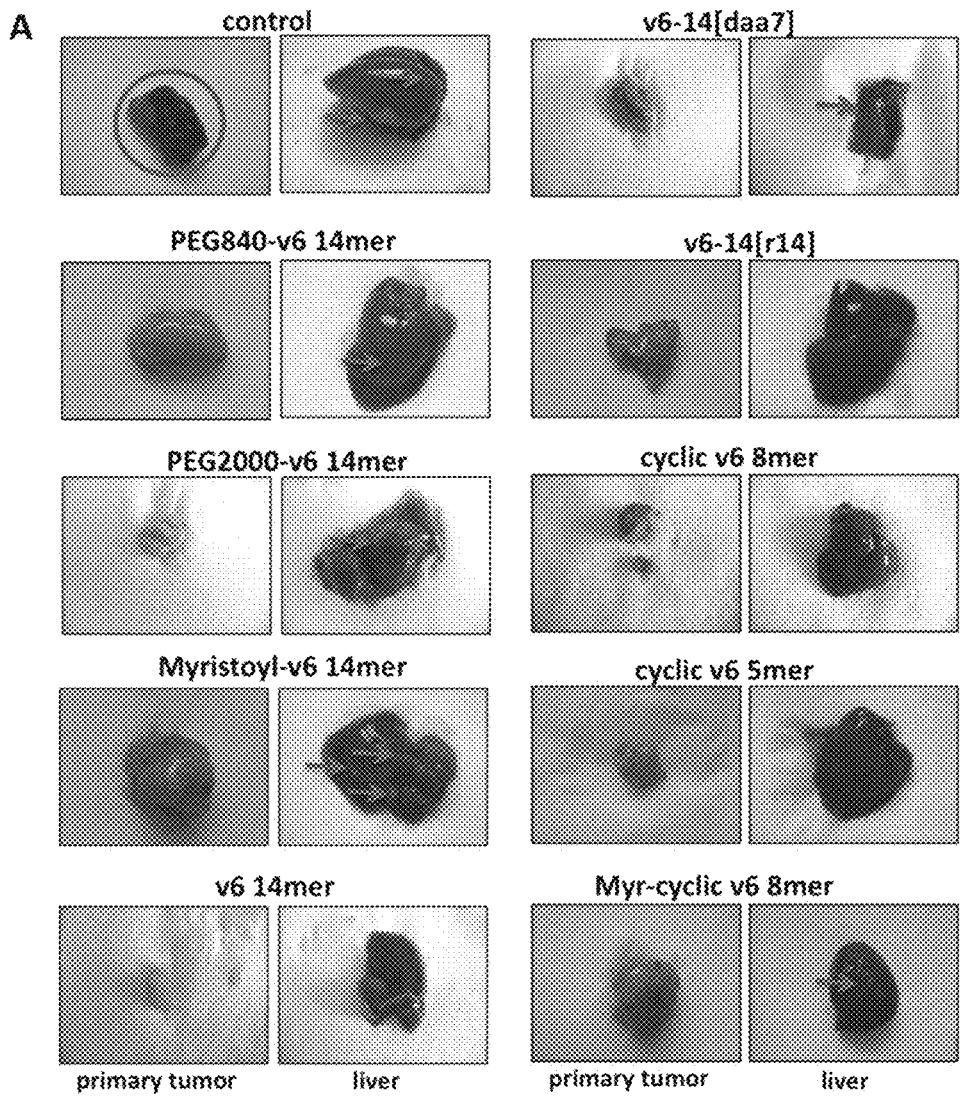

Analysis of the liver showed a decrease of metastatic spreading for PEG840-14mer, PEG2000-14mer v6-14 [daa7] and the myristoylated cyclic 8mer. A complete inhibition of metastasis was observed when animals were treated with the v6 14mer, the v6-14 [r14], the cyclic 8mer and the cyclic 5mer (FIG. 18A, B).

This side-by-side comparison confirmed the efficacy of the v6 14mer but revealed the v6-14 [r14], the cyclic 8mer and the cyclic 5mer as promising modifications of the linear peptide sequence that might show an increased in vivo stability.

Some of the embodiments of the invention relate to:

1. A compound for use in treating pancreatic cancer in a human being,
   wherein said compound comprises:
   a peptide comprising at least the amino acid sequence $X_1$-R-W-H-$X_5$ (SEQ ID NO: 1) with $X_1$ being selected from the group comprising A, C, D, E, F, G, H, I, K, L, M, N, P, Q, R, S, T, V, W, or Y and $X_5$ being selected from the group comprising A, C, D, E, F, G, H, I, K, L, M, N, P, Q, R, S, T, V, W, or Y, or a peptidomimetic thereof, or
   a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 7) wherein $X_1$, $X_2$, $X_3$, $X_4$, $X_5$, $X_6$, $X_7$, $X_{11}$, $X_{12}$, $X_{is}$, or $X_{14}$ is selected from the group comprising A, C, D, E, F, G, H, I, K, L, M, N, P, Q, R, S, T, V, W, or Y, and wherein the peptide comprises at least $X_7$-R-W-H-$X_{11}$ of SEQ ID NO: 7, wherein $X_7$, and $X_{11}$ is selected from the group comprising A, C, D, E, F, G, H, I, K, L, M, N, P, Q, R, S, T, V, W, or Y, or a peptidomimetic thereof.

2. A compound for use of embodiment 1,
   wherein said compound comprises:
   a peptide comprising at least the amino acid sequence $X_1$-R-W-H-$X_5$ (SEQ ID NO: 4) wherein $X_1$ is selected from the group comprising amino acids with an $NH_2$ group such as K, R, N, or Q, or amino acids with non-polar side chains such as A, V, L or I and wherein $X_5$ is selected from the group comprising amino acids with negatively charged side chains such as E or D, or amino acids with non-polar side chains such as A, V, L or I or a peptidomimetic thereof, or
   a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 8), wherein $X_1$ is selected from the group comprising amino acids with an $NH_2$ group such as K, R, N, or Q, or amino acids with non-polar side chains such as A, V, L or I, wherein $X_2$ is selected from the group comprising amino acids with negatively charged side chains such as E or D, or amino acids with non-polar side chains such as A, V, L or I, wherein $X_3$ is selected from the group comprising amino acids with an $NH_2$ group such as K, R, N, or Q, or amino acids with non-polar side chains such as A, V, L or I, wherein $X_4$ is selected from the group comprising amino acids with non-polar or non-charged side chains and aromatic ring structures such as F, W, or Y, or amino acids with non-polar side chains such as A, V, L or I, wherein $X_5$ is selected from the group comprising amino acids with non-polar or non-charged side chains and aromatic rings structures such as F, W, or Y, or amino acids with non-polar side chains such as A, V, L or I, wherein $X_6$ is selected from the group comprising G or amino acids with non-polar side chains such as A, V, L or I, wherein $X_7$ is selected from the group comprising amino acids with an $NH_2$ group such as K, R, N, or Q, or amino acids with non-polar side chains such as A, V, L or I, wherein $X_{11}$ is selected from the group comprising amino acids with negatively charged side chains such as E or D, or amino acids with non-polar side chains such as A, V, L or I, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, or amino acids with non-polar side chains such as A, V, L or I, and wherein $X_{14}$ is selected from the group comprising amino acids with an $NH_2$ group such as K, R, N, or Q, or amino acids with non-polar side chains such as A, V, L or I, and wherein the peptide comprises at least $X_7$-R-W-H-$X_{11}$ of SEQ ID NO: 8, wherein $X_7$ is selected from the group comprising amino acids with an $NH_2$ group such as K, R, N, or Q, or amino acids with non-polar side chains such as A, V, L or I and wherein $X_{11}$ is selected from the group comprising amino acids with negatively charged side chains such as E or D, or amino acids with non-polar side chains such as A, V, L or I, or a peptidomimetic thereof.

3. A compound for use of embodiment 2,
    wherein said compound comprises:
        a peptide comprising at least the amino acid sequence $X_1$-R-W-H-$X_5$ (SEQ ID NO: 5), wherein $X_1$ is selected from the group comprising amino acids with an $NH_2$ group such as K, R, N, or Q, and wherein $X_5$ is selected from the group comprising amino acids with negatively charged side chains such as E or D or a peptidomimetic thereof, or
        a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 9) wherein $X_1$ is selected from the group comprising amino acids with an $NH_2$ group such as K, R, N, or Q, wherein $X_2$ is selected from the group comprising amino acids with negatively charged side chains such as E or D, wherein $X_3$ is selected from the group comprising amino acids with an $NH_2$ group such as K, R, N, or Q, wherein $X_4$ is selected from the group comprising amino acids with non-polar or non-charged side chains and aromatic ring structures such as F, W, or Y, wherein $X_5$ is selected from the group comprising amino acids with non-polar or non-charged side chains and aromatic rings structures such as F, W, or Y, wherein $X_6$ is selected from the group comprising G or amino acids with non-polar side chains such as A, V, L or I, wherein $X_7$ is selected from the group comprising amino acids with an $NH_2$ group such as K, R, N, or Q, wherein $X_{11}$ is selected from the group comprising amino acids with negatively charged side chains such as E or D, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, and wherein $X_{14}$ is selected from the group comprising amino acids with an $NH_2$ group such as K, R, N, or Q, and wherein the peptide comprises at least $X_7$-R-W-H-$X_{11}$ of SEQ ID NO: 9, wherein $X_7$ is selected from the group comprising amino acids with an $NH_2$ group such as K, R, N, or Q and wherein $X_{11}$ is selected from the group comprising amino acids with negatively charged side chains such as E or D, or a peptidomimetic thereof.

4. A compound for use of embodiment 1, 2, or 3
    wherein said compound comprises a peptide comprising, optionally consisting of, the amino acid sequence N-R-W-H-E (SEQ ID NO: 2), amino acid sequence K-E-Q-W-F-G-N—R-W-H-E-G-Y-R (SEQ ID NO: 6), or a peptidomimetic thereof.

5. A compound for use of embodiment 1, 2, 3, or 4,
    wherein said compound is a modified form of said peptide or said peptidomimetic.

6. A compound for use of embodiment 5,
    wherein said compound is a pegylated, hesylated, pasylated, myristoylated, glycosylated, and/or cyclic form of said peptide or peptidomimetic.

7. A compound for use of embodiment 1, 2, 3, 4, or 5,
    wherein the compound is formulated for oral, nasal, or subcutaneous administration.

8. A pharmaceutical composition for use in treating pancreatic cancer in a human being,
    wherein said pharmaceutical composition comprises a compound comprising:
        a peptide comprising at least the amino acid sequence $X_1$-R-W-H-$X_5$ (SEQ ID NO: 1) with $X_1$ being selected from the group comprising A, C, D, E, F, G, H, I, K, L, M, N, P, Q, R, S, T, V, W, or Y and $X_5$ being selected from the group comprising A, C, D, E, F, G, H, I, K, L, M, N, P, Q, R, S, T, V, W, or Y, or a peptidomimetic thereof, or
        a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 7), wherein $X_1$, $X_2$, $X_3$, $X_4$, $X_5$, $X_6$, $X_7$, $X_{11}$, $X_{12}$, $X_{13}$, or $X_{14}$ is selected from the group comprising A, C, D, E, F, G, H, I, K, L, M, N, P, Q, R, S, T, V, W, or Y, and wherein the peptide comprises at least $X_7$-R-W-H-$X_{11}$ of SEQ ID NO: 7, wherein $X_7$, and $X_{11}$ is selected from the group comprising A, C, D, E, F, G, H, I, K, L, M, N, P, Q, R, S, T, V, W, or Y, or a peptidomimetic thereof.

9. A pharmaceutical composition for use of embodiment 8,
    wherein said pharmaceutical composition comprises a compound comprising:
        a peptide comprising at least the amino acid sequence $X_1$-R-W-H-$X_5$ (SEQ ID NO: 4), wherein $X_1$ is selected from the group comprising amino acids with an $NH_2$ group such as K, R, N, or Q, or amino acids with non-polar side chains such as A, V, L or I and wherein $X_5$ is selected from the group comprising amino acids with negatively charged side chains such as E or D, or amino acids with non-polar side chains such as A, V, L or I or a peptidomimetic thereof, or
        a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 8), wherein $X_1$ is selected from the group comprising amino acids with an $NH_2$ group such as K, R, N, or Q, or amino acids with non-polar side chains such as A, V, L or I, wherein $X_2$ is selected from the group comprising amino acids with negatively charged side chains such as E or D, or amino acids with non-polar side chains such as A, V, L or I, wherein $X_3$ is selected from the group comprising amino acids with an $NH_2$ group such as K, R, N, or Q, or amino acids with non-polar side chains such as A, V, L or I, wherein $X_4$ is selected from the group comprising amino acids with non-polar or non-charged side chains and aromatic ring structures such as F, W, or Y, or amino acids with non-polar side chains such as A, V, L or I, wherein $X_5$ is selected from the group comprising amino acids with non-polar or non-charged side chains and aromatic rings structures such as F, W, or Y, or amino acids with non-polar side chains such as A, V, L or I, wherein $X_6$ is selected from the group comprising G or amino acids with non-polar side chains such as A, V, L or I, wherein $X_7$ is selected from the group comprising amino acids with an $NH_2$ group such as K, R, N, or Q, or amino acids with non-polar side chains such as A, V, L or I, wherein $X_{11}$ is selected from the group comprising amino acids with negatively charged side chains such as E or D, or amino acids with non-polar side chains such as A, V, L or I, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, or amino acids with non-polar side chains such as A, V, L or I, and wherein $X_{14}$ is selected from the group comprising amino acids with an $NH_2$ group such as K, R, N, or Q, or amino acids with non-polar side chains such as A, V, L or I, and wherein the peptide comprises at least $X_7$-R-W-H-$X_{11}$ of SEQ ID NO: 8, wherein $X_7$ is selected from the group comprising amino acids with an $NH_2$ group such as K, R, N, or Q, or amino acids with non-polar side chains such as A, V, L or I and wherein $X_{11}$ is selected from the group comprising amino acids with negatively charged side chains such as E or D, or amino acids with non-polar side chains such as A, V, L or I, or a peptidomimetic thereof.

10. A pharmaceutical composition for use of embodiment 9, wherein said pharmaceutical composition comprises a compound comprising:
a peptide comprising at least the amino acid sequence $X_1$-R-W-H-$X_5$ (SEQ ID NO: 5), wherein $X_1$ is selected from the group comprising amino acids with an $NH_2$ group such as K, R, N, or Q, and wherein $X_5$ is selected from the group comprising amino acids with negatively charged side chains such as E or D, or a peptidomimetic thereof, or
a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 9), wherein $X_1$ is selected from the group comprising amino acids with an $NH_2$ group such as K, R, N, or Q, wherein $X_2$ is selected from the group comprising amino acids with negatively charged side chains such as E or D, wherein $X_3$ is selected from the group comprising amino acids with an $NH_2$ group such as K, R, N, or Q, wherein $X_4$ is selected from the group comprising amino acids with non-polar or non-charged side chains and aromatic ring structures such as F, W, or Y, wherein $X_5$ is selected from the group comprising amino acids with non-polar or non-charged side chains and aromatic rings structures such as F, W, or Y, wherein $X_6$ is selected from the group comprising G or amino acids with non-polar side chains such as A, V, L or I, wherein $X_7$ is selected from the group comprising amino acids with an $NH_2$ group such as K, R, N, or Q, wherein $X_{11}$ is selected from the group comprising amino acids with negatively charged side chains such as E or D, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, and wherein $X_{14}$ is selected from the group comprising amino acids with an $NH_2$ group such as K, R, N, or Q, and wherein the peptide comprises at least $X_7$-R-W-H-$X_{11}$ of SEQ ID NO: 9, wherein $X_7$ is selected from the group comprising amino acids with an $NH_2$ group such as K, R, N, or Q and wherein $X_{11}$ is selected from the group comprising amino acids with negatively charged side chains such as E or D, or a peptidomimetic thereof.

11. A pharmaceutical composition for use of embodiment 8, 9, or 10,
wherein said compound comprises a peptide comprising, optionally consisting of, amino acid sequence N-R-W-H-E (SEQ ID NO: 2), amino acid sequence K-E-Q-W-F-G-N—R-W-H-E-G-Y-R (SEQ ID NO: 6), or a peptidomimetic thereof.

12. A pharmaceutical composition for use of embodiment 8, 9, 10, or 11,
wherein said compound is a modified form of said peptide or said peptidomimetic.

13. A pharmaceutical composition for use of embodiment 12,
wherein said compound is a pegylated, hesylated, pasylated, myristoylated, glycosylated, and/or cyclic form of said peptide or peptidomimetic.

14. A pharmaceutical composition for use of embodiment 8, 9, 10, 11, 12, or 13,
wherein said pharmaceutical composition comprises a pharmaceutically acceptable excipient.

15. A pharmaceutical composition for use of embodiment 8, 9, 10, 11, 12, 13 or 14,
wherein said pharmaceutical composition is formulated for oral, nasal, or subcutaneous administration.

16. Use of a compound in the manufacture of a medicament for use in treating pancreatic cancer in a human being,
wherein said compound comprises:
a peptide comprising at least the amino acid sequence $X_1$-R-W-H-$X_5$ (SEQ ID NO: 1) with $X_1$ being selected from the group comprising A, C, D, E, F, G, H, I, K, L, M, N, P, Q, R, S, T, V, W, or Y and $X_5$ being selected from the group comprising A, C, D, E, F, G, H, I, K, L, M, N, P, Q, R, S, T, V, W, or Y, or a peptidomimetic thereof, or
a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 7), wherein $X_1$, $X_2$, $X_3$, $X_4$, $X_5$, $X_6$, $X_7$, $X_{11}$, $X_{12}$, $X_{13}$, or $X_{14}$ is selected from the group comprising A, C, D, E, F, G, H, I, K, L, M, N, P, Q, R, S, T, V, W, or Y, and wherein the peptide comprises at least $X_7$-R-W-H-$X_{11}$ of SEQ ID NO: 7, wherein $X_7$, and $X_{11}$ is selected from the group comprising A, C, D, E, F, G, H, I, K, L, M, N, P, Q, R, S, T, V, W, or Y, or a peptidomimetic thereof.

17. Use of a compound of embodiment 16,
wherein said compound comprises:
a peptide comprising at least the amino acid sequence $X_1$-R-W-H-$X_5$ (SEQ ID NO: 4), wherein $X_1$ is selected from the group comprising amino acids with an NH$_2$ group such as K, R, N, or Q, or amino acids with non-polar side chains such as A, V, L or I and wherein X$_5$ is selected from the group comprising amino acids with negatively charged side chains such as E or D, or amino acids with non-polar side chains such as A, V, L or I or a peptidomimetic thereof, or a peptide comprising at least 5, 6, 7, 8, 9, 10, 11, 12, 13, or 14 amino acids of amino acid sequence X$_1$-X$_2$-X$_3$-X$_4$-X$_5$-X$_6$-X$_7$-R-W-H-X$_{11}$-X$_{12}$-X$_{13}$-X$_{14}$ (SEQ ID NO: 8), wherein X$_1$ is selected from the group comprising amino acids with an NH$_2$ group such as K, R, N, or Q, or amino acids with non-polar side chains such as A, V, L or I, wherein X$_2$ is selected from the group comprising amino acids with negatively charged side chains such as E or D, or amino acids with non-polar side chains such as A, V, L or I, wherein X$_3$ is selected from the group comprising amino acids with an NH$_2$ group such as K, R, N, or Q, or amino acids with non-polar side chains such as A, V, L or I, wherein X$_4$ is selected from the group comprising amino acids with non-polar or non-charged side chains and aromatic ring structures such as F, W, or Y, or amino acids with non-polar side chains such as A, V, L or I, wherein X$_5$ is selected from the group comprising amino acids with non-polar or non-charged side chains and aromatic rings structures such as F, W, or Y, or amino acids with non-polar side chains such as A, V, L or I, wherein X$_6$ is selected from the group comprising G or amino acids with non-polar side chains such as A, V, L or I, wherein X$_7$ is selected from the group comprising amino acids with an NH$_2$ group such as K, R, N, or Q, or amino acids with non-polar side chains such as A, V, L or I, wherein X$_{11}$ is selected from the group comprising amino acids with negatively charged side chains such as E or D, or amino acids with non-polar side chains such as A, V, L or I, wherein X$_{12}$ is selected from the group comprising G or amino acids with non-polar side chains such as A, V, L or I, wherein X$_{13}$ is selected from the group comprising amino acids with non-polar or non-charged side chains and aromatic rings structures such F, W, or Y, or amino acids with non-polar side chains such as A, V, L or I, and wherein X$_{14}$ is selected from the group comprising amino acids with an NH$_2$ group such as K, R, N, or Q, or amino acids with non-polar side chains such as A, V, L or I, and wherein the peptide comprises at least X$_7$-R-W-H-X$_{11}$ of SEQ ID NO: 8, wherein X$_7$ is selected from the group comprising amino acids with an NH$_2$ group such as K, R, N, or Q, or amino acids with non-polar side chains such as A, V, L or I and wherein X$_{11}$ is selected from the group comprising amino acids with negatively charged side chains such as E or D, or amino acids with non-polar side chains such as A, V, L or I, or a peptidomimetic thereof.

18. Use of a compound of embodiment 17, wherein said compound comprises:

a peptide comprising at least the amino acid sequence X$_1$-R-W-H-X$_5$ (SEQ ID NO: 5), wherein X$_1$ is selected from the group comprising amino acids with an NH$_2$ group such as K, R, N, or Q, and wherein X$_5$ is selected from the group comprising amino acids with negatively charged side chains such as E or D, or a peptidomimetic thereof, or a peptide comprising at least 5, 6, 7, 8, 9, 10, 11, 12, 13, or 14 amino acids of amino acid sequence X$_1$-X$_2$-X$_3$-X$_4$-X$_5$-X$_6$-X$_7$-R-W-H-X$_{11}$-X$_{12}$-X$_{13}$-X$_{14}$ (SEQ ID NO: 9), wherein X$_1$ is selected from the group comprising amino acids with an NH$_2$ group such as K, R, N, or Q, wherein X$_2$ is selected from the group comprising amino acids with negatively charged side chains such as E or D, wherein X$_3$ is selected from the group comprising amino acids with an NH$_2$ group such as K, R, N, or Q, wherein X$_4$ is selected from the group comprising amino acids with non-polar or non-charged side chains and aromatic ring structures such as F, W, or Y, wherein X$_5$ is selected from the group comprising amino acids with non-polar or non-charged side chains and aromatic rings structures such as F, W, or Y, wherein X$_6$ is selected from the group comprising G or amino acids with non-polar side chains such as A, V, L or I, wherein X$_7$ is selected from the group comprising amino acids with an NH$_2$ group such as K, R, N, or Q, wherein X$_{11}$ is selected from the group comprising amino acids with negatively charged side chains such as E or D, wherein X$_{12}$ is selected from the group comprising G or amino acids with non-polar side chains such as A, V, L or I, wherein X$_{13}$ is selected from the group comprising amino acids with non-polar or non-charged side chains and aromatic rings structures such F, W, or Y, and wherein X$_{14}$ is selected from the group comprising amino acids with an NH$_2$ group such as K, R, N, or Q, and wherein the peptide comprises at least X$_7$-R-W-H-X$_{11}$ of SEQ ID NO: 9, wherein X$_7$ is selected from the group comprising amino acids with an NH$_2$ group such as K, R, N, or Q and wherein X$_{11}$ is selected from the group comprising amino acids with negatively charged side chains such as E or D, or a peptidomimetic thereof.

19. Use of a compound of embodiment 16, 17, or 18, wherein said compound comprises a peptide comprising, optionally consisting of, amino acid sequence N-R-W-H-E (SEQ ID NO: 2), amino acid sequence K-E-Q-W-F-G-N—R-W-H-E-G-Y-R (SEQ ID NO: 6), or a peptidomimetic thereof.

20. Use of a compound of embodiment 16, 17, 18, or 19, wherein said compound is a modified form of said peptide or said peptidomimetic.

21. Use of a compound of embodiment 20, wherein said compound is a pegylated, hesylated, pasylated, glycosylated, myristoylated, and/or cyclic form of said peptide or peptidomimetic.

22. Use of a compound of embodiment 16, 17, 18, 19, 20, or 21, wherein said medicament is formulated for oral, nasal, or subcutaneous administration.

23. Method of treating pancreatic cancer in a human being by administering a compound, wherein said compound comprises:

a peptide comprising at least the amino acid sequence X$_1$-R-W-H-X$_5$ (SEQ ID NO: 1) with X$_1$ being selected from the group comprising A, C, D, E, F, G, H, I, K, L, M, N, P, Q, R, S, T, V, W, or Y and X$_5$ being selected from the group comprising A, C, D, E, F, G, H, I, K, L, M, N, P, Q, R, S, T, V, W, or Y, or a peptidomimetic thereof, or a peptide comprising at least 5, 6, 7, 8, 9, 10, 11, 12, 13, or 14 amino acids of amino acid sequence X$_1$-X$_2$-X$_3$-X$_4$-X$_5$-X$_6$-X$_7$-R-W-H-X$_{11}$-X$_{12}$-X$_{13}$-X$_{14}$ (SEQ ID NO: 7), wherein X$_1$, X$_2$, X$_3$, X$_4$, X$_5$, X$_6$, X$_7$, X$_{11}$, X$_{12}$, X$_{13}$, or $X_{14}$ is selected from the group comprising A, C, D, E, F, G, H, I, K, L, M, N, P, Q, R, S, T, V, W, or Y, and wherein the peptide comprises at least $X_7$-R-W-H-$X_{11}$ of SEQ ID NO: 7, wherein $X_7$, and $X_{11}$ is selected from the group comprising A, C, D, E, F, G, H, I, K, L, M, N, P, Q, R, S, T, V, W, or Y, or a peptidomimetic thereof.

24. Method of embodiment 23,
    wherein said compound comprises:
        a peptide comprising at least the amino acid sequence $X_1$-R-W-H-$X_5$ (SEQ ID NO: 4), wherein $X_1$ is selected from the group comprising amino acids with an $NH_2$ group such as K, R, N, or Q, or amino acids with non-polar side chains such as A, V, L or I and wherein $X_5$ is selected from the group comprising amino acids with negatively charged side chains such as E or D, or amino acids with non-polar side chains such as A, V, L or I or a peptidomimetic thereof, or
        a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 8), wherein $X_1$ is selected from the group comprising amino acids with an $NH_2$ group such as K, R, N, or Q, or amino acids with non-polar side chains such as A, V, L or I, wherein $X_2$ is selected from the group comprising amino acids with negatively charged side chains such as E or D, or amino acids with non-polar side chains such as A, V, L or I, wherein $X_3$ is selected from the group comprising amino acids with an $NH_2$ group such as K, R, N, or Q, or amino acids with non-polar side chains such as A, V, L or I, wherein $X_4$ is selected from the group comprising amino acids with non-polar or non-charged side chains and aromatic ring structures such as F, W, or Y, or amino acids with non-polar side chains such as A, V, L or I, wherein $X_5$ is selected from the group comprising amino acids with non-polar or non-charged side chains and aromatic rings structures such as F, W, or Y, or amino acids with non-polar side chains such as A, V, L or I, wherein $X_6$ is selected from the group comprising G or amino acids with non-polar side chains such as A, V, L or I, wherein $X_7$ is selected from the group comprising amino acids with an $NH_2$ group such as K, R, N, or Q, or amino acids with non-polar side chains such as A, V, L or I, wherein $X_{11}$ is selected from the group comprising amino acids with negatively charged side chains such as E or D, or amino acids with non-polar side chains such as A, V, L or I, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, or amino acids with non-polar side chains such as A, V, L or I, and wherein $X_{14}$ is selected from the group comprising amino acids with an $NH_2$ group such as K, R, N, or Q, or amino acids with non-polar side chains such as A, V, L or I, and wherein the peptide comprises at least $X_7$-R-W-H-$X_{11}$ of SEQ ID NO: 8, wherein $X_7$ is selected from the group comprising amino acids with an $NH_2$ group such as K, R, N, or Q, or amino acids with non-polar side chains such as A, V, L or I and wherein $X_{11}$ is selected from the group comprising amino acids with negatively charged side chains such as E or D, or amino acids with non-polar side chains such as A, V, L or I, or a peptidomimetic thereof.

25. Method of embodiment 24,
    wherein said compound comprises:
        a peptide comprising at least the amino acid sequence $X_1$-R-W-H-$X_5$ (SEQ ID NO: 5), wherein $X_1$ is selected from the group comprising amino acids with an $NH_2$ group such as K, R, N, or Q, and wherein $X_5$ is selected from the group comprising amino acids with negatively charged side chains such as E or D, or a peptidomimetic thereof, or
        a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 9), wherein $X_1$ is selected from the group comprising amino acids with an $NH_2$ group such as K, R, N, or Q, wherein $X_2$ is selected from the group comprising amino acids with negatively charged side chains such as E or D, wherein $X_3$ is selected from the group comprising amino acids with an $NH_2$ group such as K, R, N, or Q, wherein $X_4$ is selected from the group comprising amino acids with non-polar or non-charged side chains and aromatic ring structures such as F, W, or Y, wherein $X_5$ is selected from the group comprising amino acids with non-polar or non-charged side chains and aromatic rings structures such as F, W, or Y, wherein $X_6$ is selected from the group comprising G or amino acids with non-polar side chains such as A, V, L or I, wherein $X_7$ is selected from the group comprising amino acids with an $NH_2$ group such as K, R, N, or Q, wherein $X_{11}$ is selected from the group comprising amino acids with negatively charged side chains such as E or D, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, and wherein $X_{14}$ is selected from the group comprising amino acids with an $NH_2$ group such as K, R, N, or Q, and wherein the peptide comprises at least $X_7$-R-W-H-$X_{11}$ of SEQ ID NO: 9, wherein $X_7$ is selected from the group comprising amino acids with an $NH_2$ group such as K, R, N, or Q and wherein $X_{11}$ is selected from the group comprising amino acids with negatively charged side chains such as E or D, or a peptidomimetic thereof.

26. Method of embodiment 23, 24, or 25,
    wherein said compound comprises a peptide comprising, optionally consisting of, amino acid sequence N-R-W-H-E (SEQ ID NO: 2), amino acid sequence K-E-Q-W-F-G-N—R-W-H-E-G-Y-R (SEQ ID NO: 6), or a peptidomimetic thereof.

27. Method of embodiment 23, 24, 25, or 26,
    wherein said compound is a modified form of said peptide or said peptidomimetic.

28. Method of embodiment 27,
    wherein said compound is a pegylated, hesylated, pasylated, glycosylated, myristoylated, or cyclic form of said peptide or peptidomimetic.

29. Method of embodiment 23, 24, 25, 26, 27, or 28,
    wherein said compound is formulated for oral, nasal, or subcutaneous administration.

30. Compound for use of any of embodiments 1, 2, 3, 4, 5, 6 or 7, a pharmaceutical composition for use of any of embodiments 8, 9, 10, 11, 12, 13, 14, or 15, use of any of embodiments 16, 17, 18, 19, 20, 21 or 22 or method of any of embodiments 23, 24, 25, 26, 27, 28, or 29,
wherein said pancreatic cancer has not yet formed metastases.

31. Compound for use of any of embodiments 1, 2, 3, 4, 5, 6 or 7, a pharmaceutical composition for use of any of embodiments 8, 9, 10, 11, 12, 13, 14, or 15, use of any of embodiments 16, 17, 18, 19, 20, 21 or 22 or method of any of embodiments 23, 24, 25, 26, 27, 28, or 29,
wherein said pancreatic cancer has already formed metastases.

32. Compound for use of any of embodiments 1, 2, 3, 4, 5, 6 or 7, a pharmaceutical composition for use of any of embodiments 8, 9, 10, 11, 12, 13, 14, or 15, use of any of embodiments 16, 17, 18, 19, 20, 21 or 22 or method of any of embodiments 23, 24, 25, 26, 27, 28, or 29,
wherein said pancreatic cancer is classifiable as Stage IV according to the TNM anatomic/prognostic group system of the cancer staging system of the American Joint Committee on Cancer.

33. Compound for use, Pharmaceutical composition for use, use, or method of any of embodiments 30, 31, or 32,
wherein the pancreatic cancer is an exocrine or endocrine pancreatic cancer.

The invention claimed is:

1. A method for inhibiting pancreatic cancer tumor growth in a human being, comprising administering a compound to the human being in need thereof, wherein said compound comprises:
   (i) a peptide comprising at least the amino acid sequence $X_1$-R-W-H-$X_5$ (SEQ ID NO:1) with $X_1$ being an amino acid selected from the group consisting of A, C, D, E, F, G, H, I, K, L, M, N, P, Q, R, S, T, V, W, or Y and $X_5$ being an amino acid selected from the group consisting of A, C, D, E, F, G, H, I, K, L, M, N, P, Q, R, S, T, V, W, and Y or a peptidomimetic thereof, or
   (ii) a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO:7), wherein $X_1$, $X_2$, $X_3$, $X_4$, $X_5$, $X_6$, $X_7$, $X_{11}$, $X_{12}$, $X_{13}$, or $X_{14}$ is an amino acid selected from the group consisting of A, C, D, E, F, G, H, I, K, L, M, N, P, Q, R, S, T, V, W, and Y and wherein the peptide comprises at least $X_7$-R-W-H-$X_{11}$ of SEQ ID NO: 7, wherein $X_7$ or $X_{11}$ is an amino acid selected from the group consisting of A, C, D, E, F, G, H, I, K, L, M, N, P, Q, R, S, T, V, W, and Y, or a peptidomimetic thereof,
   wherein said pancreatic cancer is classifiable as Stage IV according to the Tumor Node Metastasis (TNM) anatomic/prognostic group system of the cancer staging system of the American Joint Committee on Cancer.

2. The method of claim 1, wherein said compound comprises:
   (i) a peptide comprising at least the amino acid sequence $X_1$-R-W-H-$X_5$ (SEQ ID NO:4), wherein $X_1$ is an amino acid selected from the group consisting of amino acids with an $NH_2$ group side chain and amino acids with non-polar side chains, and wherein $X_5$ is an amino acid selected from the group consisting of amino acids with negatively charged side chains and amino acids with non-polar side chains or a peptidomimetic thereof, or
   (ii) a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 8), wherein $X_1$ is an amino acid selected from the group consisting of amino acids with an $NH_2$ group side chain and amino acids with non-polar side chains, wherein $X_2$ is an amino acid selected from the group consisting of amino acids with negatively charged side chains and amino acids with non-polar side chains, wherein $X_3$ is an amino acid selected from the group consisting of amino acids with an $NH_2$ group side chain and amino acids with non-polar side chains, wherein $X_4$ is an amino acid selected from the group consisting of amino acids with non-polar or non-charged side chains, aromatic ring structures and amino acids with non-polar side chains, wherein $X_5$ is an amino acid selected from the group consisting of amino acids with non-polar or non-charged side chains, aromatic rings structures and amino acids with non-polar side chains, wherein $X_6$ is an amino acid selected from the group consisting of G and amino acids with non-polar side chains, wherein $X_7$ is an amino acid selected from the group consisting of amino acids with an $NH_2$ group side chain and amino acids with non-polar side chains, wherein $X_{11}$ is an amino acid selected from the group consisting of amino acids with negatively charged side chains and or amino acids with non-polar side chains, wherein $X_{12}$ is an amino acid selected from the group consisting of G and amino acids with non-polar side chains, wherein $X_{13}$ is an amino acid selected from the group consisting of amino acids with non-polar or non-charged side chains, aromatic ring structures and amino acids with non-polar side chains, and wherein $X_{14}$ is an amino acid selected from the group consisting of amino acids with an $NH_2$ group side chain and amino acids with non-polar side chains, and wherein the peptide comprises at least $X_7$-R-W-H-$X_{11}$ of SEQ ID NO: 8, wherein $X_7$ is an amino acid selected from the group consisting of amino acids with an $NH_2$ group side chain and amino acids with non-polar side chains, and wherein $X_{11}$ is an amino acid selected from the group consisting of amino acids with negatively charged side chains and amino acids with non-polar side chains, or a peptidomimetic thereof.

3. The method of claim 1, wherein said compound comprises:
   i. a peptide comprising at least the amino acid sequence $X_1$-R-W-H-$X_5$ (SEQ ID NO: 5), wherein $X_1$ is an amino acid selected from the group consisting of amino acids with an $NH_2$ group side chain, and wherein $X_5$ is an amino acid selected from the group consisting of amino acids with negatively charged side chains or a peptidomimetic thereof, or
   ii. a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 9), wherein $X_1$ is an amino acid selected from the group consisting of amino acids with an $NH_2$ group side chain, wherein $X_2$ is an amino acid selected from the group consisting of amino acids with negatively charged side chains, wherein $X_3$ is an amino acid selected from the group consisting of amino acids with an $NH_2$ group side chain, wherein $X_4$ is an amino acid selected from the group consisting of amino acids with non-polar or non-charged side chains and aromatic ring structures, wherein $X_5$ is an amino acid selected from the group consisting of amino acids with non-polar or non-charged side chains and aromatic rings structures, wherein $X_6$ is an amino acid selected from the group consisting of G and amino acids with non-polar side chains, wherein $X_7$ is an amino acid selected from the group consisting of amino acids with an $NH_2$ group side chain, wherein $X_{11}$ is an amino acid selected from the group consisting of amino acids with negatively charged side chains, wherein $X_{12}$ is an amino acid selected from the group consisting of G and amino acids with non-polar side chains, wherein $X_{13}$ is an amino acid selected from the group consisting of amino acids with non-polar or non-charged side chains and aromatic rings structures, and wherein $X_{14}$ is an amino acid selected from the group consisting of amino acids with an $NH_2$ group side chain, and wherein the peptide comprises at least $X_7$-R-W-H-$X_{11}$ of SEQ ID NO: 9, wherein $X_7$ is an amino acid selected from the group consisting of amino acids with an $NH_2$ group side chain, and wherein $X_{11}$ is an amino acid selected from the group consisting of amino acids with negatively charged side chains, or a peptidomimetic thereof.

4. The method of claim 1, wherein said compound comprises a peptide comprising the amino acid sequence N-R-W-H-E (SEQ ID NO: 2), or the amino acid sequence K-E-Q-W-F-G-N-R-W-H-E-G-Y-R (SEQ ID NO: 6), or a peptidomimetic thereof.

5. The method of claim 1, wherein said compound is a modified form of said peptide or said peptidomimetic.

6. The method of claim 5, wherein said compound is a pegylated, hesylated, pasylated, myristoylated, glycosylated, and/or cyclic form of said peptide or peptidomimetic.

7. The method of claim 1, wherein the compound is formulated for oral, nasal, or subcutaneous administration.

8. The method of claim 1, wherein said pancreatic cancer has already formed metastases.

9. The method of claim 1, wherein the pancreatic cancer is an exocrine or endocrine pancreatic cancer.

10. The method of claim 1, wherein the compound is comprised within a pharmaceutical composition.

11. The method of claim 10, wherein the pharmaceutical composition further comprises a pharmaceutically acceptable excipient.

12. A method for inhibiting, regressing, or preventing metastatic pancreatic tumor growth in a patient, comprising administering a compound comprising a peptide comprising the amino acid sequence N-R-W-H-E (SEQ ID NO: 2), or the amino acid sequence K-E-Q-W-F-G-N-R-W-H-E-G-Y-R (SEQ ID NO: 6), or a peptidomimetic thereof to the patient in need thereof, wherein said pancreatic cancer is classifiable as Stage IV according to the Tumor Node Metastasis (TNM) anatomic/prognostic group system of the cancer staging system of the American Joint Committee on Cancer.

13. The method of claim 12, wherein the peptide is comprised within a pharmaceutical composition.

14. The method of claim 13, wherein the pharmaceutical composition further comprises a pharmaceutically acceptable excipient.

15. A method for inhibiting, regressing, or treating metastatic pancreatic tumor growth in a patient, comprising administering a compound comprising a peptide comprising the amino acid sequence N-R-W-H-E (SEQ ID NO: 2), or the amino acid sequence K-E-Q-W-F-G-N-R-W-H-E-G-Y-R (SEQ ID NO: 6), or a peptidomimetic thereof to the patient in need thereof.

* * * * *

SEQUENCE LISTING

```
<160> NUMBER OF SEQ ID NOS: 18

<210> SEQ ID NO 1
<211> LENGTH: 5
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: (1)..(1)
<223> OTHER INFORMATION: /replace="Ala"
        /replace="Cys"
        /replace="Asp"
        /replace="Glu"
        /replace="Phe"
        /replace="Gly"
        /replace="His"
        /replace="Ile"
        /replace="Lys"
        /replace="Leu"
        /replace="Met"
        /replace="Pro"
        /replace="Gln"
        /replace="Arg"
        /replace="Ser"
        /replace="Thr"
        /replace="Val"
        /replace="Trp"
        /replace="Tyr"
<220> FEATURE:
<221> NAME/KEY: VARIANT
<222> LOCATION: (5)..(5)
<223> OTHER INFORMATION: /replace="Ala"
        /replace="Cys"
        /replace="Asp"
        /replace="Phe"
        /replace="Gly"
        /replace="His"
        /replace="Ile"
        /replace="Lys"
        /replace="Leu"
        /replace="Met"
        /replace="Asn"
        /replace="Pro"
        /replace="Gln"
        /replace="Arg"
        /replace="Ser"
        /replace="Thr"
        /replace="Val"
        /replace="Trp"
        /replace="Tyr"

<400> SEQUENCE: 1

Asn Arg Trp His Glu
1               5

<210> SEQ ID NO 2
<211> LENGTH: 5
<212> TYPE: PRT
```

```
<213> ORGANISM: Artificial Sequence
<220> FEATURE:
<223> OTHER INFORMATION: peptide

<400> SEQUENCE: 2

Asn Arg Trp His Glu
1               5

<210> SEQ ID NO 3
<211> LENGTH: 5
<212> TYPE: PRT
<213> ORGANISM: Artificial Sequence
<220> FEATURE:
<223> OTHER INFORMATION: peptide

<400> SEQUENCE: 3

Ala Arg Trp His Ala
1               5

<210> SEQ ID NO 4
<211> LENGTH: 5
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: (1)..(1)
<223> OTHER INFORMATION: /replace="Lys"
      /replace="Arg"
      /replace="Gln"
      /replace="Ala"
      /replace="Val"
      /replace="Leu"
      /replace="Ile"
<220> FEATURE:
<221> NAME/KEY: VARIANT
<222> LOCATION: (5)..(5)
<223> OTHER INFORMATION: /replace="Asp"
      /replace="Ala"
      /replace="Val"
      /replace="Leu"
      /replace="Ile"

<400> SEQUENCE: 4

Asn Arg Trp His Glu
1               5

<210> SEQ ID NO 5
<211> LENGTH: 5
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: (1)..(1)
<223> OTHER INFORMATION: /replace="Lys"
      /replace="Arg"
      /replace="Gln"
<220> FEATURE:
<221> NAME/KEY: VARIANT
<222> LOCATION: (5)..(5)
<223> OTHER INFORMATION: /replace="Asp"

<400> SEQUENCE: 5

Asn Arg Trp His Glu
1               5

<210> SEQ ID NO 6
<211> LENGTH: 14
```

```
<212> TYPE: PRT
<213> ORGANISM: Artificial Sequence
<220> FEATURE:
<223> OTHER INFORMATION: peptide

<400> SEQUENCE: 6

Lys Glu Gln Trp Phe Gly Asn Arg Trp His Glu Gly Tyr Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: (1)..(1)
<223> OTHER INFORMATION: /replace="Ala"
       /replace="Cys"
       /replace="Asp"
       /replace="Glu"
       /replace="Phe"
       /replace="Gly"
       /replace="His"
       /replace="Ile"
       /replace="Leu"
       /replace="Met"
       /replace="Asn"
       /replace="Pro"
       /replace="Gln"
       /replace="Arg"
       /replace="Ser"
       /replace="Thr"
       /replace="Val"
       /replace="Trp"
       /replace="Tyr"
<220> FEATURE:
<221> NAME/KEY: VARIANT
<222> LOCATION: (2)..(2)
<223> OTHER INFORMATION: /replace="Ala"
       /replace="Cys"
       /replace="Asp"
       /replace="Phe"
       /replace="Gly"
       /replace="His"
       /replace="Ile"
       /replace="Lys"
       /replace="Leu"
       /replace="Met"
       /replace="Asn"
       /replace="Pro"
       /replace="Gln"
       /replace="Arg"
       /replace="Ser"
       /replace="Thr"
       /replace="Val"
       /replace="Trp"
       /replace="Tyr"
<220> FEATURE:
<221> NAME/KEY: VARIANT
<222> LOCATION: (3)..(3)
<223> OTHER INFORMATION: /replace="Ala"
       /replace="Cys"
       /replace="Asp"
       /replace="Glu"
       /replace="Phe"
       /replace="Gly"
       /replace="His"
       /replace="Ile"
       /replace="Lys"
       /replace="Leu"
       /replace="Met"
       /replace="Asn"
       /replace="Pro"
       /replace="Arg"
       /replace="Ser"
```

/replace="Thr"
        /replace="Val"
        /replace="Trp"
        /replace="Tyr"
<220> FEATURE:
<221> NAME/KEY: VARIANT
<222> LOCATION: (4)..(4)
<223> OTHER INFORMATION: /replace="Ala"
        /replace="Cys"
        /replace="Asp"
        /replace="Glu"
        /replace="Phe"
        /replace="Gly"
        /replace="His"
        /replace="Ile"
        /replace="Lys"
        /replace="Leu"
        /replace="Met"
        /replace="Asn"
        /replace="Pro"
        /replace="Gln"
        /replace="Arg"
        /replace="Ser"
        /replace="Thr"
        /replace="Val"
        /replace="Tyr"
<220> FEATURE:
<221> NAME/KEY: VARIANT
<222> LOCATION: (5)..(5)
<223> OTHER INFORMATION: /replace="Ala"
        /replace="Cys"
        /replace="Asp"
        /replace="Glu"
        /replace="Gly"
        /replace="His"
        /replace="Ile"
        /replace="Lys"
        /replace="Leu"
        /replace="Met"
        /replace="Asn"
        /replace="Pro"
        /replace="Gln"
        /replace="Arg"
        /replace="Ser"
        /replace="Thr"
        /replace="Val"
        /replace="Trp"
        /replace="Tyr"
<220> FEATURE:
<221> NAME/KEY: VARIANT
<222> LOCATION: (6)..(6)
<223> OTHER INFORMATION: /replace="Ala"
        /replace="Cys"
        /replace="Asp"
        /replace="Glu"
        /replace="Phe"
        /replace="His"
        /replace="Ile"
        /replace="Lys"
        /replace="Leu"
        /replace="Met"
        /replace="Asn"
        /replace="Pro"
        /replace="Gln"
        /replace="Arg"
        /replace="Ser"
        /replace="Thr"
        /replace="Val"
        /replace="Trp"
        /replace="Tyr"
<220> FEATURE:
<221> NAME/KEY: VARIANT
<222> LOCATION: (7)..(7)
<223> OTHER INFORMATION: /replace="Ala"
        /replace="Cys"
        /replace="Asp"
        /replace="Glu"
        /replace="Phe"
        /replace="Gly"

```
        /replace="His"
        /replace="Ile"
        /replace="Lys"
        /replace="Leu"
        /replace="Met"
        /replace="Pro"
        /replace="Gln"
        /replace="Arg"
        /replace="Ser"
        /replace="Thr"
        /replace="Val"
        /replace="Trp"
        /replace="Tyr"
<220> FEATURE:
<221> NAME/KEY: VARIANT
<222> LOCATION: (11)..(11)
<223> OTHER INFORMATION: /replace="Ala"
        /replace="Cys"
        /replace="Asp"
        /replace="Phe"
        /replace="Gly"
        /replace="His"
        /replace="Ile"
        /replace="Lys"
        /replace="Leu"
        /replace="Met"
        /replace="Asn"
        /replace="Pro"
        /replace="Gln"
        /replace="Arg"
        /replace="Ser"
        /replace="Thr"
        /replace="Val"
        /replace="Trp"
        /replace="Tyr"
<220> FEATURE:
<221> NAME/KEY: VARIANT
<222> LOCATION: (12)..(12)
<223> OTHER INFORMATION: /replace="Ala"
        /replace="Cys"
        /replace="Asp"
        /replace="Glu"
        /replace="Phe"
        /replace="His"
        /replace="Ile"
        /replace="Lys"
        /replace="Leu"
        /replace="Met"
        /replace="Asn"
        /replace="Pro"
        /replace="Gln"
        /replace="Arg"
        /replace="Ser"
        /replace="Thr"
        /replace="Val"
        /replace="Trp"
        /replace="Tyr"
<220> FEATURE:
<221> NAME/KEY: VARIANT
<222> LOCATION: (13)..(13)
<223> OTHER INFORMATION: /replace="Ala"
        /replace="Cys"
        /replace="Asp"
        /replace="Glu"
        /replace="Phe"
        /replace="Gly"
        /replace="His"
        /replace="Ile"
        /replace="Lys"
        /replace="Leu"
        /replace="Met"
        /replace="Asn"
        /replace="Pro"
        /replace="Gln"
        /replace="Arg"
        /replace="Ser"
        /replace="Thr"
        /replace="Val"
        /replace="Trp"
```

```
<220> FEATURE:
<221> NAME/KEY: VARIANT
<222> LOCATION: (14)..(14)
<223> OTHER INFORMATION: /replace="Ala"
      /replace="Cys"
      /replace="Asp"
      /replace="Glu"
      /replace="Phe"
      /replace="Gly"
      /replace="His"
      /replace="Ile"
      /replace="Lys"
      /replace="Leu"
      /replace="Met"
      /replace="Asn"
      /replace="Pro"
      /replace="Gln"
      /replace="Ser"
      /replace="Thr"
      /replace="Val"
      /replace="Trp"
      /replace="Tyr"

<400> SEQUENCE: 7

Lys Glu Gln Trp Phe Gly Asn Arg Trp His Glu Gly Tyr Arg
1               5                   10

<210> SEQ ID NO 8
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: (1)..(1)
<223> OTHER INFORMATION: /replace="Arg"
      /replace="Asn"
      /replace="Gln"
      /replace="Ala"
      /replace="Val"
      /replace="Leu"
      /replace="Ile"
<220> FEATURE:
<221> NAME/KEY: VARIANT
<222> LOCATION: (2)..(2)
<223> OTHER INFORMATION: /replace="Asp"
      /replace="Ala"
      /replace="Val"
      /replace="Leu"
      /replace="Ile"
<220> FEATURE:
<221> NAME/KEY: VARIANT
<222> LOCATION: (3)..(3)
<223> OTHER INFORMATION: /replace="Lys"
      /replace="Arg"
      /replace="Asn"
      /replace="Ala"
      /replace="Val"
      /replace="Leu"
      /replace="Ile"
<220> FEATURE:
<221> NAME/KEY: VARIANT
<222> LOCATION: (4)..(4)
<223> OTHER INFORMATION: /replace="Phe"
      /replace="Tyr"
      /replace="Ala"
      /replace="Val"
      /replace="Leu"
      /replace="Ile"
<220> FEATURE:
<221> NAME/KEY: VARIANT
<222> LOCATION: (5)..(5)
<223> OTHER INFORMATION: /replace="Trp"
      /replace="Tyr"
      /replace="Ala"
      /replace="Val"
```

-continued

```
      /replace="Leu"
      /replace="Ile"
<220> FEATURE:
<221> NAME/KEY: VARIANT
<222> LOCATION: (6)..(6)
<223> OTHER INFORMATION: /replace="Ala"
      /replace="Val"
      /replace="Leu"
      /replace="Ile"
<220> FEATURE:
<221> NAME/KEY: VARIANT
<222> LOCATION: (7)..(7)
<223> OTHER INFORMATION: /replace="Lys"
      /replace="Arg"
      /replace="Gln"
      /replace="Ala"
      /replace="Val"
      /replace="Leu"
      /replace="Ile"
<220> FEATURE:
<221> NAME/KEY: VARIANT
<222> LOCATION: (11)..(11)
<223> OTHER INFORMATION: /replace="Asp"
      /replace="Ala"
      /replace="Val"
      /replace="Leu"
      /replace="Ile"
<220> FEATURE:
<221> NAME/KEY: VARIANT
<222> LOCATION: (12)..(12)
<223> OTHER INFORMATION: /replace="Ala"
      /replace="Val"
      /replace="Leu"
      /replace="Ile"
<220> FEATURE:
<221> NAME/KEY: VARIANT
<222> LOCATION: (13)..(13)
<223> OTHER INFORMATION: /replace="Phe"
      /replace="Trp"
      /replace="Ala"
      /replace="Val"
      /replace="Leu"
      /replace="Ile"
<220> FEATURE:
<221> NAME/KEY: VARIANT
<222> LOCATION: (14)..(14)
<223> OTHER INFORMATION: /replace="Lys"
      /replace="Asn"
      /replace="Gln"
      /replace="Ala"
      /replace="Val"
      /replace="Leu"
      /replace="Ile"

<400> SEQUENCE: 8

Lys Glu Gln Trp Phe Gly Asn Arg Trp His Glu Gly Tyr Arg
1               5                   10

<210> SEQ ID NO 9
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: (1)..(1)
<223> OTHER INFORMATION: /replace="Arg"
      /replace="Asn"
      /replace="Gln"
<220> FEATURE:
<221> NAME/KEY: VARIANT
<222> LOCATION: (2)..(2)
<223> OTHER INFORMATION: /replace="Asp"
<220> FEATURE:
<221> NAME/KEY: VARIANT
<222> LOCATION: (3)..(3)
```

```
<223> OTHER INFORMATION: /replace="Lys"
      /replace="Arg"
      /replace="Asn"
<220> FEATURE:
<221> NAME/KEY: VARIANT
<222> LOCATION: (4)..(4)
<223> OTHER INFORMATION: /replace="Phe"
      /replace="Tyr"
<220> FEATURE:
<221> NAME/KEY: VARIANT
<222> LOCATION: (5)..(5)
<223> OTHER INFORMATION: /replace="Trp"
      /replace="Tyr"
<220> FEATURE:
<221> NAME/KEY: VARIANT
<222> LOCATION: (6)..(6)
<223> OTHER INFORMATION: /replace="Ala"
      /replace="Val"
      /replace="Leu"
      /replace="Ile"
<220> FEATURE:
<221> NAME/KEY: VARIANT
<222> LOCATION: (7)..(7)
<223> OTHER INFORMATION: /replace="Lys"
      /replace="Arg"
      /replace="Gln"
<220> FEATURE:
<221> NAME/KEY: VARIANT
<222> LOCATION: (11)..(11)
<223> OTHER INFORMATION: /replace="Asp"
<220> FEATURE:
<221> NAME/KEY: VARIANT
<222> LOCATION: (12)..(12)
<223> OTHER INFORMATION: /replace="Ala"
      /replace="Val"
      /replace="Leu"
      /replace="Ile"
<220> FEATURE:
<221> NAME/KEY: VARIANT
<222> LOCATION: (13)..(13)
<223> OTHER INFORMATION: /replace="Phe"
      /replace="Trp"
<220> FEATURE:
<221> NAME/KEY: VARIANT
<222> LOCATION: (14)..(14)
<223> OTHER INFORMATION: /replace="Lys"
      /replace="Asn"
      /replace="Gln"

<400> SEQUENCE: 9

Lys Glu Gln Trp Phe Gly Asn Arg Trp His Glu Gly Tyr Arg
1               5                   10

<210> SEQ ID NO 10
<211> LENGTH: 14
<212> TYPE: PRT
<213> ORGANISM: Artificial Sequence
<220> FEATURE:
<223> OTHER INFORMATION: peptide

<400> SEQUENCE: 10

Lys Glu Lys Trp Phe Glu Asn Glu Trp Gln Gly Lys Asn Pro
1               5                   10

<210> SEQ ID NO 11
<211> LENGTH: 5
<212> TYPE: PRT
<213> ORGANISM: Artificial Sequence
<220> FEATURE:
<223> OTHER INFORMATION: peptide

<400> SEQUENCE: 11

Asn Glu Trp Gln Gly
1               5
```

<210> SEQ ID NO 12
<211> LENGTH: 11
<212> TYPE: PRT
<213> ORGANISM: Artificial Sequence
<220> FEATURE:
<223> OTHER INFORMATION: peptide

<400> SEQUENCE: 12

Trp Phe Glu Asn Glu Trp Gln Gly Lys Asn Pro
1               5                   10

<210> SEQ ID NO 13
<211> LENGTH: 11
<212> TYPE: PRT
<213> ORGANISM: Artificial Sequence
<220> FEATURE:
<223> OTHER INFORMATION: peptide

<400> SEQUENCE: 13

Trp Phe Gln Asn Gly Trp Gln Gly Lys Asn Pro
1               5                   10

<210> SEQ ID NO 14
<211> LENGTH: 11
<212> TYPE: PRT
<213> ORGANISM: Artificial Sequence
<220> FEATURE:
<223> OTHER INFORMATION: peptide

<400> SEQUENCE: 14

Trp Phe Gly Asn Arg Trp His Glu Gly Tyr Arg
1               5                   10

<210> SEQ ID NO 15
<211> LENGTH: 5
<212> TYPE: PRT
<213> ORGANISM: Artificial Sequence
<220> FEATURE:
<223> OTHER INFORMATION: peptide

<400> SEQUENCE: 15

Asn Ala Ala Ala Gly
1               5

<210> SEQ ID NO 16
<211> LENGTH: 8
<212> TYPE: PRT
<213> ORGANISM: Artificial Sequence
<220> FEATURE:
<223> OTHER INFORMATION: peptide

<400> SEQUENCE: 16

Phe Gly Asn Arg Trp His Glu Gly
1               5

<210> SEQ ID NO 17
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: (1)..(1)
<223> OTHER INFORMATION: /replace="Ala"
      /replace="Cys"
      /replace="Asp"

-continued

```
        /replace="Glu"
        /replace="Gly"
        /replace="His"
        /replace="Ile"
        /replace="Lys"
        /replace="Leu"
        /replace="Met"
        /replace="Asn"
        /replace="Pro"
        /replace="Gln"
        /replace="Arg"
        /replace="Ser"
        /replace="Thr"
        /replace="Val"
        /replace="Trp"
        /replace="Tyr"
<220> FEATURE:
<221> NAME/KEY: VARIANT
<222> LOCATION: (2)..(2)
<223> OTHER INFORMATION: /replace="Ala"
        /replace="Cys"
        /replace="Asp"
        /replace="Glu"
        /replace="Phe"
        /replace="His"
        /replace="Ile"
        /replace="Lys"
        /replace="Leu"
        /replace="Met"
        /replace="Asn"
        /replace="Pro"
        /replace="Gln"
        /replace="Arg"
        /replace="Ser"
        /replace="Thr"
        /replace="Val"
        /replace="Trp"
        /replace="Tyr"
<220> FEATURE:
<221> NAME/KEY: VARIANT
<222> LOCATION: (3)..(3)
<223> OTHER INFORMATION: /replace="Ala"
        /replace="Cys"
        /replace="Asp"
        /replace="Glu"
        /replace="Phe"
        /replace="Gly"
        /replace="His"
        /replace="Ile"
        /replace="Lys"
        /replace="Leu"
        /replace="Met"
        /replace="Pro"
        /replace="Gln"
        /replace="Arg"
        /replace="Ser"
        /replace="Thr"
        /replace="Val"
        /replace="Trp"
        /replace="Tyr"
<220> FEATURE:
<221> NAME/KEY: VARIANT
<222> LOCATION: (7)..(7)
<223> OTHER INFORMATION: /replace="Ala"
        /replace="Cys"
        /replace="Asp"
        /replace="Phe"
        /replace="Gly"
        /replace="His"
        /replace="Ile"
        /replace="Lys"
        /replace="Leu"
        /replace="Met"
        /replace="Asn"
        /replace="Pro"
        /replace="Gln"
        /replace="Arg"
        /replace="Ser"
        /replace="Thr"
```

```
        /replace="Val"
        /replace="Trp"
        /replace="Tyr"
<220> FEATURE:
<221> NAME/KEY: VARIANT
<222> LOCATION: (8)..(8)
<223> OTHER INFORMATION: /replace="Ala"
        /replace="Cys"
        /replace="Asp"
        /replace="Glu"
        /replace="Phe"
        /replace="His"
        /replace="Ile"
        /replace="Lys"
        /replace="Leu"
        /replace="Met"
        /replace="Asn"
        /replace="Pro"
        /replace="Gln"
        /replace="Arg"
        /replace="Ser"
        /replace="Thr"
        /replace="Val"
        /replace="Trp"
        /replace="Tyr"

<400> SEQUENCE: 17

Phe Gly Asn Arg Trp His Glu Gly
1               5

<210> SEQ ID NO 18
<211> LENGTH: 8
<212> TYPE: PRT
<213> ORGANISM: Artificial Sequence
<220> FEATURE:
<223> OTHER INFORMATION: peptide

<400> SEQUENCE: 18

Lys Gly Asn Arg Trp His Glu Gly
1               5
```